(12) United States Patent
Chapman et al.

(10) Patent No.: US 10,556,988 B2
(45) Date of Patent: Feb. 11, 2020

(54) CATALYSTS

(71) Applicant: Econic Technologies Ltd, London (GB)

(72) Inventors: Andy Chapman, London (GB);
Anthony Chartoire, Cheshire (GB);
James Leeland, Hertfordshire (GB);
Michael Kember, London (GB); Louis Adriaenssens, London (GB)

(73) Assignee: ECONIC TECHNOLOGIES LTD, London (GB)

( * ) Notice: Subject to any disclaimer, the term of this patent is extended or adjusted under 35 U.S.C. 154(b) by 0 days.

(21) Appl. No.: 15/327,806

(22) PCT Filed: Jul. 22, 2015

(86) PCT No.: PCT/GB2015/052114
§ 371 (c)(1),
(2) Date: Jan. 20, 2017

(87) PCT Pub. No.: WO2016/012785
PCT Pub. Date: Jan. 28, 2016

(65) Prior Publication Data
US 2017/0210848 A1 Jul. 27, 2017

(30) Foreign Application Priority Data

| Jul. 22, 2014 | (GB) | 1412986.0 |
| Jul. 22, 2014 | (GB) | 1412990.2 |
| Jul. 22, 2014 | (GB) | 1412992.8 |

(51) Int. Cl.
*C08G 64/00* (2006.01)
*C08G 64/34* (2006.01)
(Continued)

(52) U.S. Cl.
CPC .......... *C08G 64/34* (2013.01); *B01J 31/1835* (2013.01); *B01J 31/226* (2013.01); *B01J 31/2239* (2013.01); *B01J 31/2243* (2013.01); *C07D 257/02* (2013.01); *C07D 285/00* (2013.01); *C07D 487/08* (2013.01); *C08G 63/823* (2013.01); *B01J 2531/0216* (2013.01);
(Continued)

(58) Field of Classification Search
None
See application file for complete search history.

(56) References Cited

U.S. PATENT DOCUMENTS

2009/0062110 A1  3/2009  Koshino et al.
2013/0172524 A1* 7/2013  Farmer .......... C07F 5/069
528/405

FOREIGN PATENT DOCUMENTS

EP  1988084 A1  11/2008
EP  2285490 B1  6/2014
(Continued)

OTHER PUBLICATIONS

Written Opinion for Singapore Application No. 11201700229V dated Oct. 11, 2017 (7 pages).
Sujit K. Dutta, et al., "Model Compounds for Iron Proteins, Structures and Magnetic, Spectroscopic, and Redox Properties of FeIIIMII and [CoIIIFeIII]2O Complexes with (μ-Carboxylato)bis(μ-phenoxo)dimetalate and (μ-Oxo)diiron (III) Cores", Inorganic Chemistry 1996, vol. 35, No. 8, 2292-2300, American Chemical Society (9 pages.).
Ki Ju Kim et al., "Synthesis and Characterization of Dinuclear Ni(II) Complexes with Tetraazadiphenol Macrocycle Bearing Cyclohexanes", Bull. Korean Chem. Soc., 2006, vol. 27, No. 11, 1747-1751 (5 pages.).
(Continued)

*Primary Examiner* — Yun Qian
(74) *Attorney, Agent, or Firm* — Shumaker, Loop & Kendrick, LLP

(57) ABSTRACT

The present invention relates to the field of polymerisation catalysts, and systems comprising said catalysts for polymerising carbon dioxide and an epoxide, a lactide and/or lactone, and/or an epoxide and an anhydride. The catalyst is of formula (I):

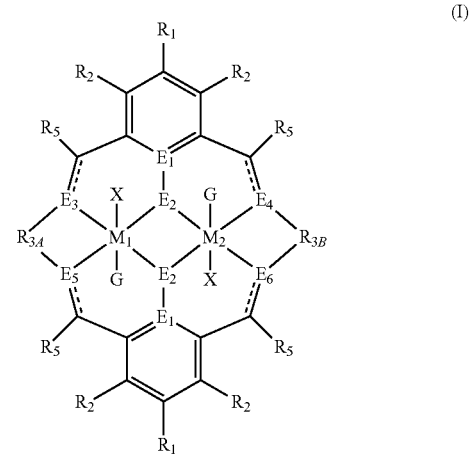

Wherein $M_1$ and $M_2$ are independently selected from Zn(II), Cr(II), Co(II), Cu(II), Mn(II), Ni(II), Mg(II), Fe(II), Ti(II), V(II), Cr(III)-X, Co(III)-X, Ni(III)-X, Mn(III)-X, Fe(III)-X, Ca(II), Ge(II), Al(III)-X, Ti(III)-X, V(III)-X, Ge(IV)-(X)$_2$ or Ti(IV)-(X)$_2$. $R_{3A}$ is different from $R_{3B}$; and/or at least one occurrence of $E_3$, $E_4$, $E_5$ and $E_6$ is different to a remaining occurrence of $E_3$, $E_4$, $E_5$ and $E_6$. A ligand, a process of asymmetric N-substitution of a symmetrical ligand and a process for the reaction of: (i) carbon dioxide with an epoxide; (ii) an epoxide and an anhydride; and/or (iii) a lactide and/or a lactone, in the presence of a catalyst is also described.

5 Claims, No Drawings

(51) Int. Cl.
*B01J 31/18* (2006.01)
*B01J 31/22* (2006.01)
*C08G 63/82* (2006.01)
*C07D 257/02* (2006.01)
*C07D 285/00* (2006.01)
*C07D 487/08* (2006.01)

(52) U.S. Cl.
CPC .... *B01J 2531/0252* (2013.01); *B01J 2531/16* (2013.01); *B01J 2531/22* (2013.01); *B01J 2531/23* (2013.01); *B01J 2531/26* (2013.01); *B01J 2531/31* (2013.01); *B01J 2531/46* (2013.01); *B01J 2531/56* (2013.01); *B01J 2531/62* (2013.01); *B01J 2531/72* (2013.01); *B01J 2531/842* (2013.01); *B01J 2531/845* (2013.01); *B01J 2531/847* (2013.01)

(56) References Cited

FOREIGN PATENT DOCUMENTS

| JP | 63-280086 A | 11/1988 |
|---|---|---|
| JP | 2007-238601 A | 9/2007 |
| JP | 2011-518911 A | 6/2011 |
| JP | 2013-539802 A | 10/2013 |
| WO | 2009/130470 A1 | 10/2009 |
| WO | 2012037282 A2 | 3/2012 |
| WO | 2013007759 A1 | 1/2013 |
| WO | 2013/034750 A2 | 3/2013 |

OTHER PUBLICATIONS

Abstract Only. S. J. Na et al., "Bimetallic nickel complexes of macrocyclic tetralminodiphenols and their ethylene polymerization", J. Organometallic Chemc. vol. 691, No. 4, p. 611-620, Feb. 1, 2006 (2 pgs.).

Ramprasad Das, et al., "Carboxylate Bridging of Amino Acids in Dinuclear Macrocyclic Nickel (II) Complexes", J. Chem. Soc., Dalton Trans. 1992, Issue 1., No. 7, 1253-1257 (5 pages.).

Saini, P.K. et al. "Dinuclear metal catalysts: improved performance of heterodinuclear mixed catalysts for CO2-epoxide copolymerization", Chem. Commum., vol. 50, p. 4164-4167, Feb. 20, 2014.

International Search Report for PCT/GB2015/052114 dated Nov. 30, 2015 (5 pages).

Kausik K. Nanda et al., "Formation of Mixed Spin-state Macrocyclic Dinickel (i1) Complexes through Variation of Hole Size", J. Chem. Soc. Dalton Trans, 1993, pp. 2515-2520 (6 pages).

Yuichiro Aratake et al., "Dinuclear nickel (II) complexes of a series of dinucleating macrocycles with similar or dissimilar coordination sites: synthesis, structure and physicochemical property", Inorganica Chimica Acta, vol. 212, No. 1-2, 1993 pp. 183-190 (8 pages).

Michael R. Kember, et al., "Highly Active Di- and Trimetallic Cobalt Catalysts for the Copolymerization of CHO and CO2 at Atmospheric Pressure," Macromolecules 2010, vol. 43, No. 5, Mar. 9, 2010, pp. 2291-2298 (8 pages).

Antoine Buchard, et al., "A bimetallic iron (III) catalyst for CO2/epoxide coupling," Chemical Communications, vol. 47, No. 1, Sep. 27, 2010, pp. 212-214 (4 pages).

Jun Nishio, et al., Heterodinuclear Ni(II)M(II) (M=Pb, Mn, Fe, Co, Ni, Cu, Zn) complexes of a phenol-based dinucleating macrocycle with dissimilar 4- and 5-coordination sites, Inorganica Chimica Acta, 218 (1994) pp. 27-32 (6 pages).

International Preliminary Report on Patentability for PCT/GB2015/052114 dated Jan. 24, 2017 (9 pages).

English translation of Examination Report with a Search Report for Taiwanese Patent Application No. 104123691, dated Oct. 25, 2018 (9 pages).

Yuichiro Aratake et al., "Dinuclear nickel (II) complexes of a series of dinucleating macrocycles with similar or dissimilar coordination sites: synthesis, structure and physicochemical property", Inorganica Chimica Acta, vol. 212, p. 183-190 (1993).

Elena V. Ryback-Akimova et al., "Dicompartmental Ligands with Hexa- and Tetradentate Coordination Sites: One-Step Synthesis of Ligands and Metal Complexes and Their X-ray Structure Analysis", Inorg. Chem., vol. 37, p. 1563-1574 (1998).

* cited by examiner

CATALYSTS

FIELD OF THE INVENTION

The present invention relates to the field of polymerisation catalysts, and systems comprising said catalysts for polymerising carbon dioxide and an epoxide, a lactide and/or lactone, and/or an epoxide and an anhydride.

BACKGROUND

Environmental and economic concerns associated with depleting oil resources have triggered a growing interest in the chemical conversion of carbon dioxide ($CO_2$), so as to enable its use as a renewable carbon source. $CO_2$ is, despite its low reactivity, a highly attractive carbon feedstock, as it is inexpensive, virtually non-toxic, abundantly available in high purity and non-hazardous. Therefore, $CO_2$ could be a promising substitute for substances such as carbon monoxide, phosgene or other petrochemical feedstocks in many processes. One of the developing applications of $CO_2$ is the copolymerization with epoxides to yield aliphatic polycarbonates. The development of effective catalysts to make such a process profitable is the subject of continuous research.

In WO2009/130470, the contents of which are incorporated herein by reference in their entirety, the copolymerisation of an epoxide with $CO_2$ using a catalyst of a class represented by formula (I) was described:

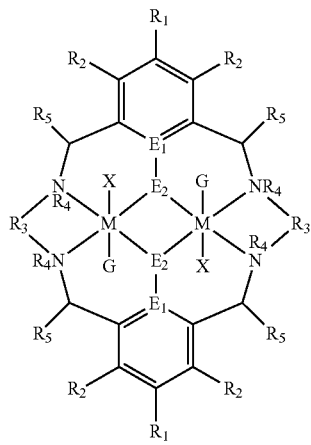

(I)

WO2013/034750, the contents of which are incorporated herein by reference in their entirety, discloses the copolymerisation of an epoxide with $CO_2$ in the presence of a chain transfer agent using a catalyst of a class represented by formula (I):

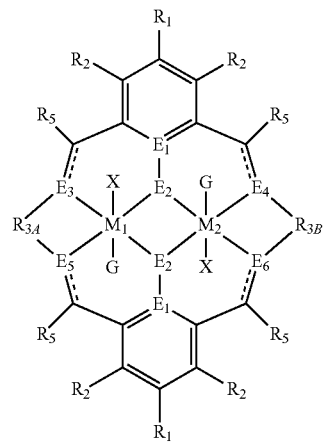

(I)

Various compounds according to formula (I) above were tested for their ability to catalyse the reaction between different epoxides and carbon dioxide.

In each of these tested catalysts, both occurrences of $R_3$ were the same and all occurrence of $R_4$ were the same (referred to hereinafter as symmetric catalysts).

Among the epoxides employed in the copolymerization reactions of the prior art, cyclohexene oxide (CHO) received special interest, as the product, poly(cyclohexene carbonate) (PCHC) shows a high glass transition temperature and reasonable tensile strength. Ethylene oxide, propylene oxide and butylene oxide have also received interest as they produce polymers (polyalkylene carbonates, such as PPC) with elastomeric properties which are useful in many applications e.g. films.

The inventors have now surprisingly found that the asymmetric catalysts referred to herein represent a novel and inventive means of catalysing the polymerisation of carbon dioxide with various monomers to produce useful polymer products with good activity and selectivity.

SUMMARY OF THE INVENTION

According to a first aspect of the present invention, there is provided a catalyst of formula (I):

wherein:
$M_1$ and $M_2$ are independently selected from Zn(II), CO(II), Co(II), Cu(II), Ni(II), Mn(II), Mg(II), Fe(II), Ti(II), V(II), Cr(III)-X, Co(III)-X, Ni(III)-X, Mn(III)-X, Fe(III)-X, Ca(II), Ge(II), Al(III)-X, Ti(III)-X, V(III)-X, Ge(IV)-(X)$_2$ or Ti(IV)-(X)$_2$;

$R_1$ and $R_2$ are independently selected from hydrogen, halide, a nitro group, a nitrile group, an imine, an amine, an ether group, a silyl group, a silyl ether group, a sulfoxide group, a sulfonyl group, a sulfinate group or an acetylide group or an optionally substituted alkyl, alkenyl, alkynyl, haloalkyl, aryl, heteroaryl, alkoxy, aryloxy, alkylthio, arylthio, alicyclic or heteroalicyclic group;

$R_{3A}$ and $R_{3B}$ are independently selected from optionally substituted alkylene, alkenylene, alkynylene, heteroalkylene, heteroalkenylene, heteroalkynylene, arylene, heteroarylene or cycloalkylene, wherein alkylene, alkenylene, alkynylene, heteroalkylene, heteroalkenylene and heteroalkynylene, may optionally be interrupted by aryl, heteroaryl, alicyclic or heteroalicyclic;

$R_5$ is independently selected from H, or optionally substituted aliphatic, heteroaliphatic, alicyclic, heteroalicyclic, aryl, heteroaryl, alkylheteroaryl or alkylaryl;

$E_1$ is C, $E_2$ is O, S or NH or $E_1$ is N and $E_2$ is O;

$E_3$, $E_4$, $E_5$ and $E_6$ are each independently selected from N, NR$_4$, O and S, wherein when any of $E_3$, $E_4$, $E_5$ or $E_6$ are N, ══════ is ═, and wherein when any of $E_3$, $E_4$, $E_5$ or $E_6$ are NR$_4$, O or S, ══════ is ─; $R_4$ is independently selected from H, or optionally substituted aliphatic, heteroaliphatic, alicyclic, heteroalicyclic, aryl, heteroaryl, alkylheteroaryl or alkylaryl;

X is independently selected from OC(O)R$^x$, OSO$_2$R$^x$, OSOR$^x$, OSO(R$^x$)$_2$, S(O)R$^x$, OR$^x$, phosphinate, halide, nitrate, hydroxyl, carbonate, amino, amido or optionally substituted aliphatic, heteroaliphatic, alicyclic, heteroalicyclic, aryl or heteroaryl;

$R_x$ is independently hydrogen, or optionally substituted aliphatic, haloaliphatic, heteroaliphatic, alicyclic, heteroalicyclic, aryl, alkylaryl or heteroaryl; and G is absent or independently selected from a neutral or anionic donor ligand which is a Lewis base;

and wherein:
i) $R_{3A}$ is different from $R_{3B}$; and/or
ii) at least one occurrence of $E_3$, $E_4$, $E_5$ and $E_6$ is different to a remaining occurrence of $E_3$, $E_4$, $E_5$ and $E_6$.

According to a second aspect of the present invention, there is provided a ligand of formula (II):

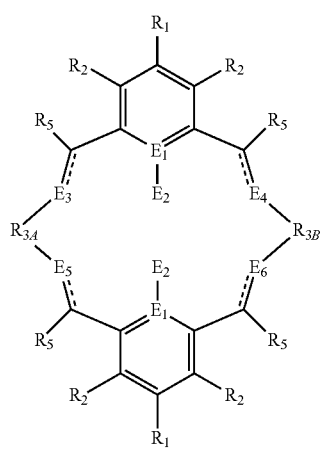

(II)

wherein:
$R_1$ and $R_2$ are independently selected from hydrogen, halide, a nitro group, a nitrile group, an imine, an amine, an ether group, a silyl group, a silyl ether group, a sulfoxide group, a sulfonyl group, a sulfinate group or an acetylide group or an optionally substituted alkyl, alkenyl, alkynyl, haloalkyl, aryl, heteroaryl, alkoxy, aryloxy, alkylthio, arylthio, alicyclic or heteroalicyclic group;

$R_{3A}$ and $R_{3B}$ are independently selected from optionally substituted alkylene, alkenylene, alkynylene, heteroalkylene, heteroalkenylene, heteroalkynylene, arylene, heteroarylene or cycloalkylene, wherein alkylene, alkenylene, alkynylene, heteroalkylene, heteroalkenylene and heteroalkynylene, may optionally be interrupted by aryl, heteroaryl, alicyclic or heteroalicyclic;

$R_5$ is independently selected from H, or optionally substituted aliphatic, heteroaliphatic, alicyclic, heteroalicyclic, aryl, heteroaryl, alkylheteroaryl or alkylaryl;

$E_1$ is C, $E_2$ is OY, S or NH or $E_1$ is N and $E_2$ is O;

Y is hydrogen or an alkali metal;

$E_3$, $E_4$, $E_5$ and $E_6$ are each independently selected from N, NR$_4$, O and S, wherein when any of $E_3$, $E_4$, $E_5$ or $E_6$ are N, ══════ is ═, and wherein when any of $E_3$, $E_4$, $E_5$ or $E_6$ are NR$_4$, O or S, ══════ is ─; $R_4$ is independently selected from H, or optionally substituted aliphatic, heteroaliphatic, alicyclic, heteroalicyclic, aryl, heteroaryl, alkylheteroaryl or alkylaryl;

and wherein:
i) $R_{3A}$ is different from $R_{3B}$; and/or
ii) at least one occurrence of $E_3$, $E_4$, $E_5$ and $E_6$ is different to a remaining occurrence of $E_3$, $E_4$, $E_5$ and $E_6$.

In a third aspect of the present invention, the invention extends to methods of preparation of ligands, complexes and catalysts according to the second aspect and first aspect respectively or as otherwise defined herein.

In a fourth aspect of the present invention, there is provided a process of asymmetric N-substitution of a symmetrical ligand having a tetraaminophenol coordination sphere, the process comprising the following steps:

a) protecting the amino groups of the coordination sphere of the symmetrical ligand with an optionally substituted alkylene;

b) asymmetrically N-substituting one or more of the protected amino groups of the product of step (a) with a substituent.

In a fifth aspect of the invention, there is provided a process for the reaction of (i) carbon dioxide with an epoxide, (ii) an anhydride and an epoxide, and/or (iii) a lactide and/or a lactone in the presence of a catalyst according to the first aspect, optionally in the presence of a chain transfer agent.

The sixth aspect of the invention provides a product of the process of the fifth aspect of the invention.

Definitions

For the purpose of the present invention, an aliphatic group is a hydrocarbon moiety that may be straight chain or branched and may be completely saturated, or contain one or more units of unsaturation, but which is not aromatic. The term "unsaturated" means a moiety that has one or more double and/or triple bonds. The term "aliphatic" is therefore intended to encompass alkyl, alkenyl or alkynyl groups, and combinations thereof. An aliphatic group is preferably a $C_{1-20}$ aliphatic group, that is, an aliphatic group with 1, 2, 3, 4, 5, 6, 7, 8, 9, 10, 11, 12, 13, 14, 15, 16, 17, 18, 19 or 20 carbon atoms. Preferably, an aliphatic group is a $C_{1-15}$ aliphatic, more preferably a $C_{1-12}$aliphatic, more preferably a $C_{1-10}$aliphatic, even more preferably a $C_{1-8}$aliphatic, such as a $C_{1-6}$aliphatic group.

An alkyl group is preferably a "$C_{1-20}$ alkyl group", that is an alkyl group that is a straight or branched chain with 1 to 20 carbons. The alkyl group therefore has 1, 2, 3, 4, 5, 6, 7, 8, 9, 10, 11, 12, 13, 14, 15, 16, 17, 18, 19 or 20 carbon atoms. Preferably, an alkyl group is a $C_{1-15}$alkyl, preferably a $C_{1-12}$alkyl, more preferably a $C_{1-10}$alkyl, even more preferably a $C_{1-8}$alkyl, even more preferably a $C_{1-6}$alkyl group. Specifically, examples of "$C_{1-20}$ alkyl group" include methyl group, ethyl group, n-propyl group, iso-propyl group, n-butyl group, iso-butyl group, sec-butyl group, tert-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, n-eicosyl group, 1,1-dimethylpropyl group, 1,2-dimethylpropyl group, 2,2-dimethylpropyl group, 1-ethylpropyl group, n-hexyl group, 1-ethyl-2-methylpropyl group, 1,1,2-trimethylpropyl group, 1-ethylbutyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group and the like.

Alkenyl and alkynyl groups are preferably "$C_{2-20}$alkenyl" and "$C_{2-20}$alkynyl", more preferably "$C_{2-15}$alkenyl" and "$C_{2-15}$alkynyl", even more preferably "$C_{2-12}$alkenyl" and "$C_{2-12}$alkynyl", even more preferably "$C_{2-10}$alkenyl" and "$C_{2-10}$alkynyl", even more preferably "$C_{2-8}$alkenyl" and "$C_{2-8}$alkynyl", most preferably "$C_{2-6}$alkenyl" and "$C_{2-6}$alkynyl" groups, respectively. Alkene and alkyne should be understood accordingly.

A heteroaliphatic group is an aliphatic group as described above, which additionally contains one or more heteroatoms. Heteroaliphatic groups therefore preferably contain from 2 to 21 atoms, preferably from 2 to 16 atoms, more preferably from 2 to 13 atoms, more preferably from 2 to 11 atoms, more preferably from 2 to 9 atoms, even more preferably from 2 to 7 atoms, wherein at least one atom is a carbon atom. Particularly preferred heteroatoms are selected from O, S, N, P and Si. When heteroaliphatic groups have two or more heteroatoms, the heteroatoms may be the same or different.

An alicyclic group is a saturated or partially unsaturated cyclic aliphatic monocyclic or polycyclic (including fused, bridging and spiro-fused) ring system which has from 3 to 20 carbon atoms, that is an alicyclic group with 3, 4, 5, 6, 7, 8, 9, 10, 11, 12, 13, 14, 15, 16, 17, 18, 19 or 20 carbon atoms. Preferably, an alicyclic group has from 3 to 15, more preferably from 3 to 12, even more preferably from 3 to 10, even more preferably from 3 to 8 carbon atoms, even more preferably from 3 to 6 carbons atoms. The term "alicyclic" encompasses cycloalkyl, cycloalkenyl and cycloalkynyl groups. It will be appreciated that the alicyclic group may comprise an alicyclic ring bearing one or more linking or non-linking alkyl substituents, such as $CH_2$-cyclohexyl. Specifically, examples of the $C_{3-20}$ cycloalkyl group include cyclopropyl, cyclobutyl, cyclopentyl, cyclohexyl, cycloheptyl, adamantyl and cyclooctyl.

A heteroalicyclic group is an alicyclic group as defined above which has, in addition to carbon atoms, one or more ring heteroatoms, which are preferably selected from O, S, N, P and Si. Heteroalicyclic groups preferably contain from one to four heteroatoms, which may be the same or different. Heterocyclic groups preferably contain from 5 to 20 atoms, more preferably from 5 to 14 atoms, even more preferably from 5 to 12 atoms.

An aryl group is a monocyclic or polycyclic ring system having from 5 to 20 carbon atoms. An aryl group is preferably a "$C_{6-12}$ aryl group" and is an aryl group constituted by 6, 7, 8, 9, 10, 11 or 12 carbon atoms and includes condensed ring groups such as monocyclic ring group, or bicyclic ring group and the like. Specifically, examples of "$C_{6-10}$ aryl group" include phenyl group, biphenyl group, indenyl group, naphthyl group or azulenyl group and the like. It should be noted that condensed rings such as indan and tetrahydro naphthalene are also included in the aryl group.

A heteroaryl group is an aryl group having, in addition to carbon atoms, from one to four ring heteroatoms which are preferably selected from O, S, N, P and Si. A heteroaryl group preferably has from 5 to 20, more preferably from 5 to 14 ring atoms. Specifically, examples of a heteroaryl group include pyridine, imidazole, methylimidazole and dimethylaminopyridine.

Examples of alicyclic, heteroalicyclic, aryl and heteroaryl groups include but are not limited to cyclohexyl, phenyl, acridine, benzimidazole, benzofuran, benzothiophene, benzoxazole, benzothiazole, carbazole, cinnoline, dioxin, dioxane, dioxolane, dithiane, dithiazine, dithiazole, dithiolane, furan, imidazole, imidazoline, imidazolidine, indole, indoline, indolizine, indazole, isoindole, isoquinoline, isoxazole, isothiazole, morpholine, napthyridine, oxazole, oxadiazole, oxathiazole, oxathiazolidine, oxazine, oxadiazine, phenazine, phenothiazine, phenoxazine, phthalazine, piperazine, piperidine, pteridine, purine, pyran, pyrazine, pyrazole, pyrazoline, pyrazolidine, pyridazine, pyridine, pyrimidine, pyrrole, pyrrolidine, pyrroline, quinoline, quinoxaline, quinazoline, quinolizine, tetrahydrofuran, tetrazine, tetrazole, thiophene, thiadiazine, thiadiazole, thiatriazole, thiazine, thiazole, thiomorpholine, thianaphthalene, thiopyran, triazine, triazole, and trithiane.

The term "halide" or "halogen" are used interchangeably and, as used herein mean a fluorine atom, a chlorine atom, a bromine atom, an iodine atom and the like, preferably a fluorine atom, a bromine atom or a chlorine atom, and more preferably a fluorine atom.

A haloalkyl group is preferably a "$C_{1-20}$ haloalkyl group", more preferably a "$C_{1-15}$ haloalkyl group", more preferably a "$C_{1-12}$ haloalkyl group", more preferably a "$C_{1-10}$ haloalkyl group", even more preferably a "$C_{1-8}$ haloalkyl group", even more preferably a "$C_{1-8}$ haloalkyl group" and is a $C_{1-20}$ alkyl, a $C_{1-15}$ alkyl, a $C_{1-12}$ alkyl, a $C_{1-10}$ alkyl, a $C_{1-8}$ alkyl, or a $C_{1-6}$ alkyl group, respectively, as described above substituted with at least one halogen atom, preferably 1, 2 or 3 halogen atom(s). Specifically, examples of "$C_{1-20}$ haloalkyl group" include fluoromethyl group, difluoromethyl group, trifluoromethyl group, fluoroethyl group, difluorethyl group, trifluoroethyl group, chloromethyl group, bromomethyl group, iodomethyl group and the like.

An alkoxy group is preferably a "$C_{1-20}$ alkoxy group", more preferably a "$C_{1-15}$ alkoxy group", more preferably a "$C_{1-12}$ alkoxy group", more preferably a "$C_{1-10}$ alkoxy group", even more preferably a "$C_{1-8}$ alkoxy group", even more preferably a "$C_{1-8}$ alkoxy group" and is an oxy group that is bonded to the previously defined $C_{1-20}$ alkyl, $C_{1-15}$ alkyl, $C_{1-12}$ alkyl, $C_{1-10}$ alkyl, $C_{1-8}$ alkyl, or $C_{1-6}$ alkyl group respectively. Specifically, examples of "$C_{1-20}$ alkoxy group" include methoxy group, ethoxy group, n-propoxy group, iso-propoxy group, n-butoxy group, iso-butoxy group, sec-butoxy group, tert-butoxy group, n-pentyloxy group, isopentyloxy group, sec-pentyloxy group, n-hexyloxy group, iso-hexyloxy group, n-hexyloxy group, n-heptyloxy group, n-octyloxy group, n-nonyloxy group, n-decyloxy group, n-undecyloxy group, n-dodecyloxy group, n-tridecyloxy group, n-tetradecyloxy group, n-pentadecyloxy group, n-hexadecyloxy group, n-heptadecyloxy group, n-octadecyloxy group, n-nonadecyloxy group, n-eicosyloxy group, 1,1-dimethylpropoxy group, 1,2-dimethylpropoxy group, 2,2-dimethylpropoxy group, 2-methylbutoxy group, 1-ethyl-2-methylpropoxy group, 1,1,2-trimethylpropoxy group, 1,1-dimethylbutoxy group, 1,2-dimethylbutoxy group, 2,2-dimethylbutoxy group, 2,3-dimethylbutoxy group, 1,3-dimethylbutoxy group, 2-ethylbutoxy group, 2-methylpentyloxy group, 3-methylpentyloxy group and the like.

An aryloxy group is preferably a "$C_{5-20}$ aryloxy group", more preferably a "$C_{6-12}$ aryloxy group", even more preferably a "$C_{6-10}$ aryloxy group" and is an oxy group that is bonded to the previously defined $C_{5-20}$ aryl, $C_{6-12}$ aryl, or $C_{6-10}$ aryl group respectively.

An alkylthio group is preferably a "$C_{1-20}$ alkylthio group", more preferably a "$C_{1-15}$ alkylthio group", more preferably a "$C_{1-12}$ alkylthio group", more preferably a "$C_{1-10}$ alkylthio group", even more preferably a "$C_{1-8}$ alkylthio group", even more preferably a "$C_{1-6}$ alkylthio group" and is a thio (—S—) group that is bonded to the previously defined $C_{1-20}$ alkyl, $C_{1-15}$ alkyl, $C_{1-12}$ alkyl, $C_{1-10}$ alkyl, $C_{1-8}$ alkyl, or $C_{1-6}$ alkyl group respectively.

An arylthio group is preferably a "$C_{5-20}$ arylthio group", more preferably a "$C_{6-12}$ arylthio group", even more preferably a "$C_{6-10}$ arylthio group" and is an thio (—S—) group that is bonded to the previously defined $C_{5-20}$ aryl, $C_{6-12}$ aryl, or $C_{6-10}$ aryl group respectively.

An alkylaryl group is preferably a "$C_{6-12}$ aryl $C_{1-20}$ alkyl group", more preferably a preferably a "$C_{6-12}$ aryl $C_{1-16}$ alkyl group", even more preferably a "$C_{6-12}$ aryl $C_{1-6}$ alkyl group" and is an aryl group as defined above bonded at any position to an alkyl group as defined above. The point of attachment of the alkylaryl group to a molecule may be via the alkyl portion and thus, preferably, the alkylaryl group is —$CH_2$-Ph or —$CH_2CH_2$-Ph. An alkylaryl group can also be referred to as "aralkyl".

A silyl group is preferably a group $Si(R_s)_3$, wherein each $R_s$ can be independently an aliphatic, heteroaliphatic, alicyclic, heteroalicyclic, aryl or heteroaryl group as defined above. In certain embodiments, each $R_s$ is independently an unsubstituted aliphatic, alicyclic or aryl. Preferably, each $R_s$ is an alkyl group selected from methyl, ethyl or propyl.

A silyl ether group is preferably a group $OSi(R_6)_3$ wherein each $R_6$ can be independently an aliphatic, heteroaliphatic, alicyclic, heteroalicyclic, aryl or heteroaryl group as defined above. In certain embodiments, each $R_6$ can be independently an unsubstituted aliphatic, alicyclic or aryl. Preferably, each $R_6$ is an optionally substituted phenyl or optionally substituted alkyl group selected from methyl, ethyl, propyl or butyl (such as n-butyl or tert-butyl (tertiary butyl)). Exemplary silyl ether groups include $OSi(Me)_3$, $OSi(Et)_3$, $OSi(Ph)_3$, $OSi(Me)_2$(tertiary butyl), $OSi$(tertiary butyl)$_3$ and $OSi(Ph)_2$(tertiary butyl).

A nitrile group (also referred to as a cyano group) is a group CN.

An imine group is a group —CRNR, preferably a group —$CHNR_7$ wherein $R_7$ is an aliphatic, heteroaliphatic, alicyclic, heteroalicyclic, aryl or heteroaryl group as defined above. In certain embodiments, $R_7$ is unsubstituted aliphatic, alicyclic or aryl. Preferably $R_7$ is an alkyl group selected from methyl, ethyl or propyl.

An acetylide group contains a triple bond —C≡C—$R_9$, preferably wherein $R_9$ can be hydrogen, an aliphatic, heteroaliphatic, alicyclic, heteroalicyclic, aryl or heteroaryl group as defined above. For the purposes of the invention when $R_9$ is alkyl, the triple bond can be present at any position along the alkyl chain. In certain embodiments, $R_9$ is unsubstituted aliphatic, alicyclic or aryl. Preferably $R_9$ is methyl, ethyl, propyl or phenyl.

An amino group is preferably —$NH_2$, —$NHR_{10}$ or —$N(R_{10})_2$ wherein $R_{10}$ can be an aliphatic, heteroaliphatic, alicyclic, heteroalicyclic, a silyl group, aryl or heteroaryl group as defined above. It will be appreciated that when the amino group is $N(R_{10})_2$, each $R_{10}$ group can be the same or different. In certain embodiments, each $R_{10}$ is independently an unsubstituted aliphatic, alicyclic, silyl or aryl. Preferably $R_{10}$ is methyl, ethyl, propyl, $SiMe_3$ or phenyl.

An amido group is preferably —$NR_{11}C(O)$— or —$C(O)$—$NR_{11}$— wherein $R_{11}$ can be hydrogen, an aliphatic, heteroaliphatic, alicyclic, heteroalicyclic, aryl or heteroaryl group as defined above. In certain embodiments, $R_{11}$ is unsubstituted aliphatic, alicyclic or aryl. Preferably $R_{11}$ is hydrogen, methyl, ethyl, propyl or phenyl. The amido group may be terminated by hydrogen, an aliphatic, heteroaliphatic, alicyclic, heteroalicyclic, aryl or heteroaryl group.

An ester group is preferably —$OC(O)R_{12}$— or —$C(O)OR_{12}$— wherein $R_{12}$ can be hydrogen, an aliphatic, heteroaliphatic, alicyclic, heteroalicyclic, aryl or heteroaryl group as defined above. In certain embodiments, $R_{12}$ is unsubstituted aliphatic, alicyclic or aryl. Preferably $R_{12}$ is hydrogen, methyl, ethyl, propyl or phenyl. The ester group may be terminated by hydrogen, an aliphatic, heteroaliphatic, alicyclic, heteroalicyclic, aryl or heteroaryl group.

A sulfoxide is preferably —$S(O)R_{13}$ and a sulfonyl group is preferably —$S(O)_2R_{13}$ wherein $R_{13}$ can be hydrogen, an aliphatic, heteroaliphatic, alicyclic, heteroalicyclic, aryl or heteroaryl group as defined above. In certain embodiments, $R_{13}$ is unsubstituted aliphatic, alicyclic or aryl. Preferably $R_{13}$ is hydrogen, methyl, ethyl, propyl or phenyl.

A carboxylate group is preferably —$OC(O)R_{14}$, wherein $R_{14}$ can be hydrogen, an aliphatic, heteroaliphatic, alicyclic, heteroalicyclic, aryl or heteroaryl group as defined above. In certain embodiments, $R_{14}$ is unsubstituted aliphatic, alicyclic or aryl. Preferably $R_{14}$ is hydrogen, methyl, ethyl, propyl, butyl (for example n-butyl, isobutyl or tert-butyl), phenyl, pentafluorophenyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, trifluoromethyl or adamantyl.

In an -alkyl$C(O)OR_{19}$ or -alkyl$C(O)R_{19}$ group, $R_{19}$ can be hydrogen, an aliphatic, heteroaliphatic, alicyclic, heteroalicyclic, aryl or heteroaryl group as defined above. In certain embodiments, $R_{19}$ is unsubstituted aliphatic, alicyclic or aryl. Preferably $R_{19}$ is hydrogen, methyl, ethyl, propyl, butyl (for example n-butyl, isobutyl or tert-butyl), phenyl, pentafluorophenyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, trifluoromethyl or adamantyl.

An acetamide is preferably $MeC(O)N(R_{15})_2$ wherein $R_{15}$ can be hydrogen, an aliphatic, heteroaliphatic, alicyclic, heteroalicyclic, aryl or heteroaryl group as defined above. In certain embodiments, $R_{15}$ is unsubstituted aliphatic, alicyclic or aryl. Preferably $R_{15}$ is hydrogen, methyl, ethyl, propyl or phenyl.

A phosphinate group is preferably a group —$OP(O)(R_{16})_2$ or —$P(O)(OR_{16})$ wherein each $R_{16}$ is independently selected from hydrogen, or an aliphatic, heteroaliphatic, alicyclic, heteroalicyclic, aryl or heteroaryl group as defined above. In certain embodiments, $R_{16}$ is aliphatic, alicyclic or aryl, which are optionally substituted by aliphatic, alicyclic, aryl or $C_{1-6}$alkoxy. Preferably $R_{16}$ is optionally substituted aryl or $C_{1-20}$ alkyl, more preferably phenyl optionally substituted by $C_{1-6}$alkoxy (preferably methoxy) or unsubstituted $C_{1-20}$alkyl (such as hexyl, octyl, decyl, dodecyl, tetradecyl, hexadecyl, stearyl).

A sulfinate group is preferably —OSOR$_{17}$ wherein $R_{17}$ can be hydrogen, an aliphatic, heteroaliphatic, haloaliphatic, alicyclic, heteroalicyclic, aryl or heteroaryl group as defined above. In certain embodiments, $R_{17}$ is unsubstituted aliphatic, alicyclic or aryl. Preferably $R_{17}$ is hydrogen, methyl, ethyl, propyl or phenyl.

A carbonate group is preferably OC(O)OR$_{18}$, wherein $R_{18}$ can be hydrogen, an aliphatic, heteroaliphatic, alicyclic, heteroalicyclic, aryl or heteroaryl group as defined above. In certain embodiments, $R_{18}$ is optionally substituted aliphatic, alicyclic or aryl. Preferably $R_{18}$ is hydrogen, methyl, ethyl, propyl, butyl (for example n-butyl, isobutyl or tert-butyl), phenyl, pentafluorophenyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, trifluoromethyl, cyclohexyl, benzyl or adamantyl.

It will be appreciated that where any of the above groups are present in a Lewis base G, one or more additional R groups may be present, as appropriate, to complete the valency. For example, in the context of an amino group, an additional R group may be present to give RNHR$_{10}$, wherein R is hydrogen, an optionally substituted aliphatic, heteroaliphatic, alicyclic, heteroalicyclic, aryl or heteroaryl group as defined above. Preferably, R is hydrogen or aliphatic, alicyclic or aryl.

Any of the aliphatic, heteroaliphatic, alicyclic, heteroalicyclic, aryl, heteroaryl, haloalkyl, alkoxy, aryloxy, alkylthio, arylthio, alkylaryl, silyl, silyl ether, ester, sulfoxide, sulfonyl, carboxylate, carbonate, imine, acetylide, amino, phosphinate, sulfonate or amido groups wherever mentioned in the definitions above, may optionally be substituted by halogen, hydroxy, nitro, carboxylate, carbonate, alkoxy, aryloxy, alkylthio, arylthio, heteroaryloxy, alkylaryl, amino, amido, imine, nitrile, silyl, silyl ether, ester, sulfoxide, sulfonyl, acetylide, phosphinate, sulfonate or optionally substituted aliphatic, heteroaliphatic, alicyclic, heteroalicyclic, aryl or heteroaryl groups (for example, optionally substituted by halogen, hydroxy, nitro, carbonate, alkoxy, aryloxy, alkylthio, arylthio, amino, imine, nitrile, silyl, sulfoxide, sulfonyl, phosphinate, sulfonate or acetylide).

It will be appreciated that although in formula (I), the groups X and G are illustrated as being associated with a single $M_1$ or $M_2$ metal centre, one or more X and G groups may form a bridge between the $M_1$ and $M_2$ metal centres.

For the purposes of the present invention, the epoxide substrate is not limited. The term epoxide therefore relates to any compound comprising an epoxide moiety. Examples of epoxides which may be used in the present invention include, but are not limited to, cyclohexene oxide, styrene oxide, propylene oxide, butylene oxide, substituted cyclohexene oxides (such as limonene oxide, $C_{10}H_{16}O$ or 2-(3, 4-epoxycyclohexyl)ethyltrimethoxysilane, $C_{11}H_{22}O$), alkylene oxides (such as ethylene oxide and substituted ethylene oxides) or substituted or unsubstituted oxiranes (such as oxirane, epichlorohydrin, 2-(2-methoxyethoxy)methyl oxirane (MEMO), 2-(2-(2-methoxyethoxy)ethoxy)methyl oxirane (ME2MO), 2-(2-(2-(2-methoxyethoxy)ethoxy)ethoxy) methyl oxirane (ME3MO), 1,2-epoxybutane, glycidyl ethers), vinyl-cyclohexene oxide, 3-phenyl-1,2-epoxypropane, 1,2- and 2,3-epoxybutane, isobutylene oxide, cyclopentene oxide, 2,3-epoxy-1,2,3,4-tetrahydronaphthalene, indene oxide, and functionalized 3,5-dioxaepoxides. Examples of functionalized 3,5-dioxaepoxides include:

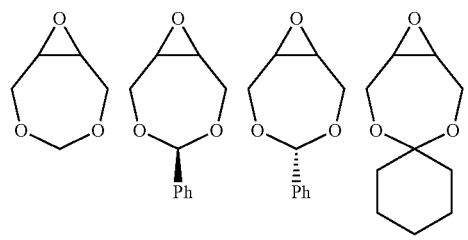

The epoxide moiety may be a glycidyl ether, glycidyl ester or glycidyl carbonate. Examples of glycidyl ethers, glycidyl esters and glycidyl carbonates include:

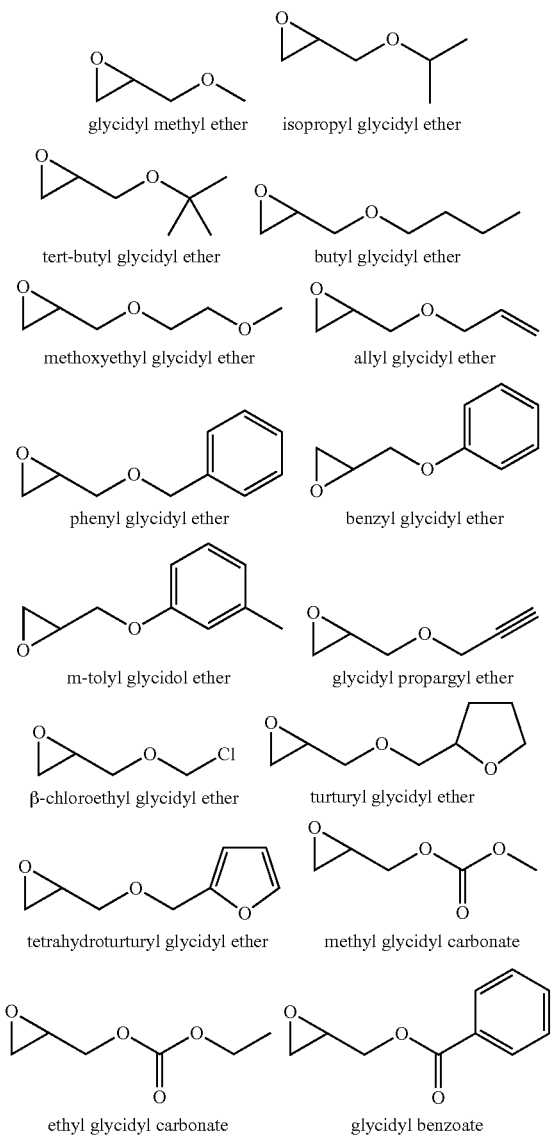

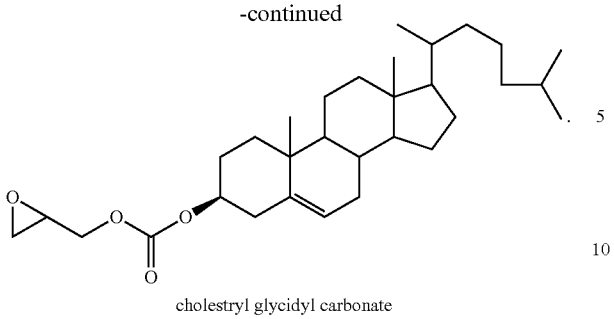

cholestryl glycidyl carbonate

The epoxide substrate may contain more than one epoxide moiety, i.e. it may be a bis-epoxide, a tris-epoxide, or a multi-epoxide containing moiety. Examples of compounds including more than one epoxide moiety include bisphenol A diglycidyl ether and 3,4-epoxycyclohexylmethyl 3,4-epoxycyclohexanecarboxylate. It will be understood that reactions carried out in the presence of one or more compounds having more than one epoxide moiety may lead to cross-linking in the resulting polymer.

The skilled person will appreciate that the epoxide can be obtained from "green" or renewable resources. The epoxide may be obtained from a (poly)unsaturated compound, such as those deriving from a fatty acid and/or terpene, obtained using standard oxidation chemistries.

The epoxide moiety may contain —OH moieties, or protected —OH moieties. The —OH moieties may be protected by any suitable protecting group. Suitable protecting groups include methyl or other alkyl groups, benzyl, allyl, tert-butyl, tetrahydropyranyl (THP), methoxymethyl (MOM), acetyl (C(O)alkyl), benzolyl (C(O)Ph), dimethoxytrityl (DMT), methoxyethoxymethyl (MEM), p-methoxybenzyl (PMB), trityl, silyl (such as trimethylsilyl (TMS), t-Butyldimethylsilyl (TBDMS), t-Butyldiphenylsilyl (TBDPS), tri-iso-propylsilyloxymethyl (TOM), and tri-isopropylsilyl (TIPS)), (4-methoxyphenyl)diphenylmethyl (MMT); tetrahydrofuranyl (THF), and tetrahydropyranyl (THP).

The epoxide preferably has a purity of at least 98%, more preferably >99%.

It will be understood that the term "an epoxide" is intended to encompass one or more epoxides. In other words, the term "an epoxide" refers to a single epoxide, or a mixture of two or more different epoxides. For example, the epoxide substrate may be a mixture of ethylene oxide and propylene oxide, a mixture of cyclohexene oxide and propylene oxide, a mixture of ethylene oxide and cyclohexene oxide, or a mixture of ethylene oxide, propylene oxide and cyclohexene oxide.

The skilled person will also understand that substituted and unsubstituted oxetanes can be used in place of, and in addition to, the epoxides of the second aspect of the invention. Suitable oxetanes include unsubstituted or substituted oxetanes (preferably substituted at the 3-position by halogen, alkyl (unsubstituted or substituted by —OH or halogen), amino, hydroxyl, aryl (e.g. phenyl), alkylaryl (e.g. benzyl)). Exemplary oxetanes include oxetane, 3-ethyl-3-oxetanemethanol, oxetane-3-methanol, 3-methyl-3-oxetanemethanol, 3-methyloxetane, 3-ethyloxetane, etc.

The term anhydride relates to any compound comprising an anhydride moiety in a ring system (i.e. a cyclic anhydride). Preferably, the anhydrides which are useful in the present invention have the following formula:

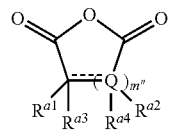

Wherein m" is 1, 2, 3, 4, 5, or 6 (preferably 1 or 2), each $R^{a1}$, $R^{a2}$, $R^{a3}$ and $R^{a4}$ is independently selected from hydrogen, halogen, hydroxyl, nitro, alkoxy, aryloxy, heteroaryloxy, amino, alkylamino, imine, nitrile, acetylide, carboxylate or optionally substituted aliphatic, heteroaliphatic, alicyclic, heteroalicyclic, aryl, heteroaryl, alkylaryl or alkylheteroaryl; or two or more of $R^{a1}$, $R^{a2}$, $R^{a3}$ and $R^{a4}$ can be taken together to form a saturated, partially saturated or unsaturated 3 to 12 membered, optionally substituted ring system, optionally containing one or more heteroatoms, or can be taken together to form a double bond. Each Q is independently C, O, N or S, preferably C, wherein $R^{a3}$ and $R^{a4}$ are either present, or absent, and ------ can either be $=$ or —, according to the valency of Q. It will be appreciated that when Q is C, and ------ is, $=$, $R^{a3}$ and $R^{a4}$ (or two $R^{a4}$ on adjacent carbon atoms) are absent. The skilled person will appreciate that the anhydrides may be obtained from "green" or renewable resources. Preferable anhydrides are set out below.

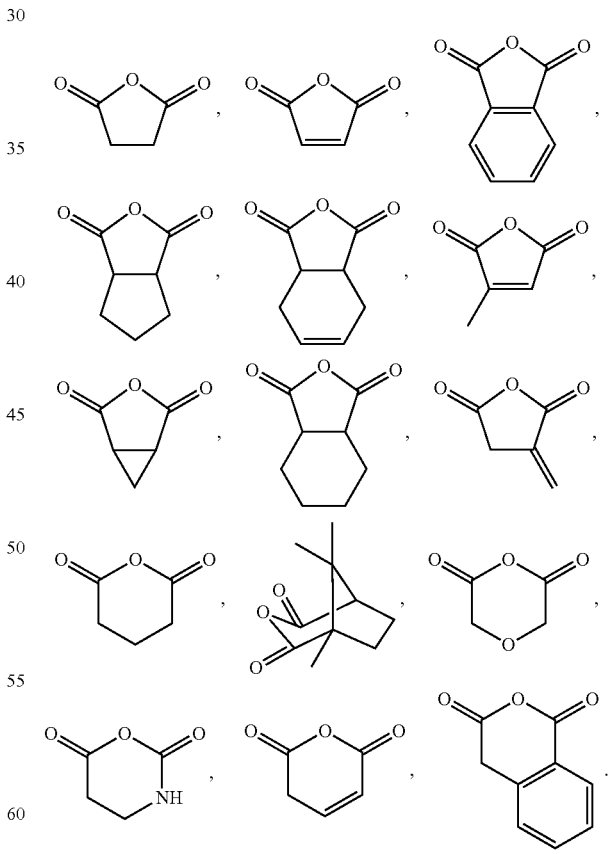

The term lactone relates to any cyclic compound comprising a —C(O)O— moiety in the ring. Preferably, the lactones which are useful in the present invention have the following formula:

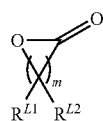

Wherein m is 1 to 20 (e.g. 1, 2, 3, 4, 5, 6, 7, 8, 9, 10, 11, 12, 13, 14, 15, 16, 17, 18, 19 or 20), preferably 2, 4, or 5; and $R^{L1}$ and $R^{L2}$ are independently selected from hydrogen, halogen, hydroxyl, nitro, alkoxy, aryloxy, heteroaryloxy, amino, alkylamino, imine, nitrile, acetylide, carboxylate or optionally substituted aliphatic, heteroaliphatic, alicyclic, heteroalicyclic, aryl, heteroaryl, alkylaryl or alkylheteroaryl. Two or more of $R^{L1}$ and $R^{L2}$ can be taken together to form a saturated, partially saturated or unsaturated 3 to 12 membered, optionally substituted ring system, optionally containing one or more heteroatoms. When m is 2 or more, the $R^{L1}$ and $R^{L2}$ on each carbon atom may be the same or different. Preferably $R^{L1}$ and $R^{L2}$ are selected from hydrogen or alkyl. Preferably, the lactone has the following structure:

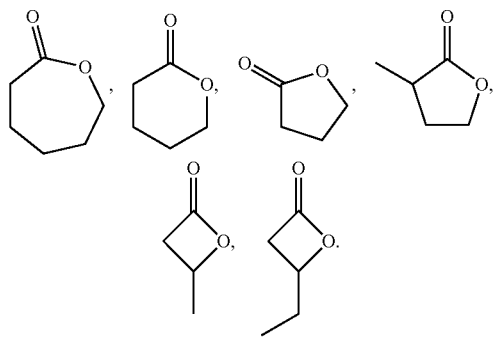

The term lactide is a cyclic compound containing two ester groups. Preferably, the lactides which are useful in the present invention have the following formula:

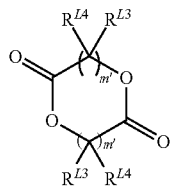

Wherein m' is 1, 2, 3, 4, 5, 6, 7, 8, 9 or 10, (preferably 1 or 2, more preferably, 1) and $R^{L3}$ and $R^{L4}$ are independently selected from hydrogen, halogen, hydroxyl, nitro, alkoxy, aryloxy, heteroaryloxy, amino, alkylamino, imine, nitrile, acetylide, carboxylate or optionally substituted aliphatic, heteroaliphatic, alicyclic, heteroalicyclic, aryl, heteroaryl, alkylaryl or alkylheteroaryl. Two or more of $R^{L3}$ and $R^{L4}$ can be taken together to form a saturated, partially saturated or unsaturated 3 to 12 membered, optionally substituted ring system, optionally containing one or more heteroatoms, When m' is 2 or more, the $R^{L3}$ and $R^{L4}$ on each carbon atom may be the same or different or one or more $R^{L3}$ and $R^{L4}$ on adjacent carbon atoms can be absent, thereby forming a double or triple bond. It will be appreciated that while the compound has two moieties represented by $(-CR^{L3}R^{L4})_{m'}$, both moieties will be identical. Preferably, m' is 1, $R^{L4}$ is H, and $R^{L3}$ is H, hydroxyl or a $C_{1-6}$alkyl, preferably methyl. The stereochemistry of the moiety represented by $(-CR^{L3}R^{L4})_{m'}$ can either be the same (for example RR-lactide or SS-lactide), or different (for example, meso-lactide). The lactide may be a racemic mixture, or may be an optically pure isomer. Preferably, the lactide has the following formula:

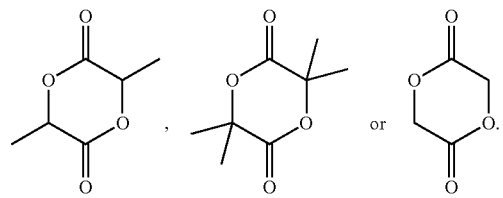

The term "lactone and/or lactide" used herein encompasses a lactone, a lactide and a combination of a lactone and a lactide. Preferably, the term "lactone and/or lactide" means a lactone or a lactide.

Preferred optional substituents of the groups $R^{a1}$, $R^{a2}$, $R^{a3}$, $R^{a4}$, $R^{L1}$, $R^{L2}$, $R^{L3}$ and $R^{L4}$ include halogen, nitro, hydroxyl, unsubstituted aliphatic, unsubstituted heteroaliphatic unsubstituted aryl, unsubstituted heteroaryl, alkoxy, aryloxy, heteroaryloxy, amino, alkylamino, imine, nitrile, acetylide, and carboxylate.

DETAILED DESCRIPTION

In the first aspect of the invention, there is provided a catalyst of formula (I):

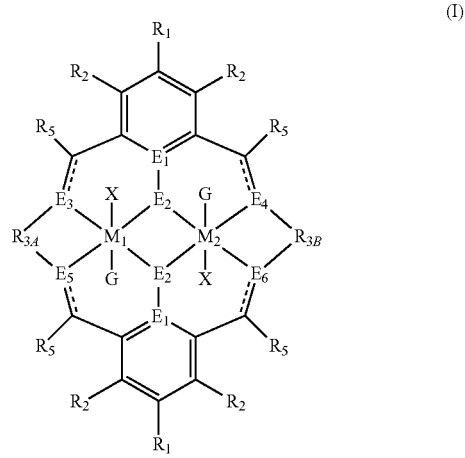

wherein:
$M_1$ and $M_2$ are independently selected from Zn(II), Cr(II), Co(II), Cu(II), Mn(II), Mg(II), Ni(II), Fe(II), Ti(II), V(II), Cr(III)-X, Co(III)-X, Ni(III)-X, Mn(III)-X, Fe(III)-X, Ca(II), Ge(II), Al(III)-X, Ti(III)-X, V(III)-X, Ge(IV)-$(X)_2$ or Ti(IV)-$(X)_2$;
$R_1$ and $R_2$ are independently selected from hydrogen, halide, a nitro group, a nitrile group, an imine, an amine, an ether group, a silyl group, a silyl ether group, a sulfoxide group, a sulfonyl group, a sulfinate group or an acetylide group or an optionally substituted alkyl, alkenyl, alkynyl, haloalkyl, aryl, heteroaryl, alkoxy, aryloxy, alkylthio, arylthio, alicyclic or heteroalicyclic group;

$R_{3A}$ and $R_{3B}$ are independently selected from optionally substituted alkylene, alkenylene, alkynylene, heteroalkylene, heteroalkenylene, heteroalkynylene, arylene, heteroarylene or cycloalkylene, wherein alkylene, alkenylene, alkynylene, heteroalkylene, heteroalkenylene and heteroalkynylene, may optionally be interrupted by aryl, heteroaryl, alicyclic or heteroalicyclic;

$R_5$ is independently selected from H, or optionally substituted aliphatic, heteroaliphatic, alicyclic, heteroalicyclic, aryl, heteroaryl, alkylheteroaryl or alkylaryl;

$E_1$ is C, $E_2$ is O, S or NH or $E_1$ is N and $E_2$ is O;

$E_3$, $E_4$, $E_5$ and $E_6$ are each independently selected from N, $NR_4$, O and S, wherein when any of $E_3$, $E_4$, $E_5$ or $E_6$ are N, ===== is ═, and wherein when any of $E_3$, $E_4$, $E_5$ or $E_6$ are $NR_4$, O or S, ===== is —; $R_4$ is independently selected from H, or optionally substituted aliphatic, heteroaliphatic, alicyclic, heteroalicyclic, aryl, heteroaryl, alkylheteroaryl or alkylaryl;

X is independently selected from $OC(O)R^x$, $OSO_2R^x$, $OSOR^x$, $OSO(R^x)_2$, $S(O)R^x$, $OR^x$, phosphinate, halide, nitrate, hydroxyl, carbonate, amino, amido or optionally substituted aliphatic, heteroaliphatic, alicyclic, heteroalicyclic, aryl or heteroaryl;

$R_x$ is independently hydrogen, or optionally substituted aliphatic, haloaliphatic, heteroaliphatic, alicyclic, heteroalicyclic, aryl, alkylaryl or heteroaryl; and G is absent or independently selected from a neutral or anionic donor ligand which is a Lewis base;

and wherein:
i) $R_{3A}$ is different from $R_{3B}$; and/or
ii) at least one occurrence of $E_3$, $E_4$, $E_5$ and $E_6$ is different to a remaining occurrence of $E_3$, $E_4$, $E_5$ and $E_6$.

Preferably, each of the occurrences of the groups $R_1$ and $R_2$ may be the same or different. Preferably $R_1$ and $R_2$ are independently selected from hydrogen, halide, amino, nitro, sulfoxide, sulfonyl, sulfinate, silyl, silyl ether and an optionally substituted alkyl, alkenyl, aryl, heteroaryl, alkoxy, aryloxy or alkylthio. Preferably each occurrence of $R_2$ is the same. Preferably, each occurrence of $R_2$ is the same, and is hydrogen.

Even more preferably, $R_2$ is hydrogen and $R_1$ is independently selected from hydrogen, halide, amino, nitro, sulfoxide, sulfonyl, sulfinate, silyl ether and optionally substituted alkyl, alkenyl, aryl, heteroaryl, alkoxy, aryloxy, alkylthio, arylthio, such as hydrogen, $C_{1-6}$alkyl (e.g. haloalkyl), alkoxy, aryl, halide, nitro, sulfonyl, silyl and alkylthio, for example, tertiary butyl, isopropyl, methyl, methyloxy, hydrogen, nitro, dimethylsulfoxide, trialkylsilyl for example triethylsilyl, silyl ether, halogen or phenyl. Most preferably $R_1$ is tertiary butyl and $R_2$ is hydrogen.

Each occurrence of $R_1$ can be the same or different, and $R_1$ and $R_2$ can be the same or different. Preferably each occurrence of $R_1$ is the same. Preferably, each occurrence of $R^1$ is the same, and each occurrence of $R_2$ is the same, and $R_1$ is different to $R_2$. The skilled person will appreciate that when each occurrence of $R_1$ is different, this adds to the asymmetry of the catalyst.

It will be appreciated that the groups $R_{3A}$ and $R_{3B}$ can be a disubstituted alkyl, alkenyl, alkynyl, heteroalkyl, heteroalkenyl or heteroalkynyl group which may optionally be interrupted by an aryl, heteroaryl, alicyclic or heteroalicyclic group, or may be a disubstituted aryl or cycloalkyl group which acts as a bridging group between two nitrogen centres in the catalyst of formula (I). Thus, where $R_{3A}$ or $R_{3B}$ is an alkylene group, such as dimethylpropylene, the $R_{3A}$ or $R_{3B}$ group has the structure —$CH_2$—$C(CH_3)_2$—$CH_2$—. The definitions of the alkyl, aryl, cycloalkyl etc groups set out above therefore also relate respectively to the alkylene, arylene, cycloalkylene etc groups set out for $R_{3A}$ or $R_{3B}$, and may be optionally substituted. Exemplary options for $R_{3A}$ and $R_{3B}$ include ethylene, 2,2-dimethylpropylene, 2,2-fluoropropylene, propylene, butylene, phenylene, cyclohexylene or biphenylene, more preferably 2,2-dimethylpropylene, 2,2-fluoropropylene, propylene, cyclohexylene or phenylene. When $R_{3A}$ or $R_{3B}$ is cyclohexylene, it can be the racemic, RR- or SS-forms. Preferably $R_{3A}$ or $R_{3B}$ are selected from ethylene, propylene, a substituted propylene, such as 2,2-di(alkyl)propylene, phenylene, or cyclohexylene, more preferably $R_{3A}$ or $R_{3B}$ are 2,2-di(methyl)propylene.

When each occurrence of $E_3$, $E_4$, $E_5$ and $E_6$ is the same, $R_{3A}$ is different to $R_{3B}$. It will also be appreciated that when at least one occurrence of $E_3$, $E_4$, $E_5$ and $E_6$ is different to a remaining occurrence of $E_3$, $E_4$, $E_5$ and $E_6$, $R_{3A}$ can be the same as, or different to $R_{3B}$.

Preferably, when $R_{3A}$ is different to $R_{3B}$, $R_{3A}$ can be optionally substituted alkylene (for example, optionally substituted propylene, e.g. 2,2-dimethylpropylene, 2,2-fluoropropylene or propylene), or optionally substituted cycloalkylene (such as cyclohexylene), and $R_{3B}$ can be optionally substituted arylene (such as phenylene or biphenylene), or optionally substituted alkylene (for example, optionally substituted propylene, e.g. 2,2-dimethylpropylene, 2,2-fluoropropylene, ethylene or propylene).

In a first preferred embodiment, $R_{3A}$ is 2,2-dimethylpropylene, and $R_{3B}$ is phenylene.

In a second preferred embodiment, $R_{3A}$ is a disubstituted cycloalkylene which acts as a bridging group between two nitrogen centres in the catalyst of formula (I), and $R_{3B}$ is 2,2-dimethylpropylene.

In a third preferred embodiment, $R_{3A}$ is 2,2-dimethylpropylene, and $R_{3B}$ is propylene or ethylene.

In a fourth preferred embodiment, $R_{3A}$ is propylene, and $R_{3B}$ is 2,2-dimethylpropylene. $E_3$, $E_4$, $E_5$ and $E_6$ are each independently selected from N, $NR_4$, O or S. The skilled person will understand that when any of $E_3$, $E_4$, $E_5$ or $E_6$ are N, ===== is ═. It will also be understood that when any of $E_3$, $E_4$, $E_5$ or $E_6$ are $NR_4$, O or S, ===== is —.

When $R_{3A}$ and $R_{3B}$ are the same, at least one occurrence of $E_3$, $E_4$, $E_5$ or $E_6$ is different to a remaining occurrence of $E_3$, $E_4$, $E_5$ and $E_6$.

Preferably when at least one occurrence of $E_3$, $E_4$, $E_5$ or $E_6$ is different to a remaining occurrence of $E_3$, $E_4$, $E_5$ and $E_6$, each $E_3$, $E_4$, $E_5$ and $E_6$ is $NR_4$, but at least one of the $R_4$ groups is different from a remaining $R_4$ groups.

Alternatively, when at least one occurrence of $E_3$, $E_4$, $E_5$ or $E_6$ is different to a remaining occurrence of $E_3$, $E_4$, $E_5$ and $E_6$, and at least one occurrence of $E_3$, $E_4$, $E_5$ or $E_6$ is $NR_4$, at least one of the remaining $E_3$, $E_4$, $E_5$ and $E_6$ groups is selected from N, O or S.

It will be understood that when $R_{3A}$ is different to $R_{3B}$, each $E_3$, $E_4$, $E_5$ and $E_6$ may be the same or different.

Preferably, when $R_{3A}$ is different to $R_{3B}$, each $E_3$, $E_4$, $E_5$ and $E_6$ are the same. When each of $E_3$, $E_4$, $E_5$ and $E_6$ are the same, preferably each of $E_3$, $E_4$, $E_5$ and $E_6$ are $NR_4$, more preferably each of $E_3$, $E_4$, $E_5$ and $E_6$ are NH.

It will be understood that $E_3$ and $E_5$ may be the same, $E_3$ and $E_4$ may be the same, $E_4$ and $E_6$ may be the same, $E_4$ and $E_5$ may be the same, $E_5$ and $E_6$ may be the same, and/or $E_3$ and $E_6$ may be the same. It is preferred that $E_3$ and $E_5$ are the same, and $E_4$ and $E_6$ are the same, and $E_3$ and $E_5$ are different to $E_4$ and $E_6$, preferably $E_3$ and $E_5$ are S or O and $E_4$ and $E_6$ are N or $NR_4$ (such as NH). Alternatively, $E_3$ and $E_4$ can be the same, and $E_5$ and $E_6$ can be the same, and $E_3$ and $E_4$ are different to $E_5$ and $E_6$, preferably $E_3$ and $E_4$ are S and $E_5$ and $E_6$ are N or $NR_4$ (such as NH).

Preferably each $R_4$ is independently selected from hydrogen, and an optionally substituted alkyl, alkenyl, alkynyl, aryl, heteroalkyl, heteroalkenyl, heteroalkynyl or heteroaryl. Preferably, at least one $R_4$ is hydrogen. At least one $R_4$ may be different to a remaining $R_4$ group/s. When each $R_4$ is the same, it is preferably selected from hydrogen, and an optionally substituted alkyl, alkenyl, alkynyl, aryl, heteroalkyl, heteroalkenyl, heteroalkynyl or heteroaryl. Exemplary options for $R_4$ include hydrogen, methyl, ethyl, n-propyl, n-butyl, isopropyl, tertiary butyl, benzyl, phenyl, -alkyl-C(O)—$OR_{19}$ (as defined hereinabove for example methyl propanoate), alkyl nitrile of the formula -alkyl-C≡N or alkyl ketone/aldehyde of the formula alkyl-C(O)—$R_{19}$. A further exemplary option is methylpyridine.

Preferably each $E_3$, $E_4$, $E_5$ and $E_6$ is $NR_4$, and one of the $R_4$ groups is different, preferably $E_4$ is different. More preferably one of the $R_4$ groups is selected from an optionally substituted alkyl or heteroalkyl. Still more preferably one of the $R_4$ groups is selected from methyl, ethyl, propyl, butyl or -alkyl-C(O)—$OR_{19}$ as defined hereinabove, for example methyl propanoate. Preferably the remaining $R_4$ groups are hydrogen.

Preferably each $E_3$, $E_4$, $E_5$ and $E_6$ is $NR_4$, and two of the $R_4$ groups are different, preferably $E_3$ and $E_5$ are different or $E_4$ and $E_5$ are different. More preferably two of the $R_4$ groups are selected from an optionally substituted alkyl or heteroalkyl. Still more preferably two of the $R_4$ groups are selected from methyl, ethyl, propyl, butyl or -alkyl-C(O)—$OR_{19}$ as defined hereinabove, for example methyl propanoate. Preferably the remaining $R_4$ groups are hydrogen.

Preferably two of $E_3$, $E_4$, $E_5$ and $E_6$ are $NR_4$, and two of $E_3$, $E_4$, $E_5$ and $E_6$ are N. More preferably two of $E_3$, $E_4$, $E_5$ and $E_6$ are NH and two of $E_3$, $E_4$, $E_5$ and $E_6$ are N. Still more preferably, $E_4$ and $E_6$ are NH and $E_3$ and $E_5$ are N, or $E_3$ and $E_5$ are NH and $E_4$ and $E_6$ are N.

Preferably two of $E_3$, $E_4$, $E_5$ and $E_6$ are S, and two of $E_3$, $E_4$, $E_5$ and $E_6$ are $NR_4$. More preferably two of $E_3$, $E_4$, $E_5$ and $E_6$ are S, and two of $E_3$, $E_4$, $E_5$ and $E_6$ are NH. Still more preferably $E_3$ and $E_5$ are S, and, $E_4$ and $E_6$ are NH.

Preferably each $R_5$ is independently selected from hydrogen, and optionally substituted aliphatic or aryl. More preferably, each $R_5$ is independently selected from hydrogen, and optionally substituted alkyl or aryl. Even more preferably, each $R_5$ is the same, and is selected from hydrogen, and optionally substituted alkyl or aryl. Exemplary $R_5$ groups include hydrogen, methyl, ethyl, phenyl and trifluoromethyl, preferably hydrogen, methyl or trifluoromethyl. Even more preferably, each $R_5$ is hydrogen.

Preferably both occurrences of $E_1$ are C and both occurrences of $E_2$ are the same, and selected from O, S or NH. Even more preferably, both occurrences of $E_1$ are C and both occurrences of $E_2$ are O.

Each X is independently selected from $OC(O)R^x$, $OSO_2R^x$, $OS(O)R^x$, $OSO(R^x)_2$, $S(O)R^x$, $OR^x$, phosphinate, halide, nitro, hydroxyl, carbonate, amino, amido and optionally substituted aliphatic, heteroaliphatic (for example silyl), alicyclic, heteroalicyclic, aryl or heteroaryl. Preferably each X is independently $OC(O)R^x$, $OSO_2R^x$, $OS(O)R^x$, $OSO(R^x)_2$, $S(O)R^x$, $OR^x$, halide, nitrate, hydroxyl, carbonate, amino, nitro, amido, alkyl (e.g. branched alkyl), heteroalkyl, (for example silyl), aryl or heteroaryl. In particularly preferred embodiments, each X is independently $OC(O)R^x$, $OR^x$, halide, carbonate, amino, nitro, alkyl, aryl, heteroaryl, phosphinate or $OSO_2R^x$. Preferred optional substituents for when X is aliphatic, heteroaliphatic, alicyclic, heteroalicyclic, aryl or heteroaryl include halogen, hydroxyl, nitro, cyano, amino, or substituted or unsubstituted aliphatic, heteroaliphatic, alicyclic, heteroalicyclic, aryl or heteroaryl. Each X may be the same or different and preferably each X is the same.

$R^x$ is independently hydrogen, or optionally substituted aliphatic, haloaliphatic, heteroaliphatic, alicyclic, heteroalicyclic, aryl, alkylaryl or heteroaryl. Preferably, $R^x$ is alkyl, alkenyl, alkynyl, heteroalkyl, aryl, heteroaryl or alkylaryl. Preferred optional substitutents for $R^x$ include halogen, hydroxyl, cyano, nitro, amino, alkoxy, alkylthio, or substituted or unsubstituted aliphatic, heteroaliphatic, alicyclic, heteroalicyclic, aryl or heteroaryl (e.g. optionally substituted alkyl, aryl, or heteroaryl).

Exemplary options for X include acetate, trifluoroacetyl, octanoate, carbonate, 2-ethylhexanoate, cyclohexylbutyrate, dimethyl sulfonyl, ethyl, methyl, methyloxy, isopropyloxy, tertiary butyloxy, halogen (such as chloride, bromide, iodide, fluoride), diisopropylamide or bis(trimethylsilyl)amide, phenoxy, n-butyloxy, salicylate, dioctyl phosphinate, diphenyl phosphinate etc. Preferably X is acetate.

$M_1$ and $M_2$ are independently selected from Zn(II), Cr(III), Cr(II), Co(III), Co(II), Cu(II), Ni(II), Ni(III), Mn(III), Mn(II), Mg(II), Fe(II), Fe(III), Ca(II), Ge(II), Ti(II), Al(III), Ti(III), V(II), V(III), Ge(IV) or Ti(IV). Preferably, $M_1$ and $M_2$ are independently selected from Zn(II), Cr(III), Co(II), Mn(II), Mg(II), Ni(II), Ni(III), Fe(II) and Fe(III), even more preferably, $M_1$ and $M_2$ are independently selected from Zn(II), Cr(III), Co(II), Mn(II), Ni(II), Ni(III), Mg(II), Fe(II), and Fe(III), and even more preferably, $M_1$ and $M_2$ are independently selected from Zn(II), Ni(II), Ni(III) and Mg(II). Still more preferably $M_1$ and $M_2$ are independently selected from Ni(II), Ni(III), or Mg(II). Preferably $M_1$ and $M_2$ are the same. Most preferably $M_1$ and $M_2$ are the same and are Ni(II) or Mg(II).

It will be appreciated that when $M_1$ or $M_2$ is Cr(III), Co(III), Mn(III), Ni(III) or Fe(III), the catalyst of formula (I) will contain an additional X group co-ordinated to the metal centre, wherein X is as defined above. It will also be appreciated that when $M_1$ or $M_2$ is Ge(IV) or Ti(IV), the catalyst of formula (III) will contain two additional X group co-ordinated to the metal centre, wherein X is as defined above. It will be understood that when $M_1$ or $M_2$ is Ge(IV) or Ti(IV), both G may be absent.

When G is not absent, it is a group which is capable of donating a lone pair of electrons (i.e. a Lewis base). G can be a nitrogen-containing Lewis base. Each G may be neutral or negatively charged. If G is negatively charged, then one or more positive counterions will be required to balance out the charge of the complex. Suitable positive counterions include group 1 metal ions ($Na^+$, $K^+$, etc), group 2 metal ions ($Mg^{2+}$, $Ca^{2+}$, etc), imidazolium ions, a positively charged optionally substituted heteroaryl, heteroaliphatic or heteroalicyclic group, ammonium ions (i.e. $N(R^{12})_4^+$), iminium ions (i.e. $(R^{12})_2C=N(R^{12})_2^+$, such as bis(triphenylphosphine)iminium ions) or phosphonium ions ($P(R^{12})_4^+$), wherein each $R^{12}$ is independently selected from hydrogen or optionally substituted aliphatic, heteroaliphatic, alicyclic, heteroalicyclic, aryl or heteroaryl. Exemplary counterions include $[H—B]^+$ wherein B is selected from triethylamine, 1,8-diazabicyclo[5.4.0]undec-7-ene and 7-methyl-1,5,7-triazabicyclo[4.4.0]dec-5-ene.

G is preferably independently selected from an optionally substituted heteroaliphatic group, an optionally substituted heteroalicyclic group, an optionally substituted heteroaryl group, a halide, hydroxide, hydride, a carboxylate and water. More preferably, G is independently selected from water, an alcohol (e.g methanol), a substituted or unsubstituted heteroaryl (imidazole, methyl imidazole (for example, N-methyl imidazole), pyridine, 4-dimethylaminopyridine, pyrrole, pyrazole, etc), an ether (dimethyl ether, diethylether, cyclic ethers, etc), a thioether, carbene, a phosphine, a phosphine oxide, a substituted or unsubstituted heteroalicyclic (morpholine, piperidine, tetrahydrofuran, tetrahydrothiophene, etc), an amine, an alkyl amine trimethylamine, triethylamine, etc), acetonitrile, an ester (ethyl acetate, etc), an acetamide (dimethylacetamide, etc), a sulfoxide (dimethylsulfoxide, etc), a carboxylate, a hydroxide, hydride, a halide, a nitrate, a sulfonate, etc. It will be appreciated that one or both instances of G can be independently selected from optionally substituted heteroaryl, optionally substituted heteroaliphatic, optionally substituted heteroalicyclic, halide, hydroxide, hydride, an ether, a thioether, carbene, a phosphine, a phosphine oxide, an amine, an alkyl amine, acetonitrile, an ester, an acetamide, a sulfoxide, a carboxylate, a nitrate or a sulfonate. G may be a halide; hydroxide; hydride; water; a heteroaryl, heteroalicyclic or carboxylate group which are optionally substituted by alkyl, alkenyl, alkynyl, alkoxy, halogen, hydroxyl, nitro or nitrile. Preferably, G is independently selected from halide; water; a heteroaryl optionally substituted by alkyl (e.g. methyl, ethyl etc), alkenyl, alkynyl, alkoxy (preferably methoxy), halogen, hydroxyl, nitro or nitrile. It will be understood that one or both instances of G may be negatively charged (for example, halide). Preferably, one or both instances of G is an optionally substituted heteroaryl. Exemplary G groups include chloride, bromide, pyridine, methylimidazole (for example N-methyl imidazole) and dimethylaminopyridine (for example, 4-methylaminopyridine).

It will be appreciated that when a G group is present, the G group may be associated with a single M metal centre as shown in formula (I), or the G group may be associated with both metal centres and form a bridge between the two metal centres, as shown below in formula (Ia):

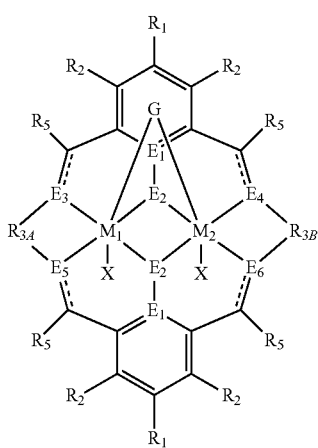

(Ia)

Wherein $R_1$, $R_2$, $R_{3A}$, $R_{3B}$, $R_4$, $E_1$, $E_2$, $E_3$, $E_4$, $E_5$, $E_6$, $R_5$, M, G and X, are as defined for formula (I). It will also be appreciated that X may form a bridge between the two metal centres.

The skilled person will understand that, in the solid state, the catalysts of the first aspect may be associated with solvent molecules such as water, or alcohol (e.g. methanol or ethanol). It will be appreciated that the solvent molecules may be present in a ratio of less than 1:1 relative to the molecules of catalyst of the first aspect (i.e. 0.2:1, 0.25:1, 0.5:1), in a ratio of 1:1, relative to the molecules of catalyst of the first aspect, or in a ratio of greater than 1:1, relative to the molecules of catalyst of the first aspect.

The skilled person will understand that, in the solid state, the catalysts of the first aspect may form aggregates. For example, the catalyst of the first aspect may be a dimer, a trimer, a tetramer, a pentamer, or higher aggregate.

It will be appreciated that the preferred features described above for the catalyst of the first aspect may be present in combination mutatis mutandis.

For example, each occurrence of $R_2$ and $R_5$ are H, $E_1$ is C and $E_2$ is O, S or NH (preferably $E_2$ is O).

Preferably, both occurrences of $R_1$ are the same, and are selected from hydrogen, halide, amino, nitro, sulfoxide, sulfonyl, sulfinate, silyl, silyl ether and an optionally substituted alkyl, alkenyl, aryl, heteroaryl, alkoxy, aryloxy or alkylthio; $R_2$ is hydrogen; $R_{3A}$ and $R_{3B}$ are the same or different, and are selected from substituted or unsubstituted alkylene, substituted or unsubstituted cycloalkylene and substituted or unsubstituted arylene; $E_3$ to $E_6$ are the same or different and are selected from $NR_4$, S, N or O; $R_4$ is hydrogen, an optionally substituted alkyl or heteroalkyl; each X is the same, and is selected from $OC(O)R^x$, $OR^x$, halide, carbonate, amino, nitro, alkyl, aryl, heteroaryl, phosphinate or $OSO_2R^x$, $R^x$ is alkyl, alkenyl, alkynyl, heteroalkyl, aryl, heteroaryl or alkylaryl; $R^x$ is alkyl, alkenyl, alkynyl, heteroalkyl, aryl, heteroaryl or alkylaryl; each G (where present) is independently selected from halide; water; a heteroaryl optionally substituted by alkyl, alkenyl, alkynyl, alkoxy, halogen, hydroxyl, nitro or nitrile; $M_1$ and $M_2$ are independently selected from Mg(II), Zn(II), Cr(II), Cr(III)-X, Co(II), Co(III)-X, Mn(II), Ni(II), Ni(III)-X, Fe(II), and Fe(III)-X, preferably $M_1$ and $M_2$ are independently selected from Mg(II), Ni(II), Ni(III)-X and Zn(II). Preferably $M_1$ and $M_2$ are the same, and are selected from Ni(II) or Mg(II).

Preferably, both occurrences of $R_1$ are the same, and are selected from hydrogen, halide, amino, nitro, sulfoxide, sulfonyl, sulfinate, silyl, silyl ether and an optionally substituted alkyl, alkenyl, aryl, heteroaryl, alkoxy, aryloxy or alkylthio; $R_2$ is hydrogen; $R_{3A}$ is a substituted or unsubstituted cycloalkylene or alkylene and $R_{3B}$ is a substituted or unsubstituted alkylene or arylene; each occurrence of $E_3$ to $E_6$ is $NR_4$; $R_4$ is hydrogen; each X is the same, and is selected from $OC(O)R^x$, $OR^x$, halide, carbonate, amino, nitro, alkyl, aryl, heteroaryl, phosphinate or $OSO_2R^x$, $R^x$ is alkyl, alkenyl, alkynyl, heteroalkyl, aryl, heteroaryl or alkylaryl; $R^x$ is alkyl, alkenyl, alkynyl, heteroalkyl, aryl, heteroaryl or alkylaryl; each G (where present) is independently selected from halide; water; a heteroaryl optionally substituted by alkyl, alkenyl, alkynyl, alkoxy, halogen, hydroxyl, nitro or nitrile; $M_1$ and $M_2$ are independently selected from Mg(II), Zn(II), CO(II), Cr(III)-X, Co(II), Co(III)-X, Mn(II), Ni(II), Ni(III)-X, Fe(II), and Fe(III)-X, preferably $M_1$ and $M_2$ are independently selected from Mg(II), Ni(II), Ni(III)-X and Zn(II). Still more preferably $M_1$ and $M_2$ are independently selected from Ni(II), Ni(III), or Mg(II). Preferably $M_1$ and $M_2$ are the same, and are selected from Ni(II) or Mg(II).

Preferably, both occurrences of $R_1$ are the same, and are selected from hydrogen, halide, amino, nitro, sulfoxide, sulfonyl, sulfinate, silyl, silyl ether and an optionally substituted alkyl, alkenyl, aryl, heteroaryl, alkoxy, aryloxy or alkylthio; $R_2$ is hydrogen; $R_{3A}$ and $R_{3B}$ are the same and are substituted or unsubstituted alkylene; each of $E_3$, $E_4$, $E_5$ and $E_6$ is $NR_4$ wherein one of the $R_4$ groups is different from a remaining $R_4$ group and is selected from an optionally substituted alkyl or heteroalkyl and the remaining $R_4$ group/s are hydrogen; each X is the same, and is selected from $OC(O)R^x$, $OR^x$, halide, carbonate, amino, nitro, alkyl, aryl, heteroaryl, phosphinate or $OSO_2R^x$, $R^x$ is alkyl, alkenyl, alkynyl, heteroalkyl, aryl, heteroaryl or alkylaryl; $R^x$ is alkyl, alkenyl, alkynyl, heteroalkyl, aryl, heteroaryl or alkylaryl; each G (where present) is independently selected from halide; water; a heteroaryl optionally substituted by alkyl, alkenyl, alkynyl, alkoxy, halogen, hydroxyl, nitro or nitrile; $M_1$ and $M_2$ are independently selected from Mg(II), Zn(II), Cr(II), Cr(III)-X, Co(II), Co(III)-X, Mn(II), Ni(II), Ni(III)-X, Fe(II), and Fe(III)-X, preferably $M_1$ and $M_2$ are independently selected from Mg(II), Ni(II), Ni(III)-X and Zn(II). Still more preferably $M_1$ and $M_2$ are independently selected from Ni(II), Ni(III), or Mg(II). Preferably $M_1$ and $M_2$ are the same, and are selected from Ni(II) or Mg(II).

Preferably both occurrences of $R_1$ are the same, and are selected from hydrogen, halide, amino, nitro, sulfoxide, sulfonyl, sulfinate, silyl, silyl ether and an optionally substituted alkyl, alkenyl, aryl, heteroaryl, alkoxy, aryloxy or alkylthio; $R_2$ is hydrogen; $R_{3A}$ and $R_{3B}$ are selected from substituted or unsubstituted alkylene, substituted or unsubstituted cycloalkylene and substituted or unsubstituted arylene; $E_3$ to $E_6$ are selected from N, $NR_4$, S or O; $R_4$ is selected from hydrogen, or optionally substituted alkyl or heteroalkyl; each X is the same, and is selected from $OC(O)R^x$, $OR^x$, or $OSO_2R^x$, $R^x$ is alkyl, alkenyl, alkynyl, heteroalkyl, aryl, heteroaryl or alkylaryl; each G (where present) is independently selected from halide; water; a heteroaryl optionally substituted by alkyl, alkenyl, alkynyl, alkoxy, halogen, hydroxyl, nitro or nitrile; $M_1$ and $M_2$ are independently selected from Mg(II), Zn(II), Cr(II), Cr(III)-X, Co(II), Co(III)-X, Mn(II), Ni(II), Ni(III)-X, Fe(II), and Fe(III)-X, preferably $M_1$ and $M_2$ are independently selected from Mg(II), Ni(II), Ni(III)-X and Zn(II). Still more preferably $M_1$ and $M_2$ are independently selected from Ni(II), Ni(III), or Mg(II). Preferably $M_1$ and $M_2$ are the same, and are selected from Ni(II) or Mg(II); wherein:
 i) $R_{3A}$ is different from $R_{3B}$; and/or
 ii) at least one occurrence of $E_3$, $E_4$, $E_5$ and $E_6$ is different to a remaining occurrence of $E_3$, $E_4$, $E_5$ and $E_6$.

More preferably, both occurrences of $R_1$ are the same, and are selected from an optionally substituted alkyl; $R_2$ is hydrogen; $R_{3A}$ and $R_{3B}$ are selected from substituted or unsubstituted alkylene, substituted or unsubstituted cycloalkylene, and substituted or unsubstituted arylene; each occurrence of $E_3$ to $E_6$ is $NR_4$; $R_4$ is selected from hydrogen, or optionally substituted alkyl or heteroalkyl; each X is the same, and is selected from $OC(O)R^x$, $OR^x$, or $OSO_2R^x$, $R^x$ is alkyl, alkenyl, alkynyl, heteroalkyl, aryl, heteroaryl or alkylaryl; $M_1$ and $M_2$ are independently selected from Mg(II), Ni(II), Ni(III)-X and Zn(II). Still more preferably $M_1$ and $M_2$ are independently selected from Ni(II), Ni(III), or Mg(II). Preferably $M_1$ and $M_2$ are the same, and are selected from Ni(II) or Mg(II); wherein:
 i) $R_{3A}$ is different from $R_{3B}$; and/or
 ii) at least one occurrence of $E_3$, $E_4$, $E_5$ and $E_6$ is different to a remaining occurrence of $E_3$, $E_4$, $E_5$ and $E_6$.

Still more preferably, both occurrences of $R_1$ are the same, and are tertiary butyl; $R_2$ is hydrogen; $R_{3A}$ and $R_{3B}$ are selected from butylene, benzylene, ethylene, propylene, 2,2-dimethylpropylene; each occurrence of $E_3$ to $E_6$ is $NR_4$; $R_4$ is selected from hydrogen, methyl, ethyl, propyl, butyl, or -alkyl-C(O)—$OR_{19}$ as defined hereinabove, preferably methyl propanoate; each X is the same, and is OAc; $M_1$ and $M_2$ are independently selected from Mg(II), Ni(II), Ni(III)-X and Zn(II). Still more preferably $M_1$ and $M_2$ are independently selected from Ni(II), Ni(III), or Mg(II). Preferably $M_1$ and $M_2$ are the same, and are selected from Ni(II) or Mg(II);
wherein:
 i) $R_{3A}$ is different from $R_{3B}$; and/or
 ii) at least one occurrence of $E_3$, $E_4$, $E_5$ and $E_6$ is different to a remaining occurrence of $E_3$, $E_4$, $E_5$ and $E_6$.

Exemplary catalysts of the first aspect are as follows:

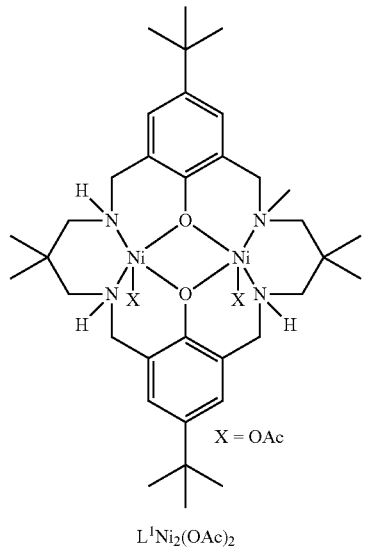

$L^1Ni_2(OAc)_2$

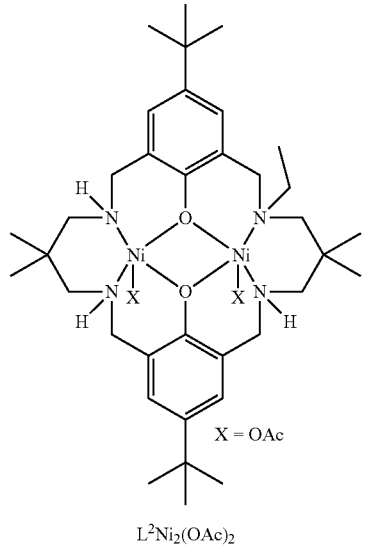

$L^2Ni_2(OAc)_2$

-continued
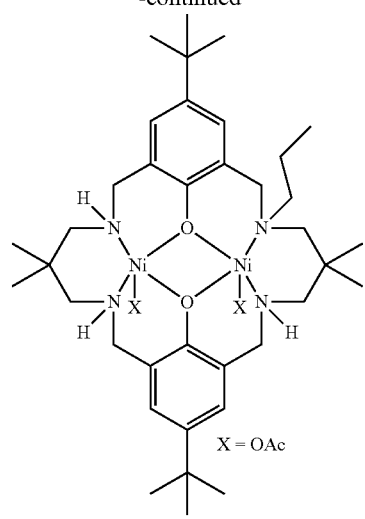
X = OAc
L³Ni₂(OAc)₂
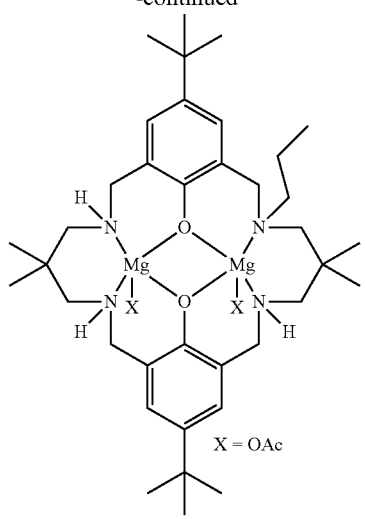
X = OAc
L³Mg₂(OAc)₂
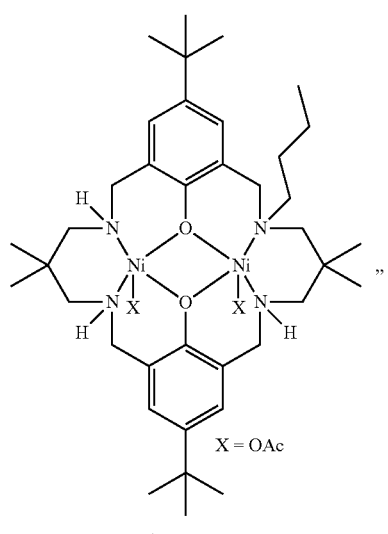
X = OAc
L⁴Ni₂(OAc)₂
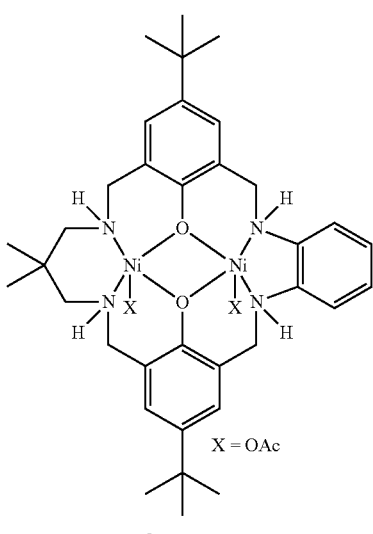
X = OAc
L⁵Ni₂(OAc)₂
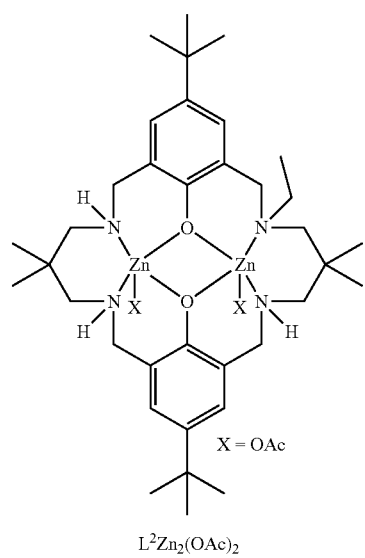
X = OAc
L²Zn₂(OAc)₂
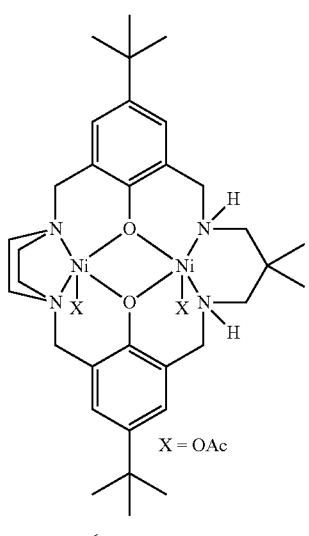
X = OAc
L⁶Ni₂(OAc)₂

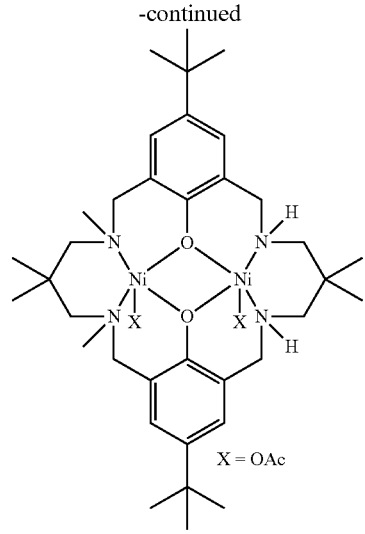
L⁷Ni₂(OAc)₂
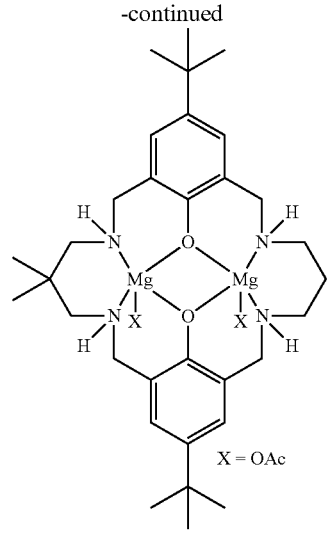
L⁹Mg₂(OAc)₂
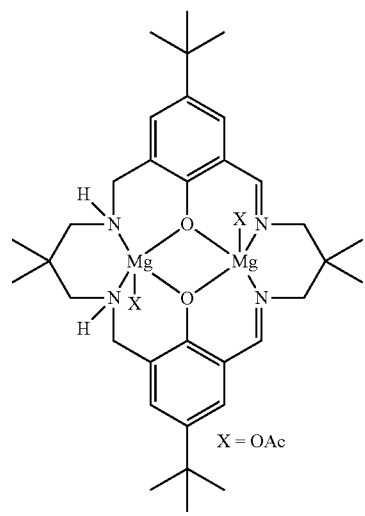
[L_imine⁸Mg₂(OAc₂)]
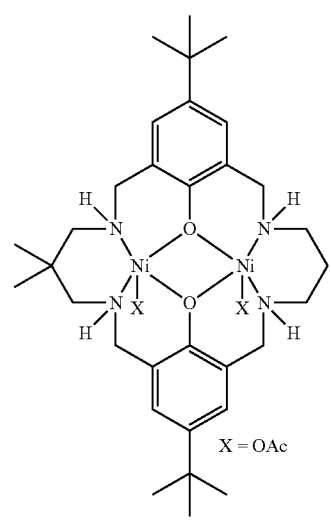
L⁹Ni₂(OAc)₂
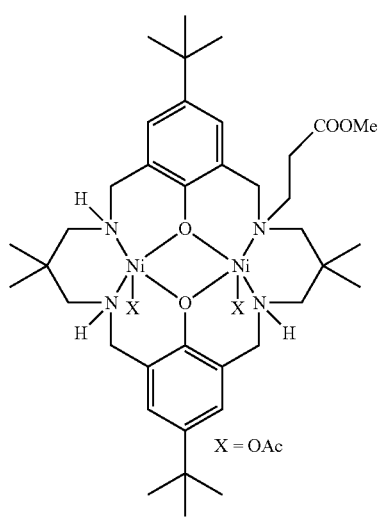
L¹²Ni₂(OAc)₂

-continued
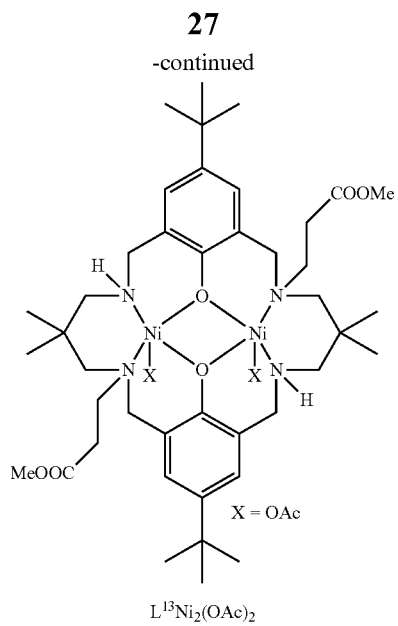
L¹³Ni₂(OAc)₂
More preferably the catalyst of formula (I) is:
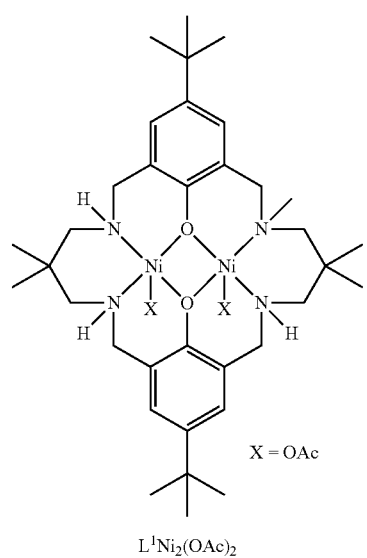
L¹Ni₂(OAc)₂
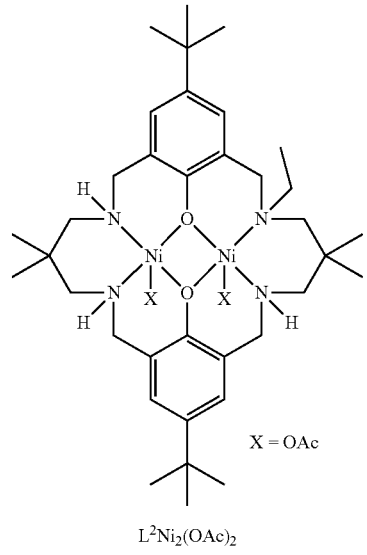
L²Ni₂(OAc)₂
-continued
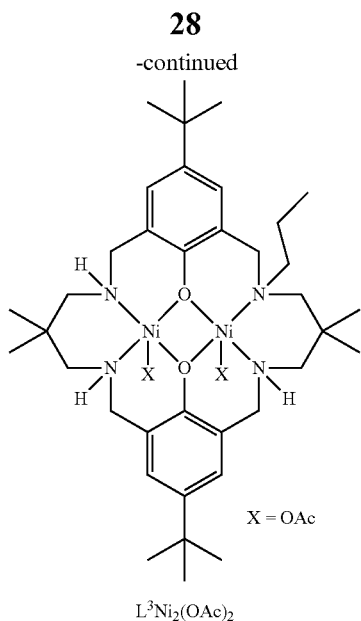
L³Ni₂(OAc)₂
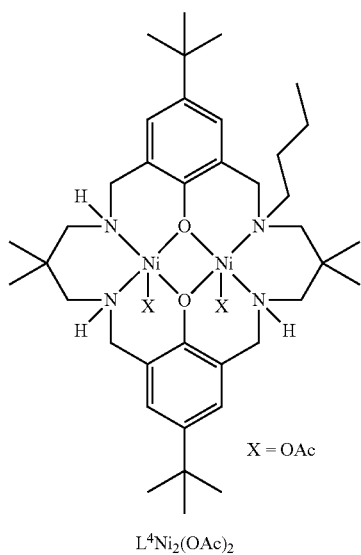
L⁴Ni₂(OAc)₂
L⁷Ni₂(OAc)₂

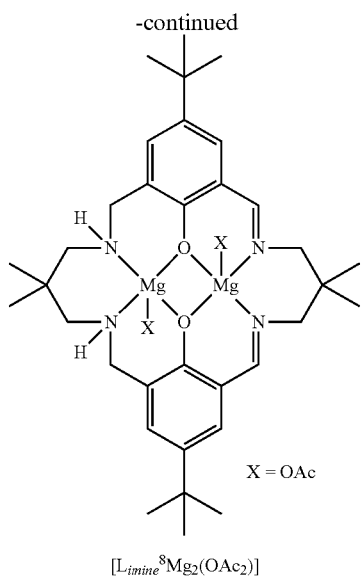

[L$_{imine}$$^8$Mg$_2$(OAc$_2$)]

X = OAc

In the second aspect of the invention, there is provided a ligand of formula (II):

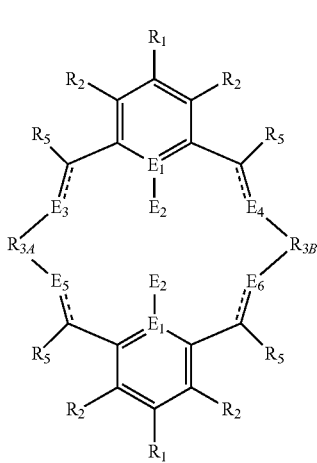

(II)

wherein:
R$_1$ and R$_2$ are independently selected from hydrogen, halide, a nitro group, a nitrile group, an imine, an amine, an ether group, a silyl group, a silyl ether group, a sulfoxide group, a sulfonyl group, a sulfinate group or an acetylide group or an optionally substituted alkyl, alkenyl, alkynyl, haloalkyl, aryl, heteroaryl, alkoxy, aryloxy, alkylthio, arylthio, alicyclic or heteroalicyclic group;
R$_{3A}$ and R$_{3B}$ are independently selected from optionally substituted alkylene, alkenylene, alkynylene, heteroalkylene, heteroalkenylene, heteroalkynylene, arylene, heteroarylene or cycloalkylene, wherein alkylene, alkenylene, alkynylene, heteroalkylene, heteroalkenylene and heteroalkynylene, may optionally be interrupted by aryl, heteroaryl, alicyclic or heteroalicyclic;
R$_5$ is independently selected from H, or optionally substituted aliphatic, heteroaliphatic, alicyclic, heteroalicyclic, aryl, heteroaryl, alkylheteroaryl or alkylaryl;
E$_1$ is C, E$_2$ is OY, S or NH or E$_1$ is N and E$_2$ is O;
Y is hydrogen or an alkali metal;
E$_3$, E$_4$, E$_5$ and E$_6$ are each independently selected from N, NR$_4$, O and S, wherein when any of E$_3$, E$_4$, E$_5$ or E$_6$ are N, ===== is ═, and wherein when any of E$_3$, E$_4$, E$_5$ or E$_6$ are NR$_4$, O or S, ===== is —; R$_4$ is independently selected from H, or optionally substituted aliphatic, heteroaliphatic, alicyclic, heteroalicyclic, aryl, heteroaryl, alkylheteroaryl or alkylaryl;
and wherein:
i) R$_{3A}$ is different from R$_{3B}$; and/or
ii) at least one occurrence of E$_3$, E$_4$, E$_5$ and E$_6$ is different to a remaining occurrence of E$_3$, E$_4$, E$_5$ and E$_6$.

All of the preferred features defined hereinabove in relation to the first aspect apply in relation to the second aspect. In particular, all of the preferred features in relation to the groups R$_1$, R$_2$, R$_{3A}$, R$_{3B}$, R$_4$, R$_5$, E$_1$, E$_2$, E$_3$, E$_4$, E$_5$, and E$_6$ apply equally to the second aspect.

Preferably Y is selected from hydrogen, lithium, sodium, potassium, rubidium, caesium, or francium. More preferably Y is either hydrogen or lithium.

Preferably both occurrences of R$_1$ are the same, and are selected from hydrogen, halide, amino, nitro, sulfoxide, sulfonyl, sulfinate, silyl, silyl ether and an optionally substituted alkyl, alkenyl, aryl, heteroaryl, alkoxy, aryloxy or alkylthio; R$_2$ is hydrogen; R$_{3A}$ and R$_{3B}$ are selected from substituted or unsubstituted alkylene, substituted or unsubstituted cycloalkylene and substituted or unsubstituted arylene; E$_3$ to E$_6$ are N, NR$_4$, S or O; R$_4$ is selected from hydrogen, or optionally substituted alkyl or heteroalkyl;
wherein:
iii) R$_{3A}$ is different from R$_{3B}$; and/or
iv) at least one occurrence of E$_3$, E$_4$, E$_5$ and E$_6$ is different to a remaining occurrence of E$_3$, E$_4$, E$_5$ and E$_6$.

More preferably, both occurrences of R$_1$ are the same, and are selected from an optionally substituted alkyl; R$_2$ is hydrogen; R$_{3A}$ and R$_{3B}$ are selected from substituted or unsubstituted alkylene, substituted or unsubstituted cycloalkylene, and substituted or unsubstituted arylene; each occurrence of E$_3$ to E$_6$ is NR$_4$; R$_4$ is selected from hydrogen, or optionally substituted alkyl or heteroalkyl;
wherein:
i) R$_{3A}$ is different from R$_{3B}$; and/or
ii) at least one occurrence of E$_3$, E$_4$, E$_5$ and E$_6$ is different to a remaining occurrence of E$_3$, E$_4$, E$_5$ and E$_6$.

Still more preferably, both occurrences of R$_1$ are the same and are tertiary butyl; R$_2$ is hydrogen; R$_{3A}$ and R$_{3B}$ are selected from tertiary butylene, benzylene, ethylene, propylene, 2,2-dimethylpropylene; each occurrence of E$_3$ to E$_6$ is NR$_4$; R$_4$ is selected from hydrogen, methyl, ethyl, propyl, butyl, or -alkyl-C(O)—OR$_{19}$ as defined hereinabove, preferably methyl propanoate;
wherein:
i) R$_{3A}$ is different from R$_{3B}$; and/or
ii) at least one occurrence of E$_3$, E$_4$, E$_5$ and E$_6$ is different to a remaining occurrence of E$_3$, E$_4$, E$_5$ and E$_6$.

More preferably still, the ligand of formula (II) is:

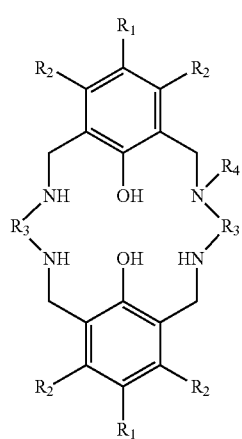

(IIa)

wherein:
R₁ is tertiary butyl; R₂ is hydrogen; R₃ is 2,2-dimethylpropylene; and R₄ is selected from methyl, ethyl, propyl, or butyl;
or the ligand of formula (II) is:
(IIb)
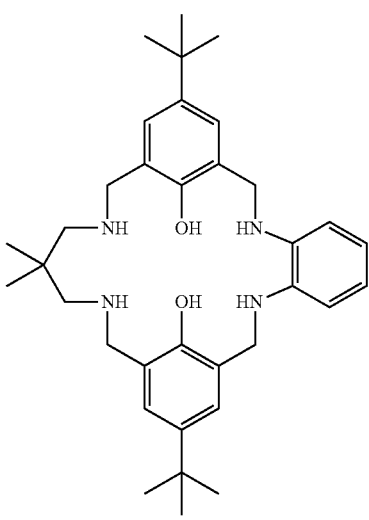
or the ligand of formula (II) is:
(IIc)
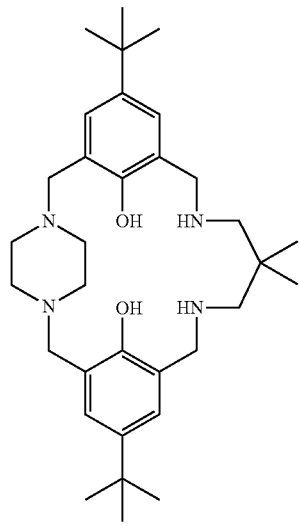
or the ligand of formula (II) is:
(IId)
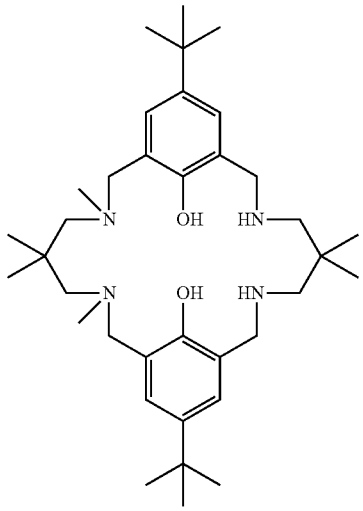
or the ligand of formula (II) is:
(IIe)
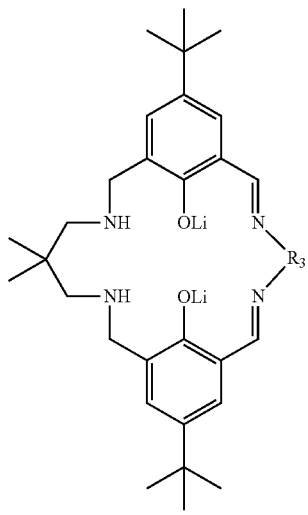
wherein:
R₃ is selected from 2,2-dimethylpropylene, propylene, or ethylene;

or the ligand of formula (II) is:
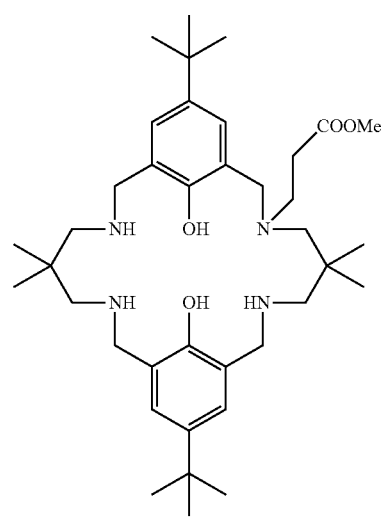
(IIf)
or the ligand of formula (II) is:
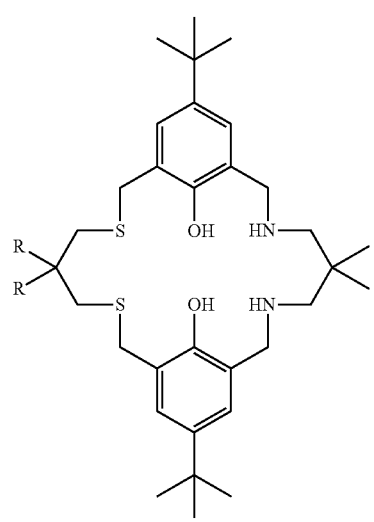
(IIh)
wherein:
R is methyl or hydrogen;
or the ligand of formula (II) is:
or the ligand of formula (II) is:
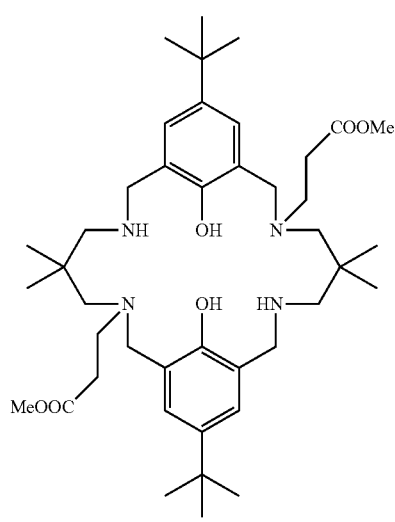
(IIg)
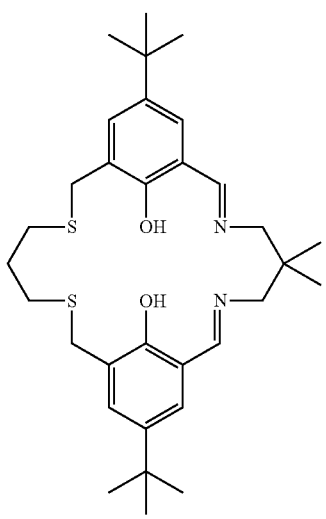
(IIi)

or the ligand of formula (II) is:

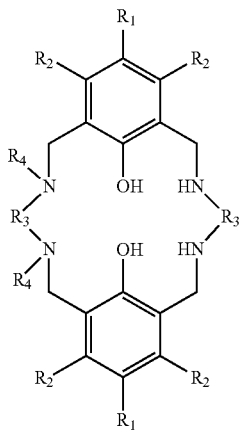
(IIj)

wherein:

R$_1$ is tertiary butyl; R$_2$ is hydrogen; R$_3$ is 2,2-dimethylpropylene; and R$_4$ is methyl, ethyl, propyl, or butyl. Preferably R$_4$ is methyl.

More preferably still, the ligand of formula (II) comprises at least one N-substituent, and may be selected from:

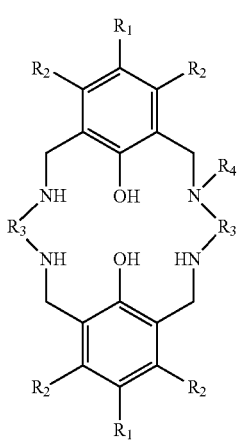
(IIa)

wherein:

R$_1$ is tertiary butyl; R$_2$ is hydrogen; R$_3$ is 2,2-dimethylpropylene; and R$_4$ is selected from methyl, ethyl, propyl, or butyl;

or:

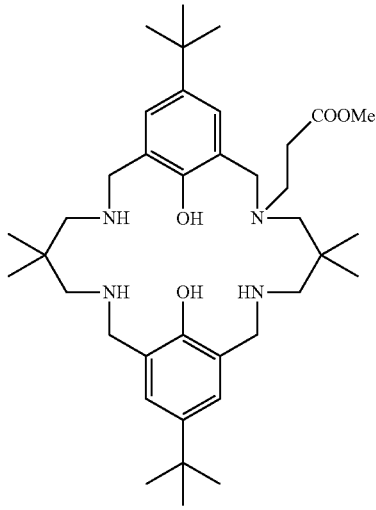
(IIg)

or:

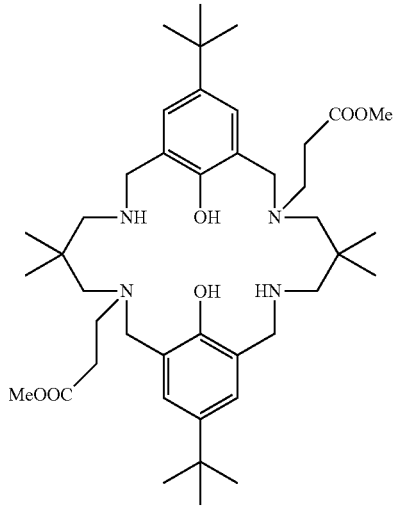
(IIh)

or:

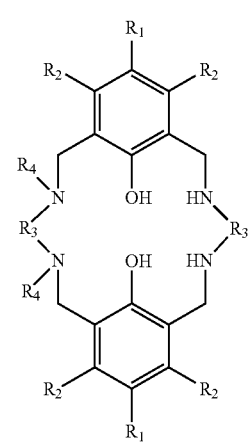
(IIj)

Wherein
R$_1$ is tertiary butyl; R$_2$ is hydrogen; R$_3$ is 2,2-dimethylpropylene; and R$_4$ is methyl, ethyl, propyl, or butyl. Preferably R$_4$ is methyl.

In the third aspect, the invention extends to methods of preparation of ligands, complexes and catalysts according to the second aspect and first aspect respectively or as otherwise defined herein.

In the fourth aspect of the present invention, there is provided a process of asymmetric N-substitution of a symmetrical ligand having a tetraaminophenol coordination sphere, the process comprising the following steps:
 a) protecting at least two of the amino groups of the coordination sphere of the symmetrical ligand with an optionally substituted alkylene;
 b) asymmetrically N-substituting one or more of the protected amino groups of the product of step (a) with a substituent.

Preferably the symmetrical ligand comprises formula (IV):

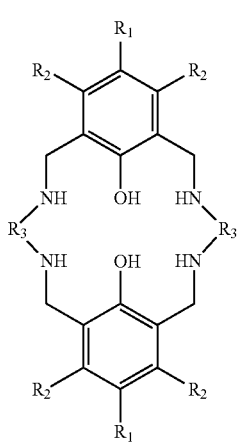

(IV)

wherein:
$R_1$ and $R_2$ are as defined above in relation to the second aspect, and $R_3$ is defined as $R_{3A}$ or $R_{3B}$ in relation to the second aspect.

More preferably therefore, the symmetrical ligand of formula (IVa) is:

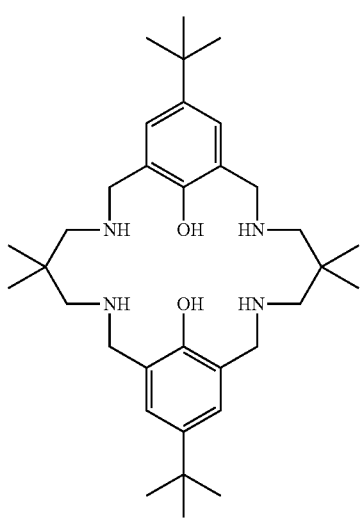

(IVa)

Preferably the optionally substituted alkylene is selected from an optionally substituted methylene or ethylene.

Preferably the optionally substituted alkylene is derived from a protecting reagent. Preferably therefore step (a) comprises reacting the symmetrical ligand with a protecting reagent comprising an optionally substituted alkyl group. Preferably the protecting reagent is an aldehyde, more preferably an aldehyde selected from formaldehyde or benzaldehyde.

Preferably step (a) comprises protecting two or more of the amino groups of the coordination sphere of the symmetrical ligand by forming bridging groups between the adjacent amino or phenolic groups. Preferably the bridging groups are the optionally substituted alkylene, and are selected from an optionally substituted methylene or ethylene.

Preferably the product of step (a) comprises a pair of optionally substituted alkylene bridges between adjacent nitrogen atoms of the coordination sphere.

Preferably step (a) is conducted in the presence of a solvent which may be any suitable solvent for the protecting reagent, for example methanol or THF.

Preferably step (a) comprises contact with the protecting reagent for sufficient time to complete or substantially complete the reaction. Suitable contact times are between 30 minutes and 15 hours, more preferably for between 2 hours and 8 hours, most preferably for around 6 hours.

Preferably step (a) is conducted at a suitable temperature. Suitable temperatures may be in the range −25 to 75° C., for example 0 to 50° C., typically 15-30° C. such as room temperature (around 21° C.).

Preferably step (b) comprises asymmetrically N-substituting one or more of the protected amino groups of the product of step (a) with an N-substituting agent by for example hydroamination with an alkene (such as an acrylate or acrylonitrile) or by using an alkylating agent.

Preferably the substituent is an $R_4$ group, as defined hereinabove. Preferably therefore, one or more of the amino groups is substituted to form an $NR_4$ group.

Preferably step (b) comprises asymmetrically N-substituting one or more of the protected amino groups of the product of step (a) with a substituent. More preferably step (b) comprises asymmetrically N-substituting one or more of the protected amino groups of the product of step (a) with a substituent by reacting the product of step (a) with an N-substituting agent.

Preferably the N-substituting agent is an alkylating agent or an alkene such as an activated alkene for example an alkyl acrylate, alkyl methacrylate, alkyl vinyl ketone or acrylonitrile, more preferably the alkylating agent comprises the formula $R_4X$. Preferably X is a halide, tosylate or triflate, more preferably X is iodine. In one preferred embodiment, $R_4X$ is selected from iodomethane, iodoethane, 1-iodopropane or 1-iodobutane.

Preferably step (b) is conducted in the presence of a solvent which may be any suitable solvent for N-substituting agent, for example methanol, dichloromethane, or THF.

Preferably step (b) comprises contact with the N-substituting agent for sufficient time to complete or substantially complete the reaction. Suitable contact times are between 12 and 22 hours, more preferably between 14 and 18 hours, most preferably for around 16 hours.

Preferably step (b) is conducted at a suitable temperature. Suitable temperatures may be between 20° C. to 90° C., more preferably between 23° C. to 80° C., most preferably at around 25-50° C.

The method may further comprise step (c) hydrolysing the optionally substituted alkylene bridging groups between the adjacent amino groups.

Preferably the hydrolysing of step (c) is performed by reacting the product of step (b) with an acid, more preferably with HCl and subsequently isolating the material Optionally, the method may further comprise upstream steps of formation of the symmetrical ligand having a tetraaminophenol coordination sphere.

Preferably the method further comprises upstream steps of formation of the symmetrical ligand comprising formula (IV):

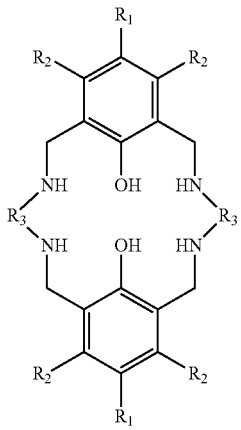

wherein:

$R_1$ and $R_2$ are as defined above in relation to the second aspect, and $R_3$ is defined as $R_{3A}$ or $R_{3B}$ in relation to the second aspect.

More preferably therefore, the method further comprises upstream steps of formation of the symmetrical ligand comprising formula (IVa):

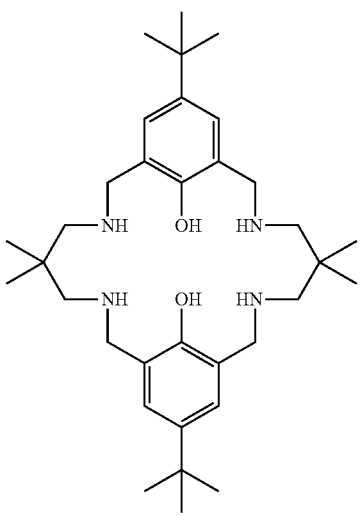

Preferably the upstream steps comprise (1) formation of a symmetrical ligand having a tetraiminophenol coordination sphere, and (2) reduction of the imine groups to amine groups.

Preferably upstream step (1) comprises formation of a symmetrical ligand having a tetraiminophenol coordination sphere from a compound of formula (III):

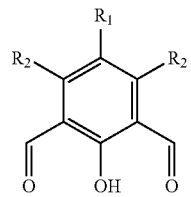

wherein $R_1$ and $R_2$ are as defined hereinabove.

More preferably upstream step (1) comprises reacting a compound of formula (III) with an amine of formula $H_2N$—$R_3$—$NH_2$, wherein $R_3$ is as defined hereinabove.

Upstream step (1) may be conducted in the presence of a suitable solvent, an acid and an electrolyte.

The solvent may be any suitable solvent for the reactants of upstream step (1), for example methanol or THF. More preferably the solvent is methanol.

Preferably upstream step (2) comprises reacting the product of upstream step (1) with a reducing agent.

Suitable reducing agents are known to those skilled in the art, for example sodium borohydride or hydrogen.

Preferably upstream step (2) is conducted in the presence of a solvent, which may be any suitable solvent for the reactants of upstream step (2), for example methanol or THF. More preferably the solvent is methanol.

In one preferred embodiment, the process comprises the following steps:
(a) forming a symmetrical ligand having a tetraiminophenol coordination sphere;
(b) reducing the imino groups of the product of step (a) to amino groups;
(c) protecting the amino groups of the product of step (b) with an optionally substituted alkylene;
(d) asymmetrically N-substituting one or more of the protected amino groups of the product of step (c) with a substituent;
(e) hydrolysing the optionally substituted alkylene groups of the product of step (d) to remove the alkylene bridging group;
(f) optional neutralisation of the product of step (e).

In a more preferred embodiment, the process comprises the following steps:
(a) reacting a compound of formula (III) with an amine of formula $H_2N$—$R_3$—$NH_2$ to form a ligand having a tetraiminophenol coordination sphere;

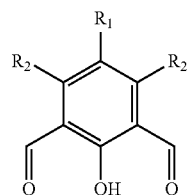

(b) reducing the imino groups of the product of step (a) to amino groups;
(c) protecting the amino groups of the product of step (b) by forming bridging groups between the adjacent amino groups, wherein the bridging groups are optionally substituted alkylenes;

(d) asymmetrically N-substituting one or more of the protected amino groups of the product of step (c) with an N-substituting agent;
(e) hydrolysing the optionally substituted alkylene groups of the product of step (d);
(f) optional neutralisation of the product of step (e);
wherein $R_1$, $R_2$, $R_3$, $R_4$ and X are as defined in relation to the second aspect.

Preferably the asymmetrical ligand produced is that according to the second aspect.

Preferably, the ligand according to the second aspect is that of formula (IIa):

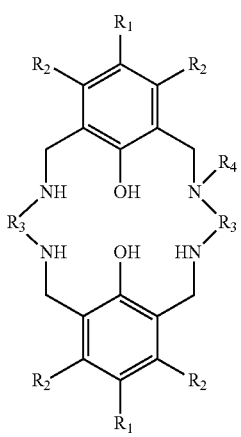

(IIIa)

wherein:
$R_1$ is tertiary butyl; $R_2$ is hydrogen; $R_3$ is 2,2-dimethylpropylene; and $R_4$ is selected from methyl, ethyl, propyl, or butyl.

Preferably in formula IV, R1 is tertiary butyl; $R_2$ is hydrogen; $R_3$ is 2,2-dimethylpropylene.

In a fifth aspect of the invention, the catalysts of the first aspect are capable of polymerising (i) carbon dioxide and an epoxide, (ii) an epoxide and an anhydride, and (iii) a lactide and/or a lactone. Therefore, in a fifth aspect of the invention there is provided a process for the reaction of carbon dioxide with an epoxide, an anhydride with an epoxide, or a lactide and/or a lactone in the presence of a catalyst according to the first aspect.

The process of the fifth aspect may be carried out in the presence of a chain transfer agent. Suitable chain transfer agents include the chain transfer agents, for example as defined by formula (II), in WO 2013/034750, the entire contents of which are hereby incorporated by reference. For example, the chain transfer agent may be water, or may comprise at least one amine (—NHR), alcohol (—OH) or thiol (—SH) moiety.

Examples of chain transfer agents useful in the second aspect include water, mono-alcohols (i.e. alcohols with one OH group, for example, 4-ethylbenzenesulfonic acid, methanol, ethanol, propanol, butanol, pentanol, hexanol, phenol, cyclohexanol), diols (for example, 1,2-ethanediol, 1-2-propanediol, 1,3-propanediol, 1,2-butanediol, 1-3-butanediol, 1,4-butanediol, 1,5-pentanediol, 1,6-hexanediol, 1,2-diphenol, 1,3-diphenol, 1,4-diphenol, catechol and cyclohexenediol), triols (glycerol, benzenetriol, 1,2,4-butanetriol, tris(methylalcohol)propane, tris(methylalcohol)ethane, tris(methylalcohol)nitropropane, trimethylolpropane, preferably glycerol or benzenetriol), tetraols (for example, calix[4]arene, 2,2-bis(methylalcohol)-1,3-propanediol, di(trimethylolpropane)), polyols (for example, D-(+)-glucose, dipentaerythritol or D-sorbitol), dihydroxy terminated polyesters (for example polylactic acid), dihydroxy terminated polyethers (for example poly(ethylene glycol)), acids (such as diphenylphosphinic acid), starch, lignin, mono-amines (i.e. methylamine, dimethylamine, ethylamine, diethylamine, propylamine, dipropylamine, butylamine, dibutylamine, pentylamine, dipentylamine, hexylamine, dihexylamine), diamines (for example 1,4-butanediamine), triamines, diamine terminated polyethers, diamine terminated polyesters, mono-carboxylic acids (for example, 3,5-di-tert-butylbenzoic acid), dicarboxylic acids (for example, maleic acid, malonic acid, succinic acid, glutaric acid or terephthalic acid, preferably maleic acid, malonic acid, succinic acid, glutaric acid), tricarboxylic acids (for example, citric acid, 1,3,5-benzenetricarboxylic acid or 1,3,5-cyclohexanetricarboxylic acid, preferably citric acid), mono-thiols, dithoils, trithiols, and compounds having a mixture of hydroxyl, amine, carboxylic acid and thiol groups, for example lactic acid, glycolic acid, 3-hydroxypropionic acid, natural amino acids, unnatural amino acids, monosaccharides, disaccharides, oligosaccharides and polysaccharides (including pyranose and furanose forms). Preferably, the chain transfer agent is selected from cyclohexene diol, 1,2,4-butanetriol, tris(methylalcohol)propane, tri(methylalcohol)propane, tri (methylalcohol)butane, pentaerythritol, poly(propylene glycol), glycerol, mono- and di-ethylene glycol, propylene glycol, tris(methylalcohol)nitropropane, tris(methylalcohol)ethane, 2,2-bis(methylalcohol)-1,3-propanediol, 1,3,5-benzenetricarboxylic acid, 1,3,5-cyclohexanetricarboxylic acid, 1,4-butanediamine, 1,6-hexanediol, D-sorbitol, 1-butylamine, terephthalic acid, D-(+)-glucose, 3,5-di-tert-butylbenzoic acid, and water.

The process of the fifth aspect may be carried out in the presence of a solvent. Examples of solvents useful in the third aspect include toluene, diethyl carbonate, dimethyl carbonate, dioxane, dichlorobenzene, methylene chloride, propylene carbonate, ethylene carbonate, acetone, ethyl acetate, tetrahydrofuran (THF), etc.

When the process of the fifth aspect involves the reaction of an epoxide, the epoxide may be any compound comprising an epoxide moiety. The epoxide may be purified (for example by distillation, such as over calcium hydride) prior to reaction with carbon dioxide or the anhydride. For example, the epoxide may be distilled prior to being added to the reaction mixture comprising the catalyst.

The process of the fifth aspect of the invention may be carried out at a pressure of 1 to 100 atmospheres, preferably at 1 to 40 atmospheres, such as at 1 to 20 atmospheres, more preferably at 1 or 10 atmospheres. The catalysts used in the process of the second aspect allow the reaction to be carried out at low pressures.

The process of the fifth aspect of the invention may be carried out at a temperature of about 0° C. to about 250° C., preferably from about 40° C. to about 160° C., even more preferably from about 50° C. to about 120° C. The duration of the process may be up to 168 hours, such as from about 1 minute to about 24 hours, for example from about 5 minutes to about 12 hours, e.g. from about 1 to about 6 hours.

The process temperature, for copolymerisations of carbon dioxide and an epoxide, may be used to control the product composition. When the temperature of the process of the fifth aspect which involves reacting carbon dioxide and an epoxide is increased, the selectivity of the catalyst towards the formation of cyclic carbonate is also increased. The catalysts and processes may operate at temperatures up to 250° C.

The process of the fifth aspect of the invention may be carried out at low catalytic loading. For example, when the reaction involves copolymerisation of carbon dioxide and an epoxide, the catalytic loading for the process is preferably in the range of 1:1,000-300,000 catalyst:epoxide, more preferably in the region of 1:10,000-100,000 catalyst:epoxide, even more preferably in the region of 1:50,000-100,000 catalyst:epoxide. When the process involves copolymerisation of an epoxide and an anhydride, or the reaction of a lactide and/or lactone, the catalytic loading for the process is preferably in the range of 1:1,000-300,000 catalyst:total monomer content, more preferably in the region of 1:10,000-100,000 catalyst:total monomer content, even more preferably in the region of 1:50,000-100,000 catalyst:total monomer content. The ratios above are molar ratios.

The catalysts of the first aspect, and in particular catalysts wherein both $M_1$ and $M_2$ are selected from Ni(II) and Mg(II), have high activity and selectivity for producing polycarbonates by reacting carbon dioxide and an epoxide, optionally in the presence of a chain transfer agent, and preferably at temperatures between about 40° C. to about 160° C. Thus, the reaction times for the process of the second aspect can be less than 12 hours, and preferably from about 2 to about 6 hours.

The process of the fifth aspect can be carried out in a batch reactor or a continuous reactor.

It will be appreciated that the various features described above for the process of the fifth aspect may be present in combination mutatis mutandis. All preferred features of the first aspect apply equally to the fifth aspect and may be present in combination mutatis mutandis.

The sixth aspect of the invention provides a product of the process of the fifth aspect of the invention. All preferred features of the fifth aspect of the invention apply to the sixth aspect of the invention mutatis mutandis.

When the process of the fifth aspect is carried out in the presence of a chain transfer agent, it produces polymer chains which are terminated at substantially all ends with hydroxyl groups (i.e. polycarbonate polyols or polyester polyols). By "substantially", it is meant that at least 90% of the resultant polymer chains, preferably at least 95% of the resultant polymer chains, and even more preferably at least 98%, and even more preferably at least about 99% of the resultant polymer chains are terminated at all ends in hydroxyl groups. In order for at least 90% of the resultant polymer chains to be terminated at all ends with hydroxyl groups, it is preferred for the process of the second aspect to be carried out in the presence of at least about 4 equivalents of chain transfer agent, relative to the amount of catalyst. In order for at least 95% of the resultant polymer chains to be terminated at all ends with hydroxyl groups, it is preferred for the process of the second aspect to be carried out in the presence of at least about 10 equivalents of chain transfer agent, relative to the amount of catalyst. In order for at least 98% of the resultant polymer chains to be terminated at all ends with hydroxyl groups, it is preferred for the process of the fifth aspect to be carried out in the presence of at least about 20 equivalents of chain transfer agent, relative to the amount of catalyst. Thus, polyols obtained by the process of the fifth aspect are considered to form part of the sixth aspect of the invention.

The chain transfer agent referred to in the fifth aspect may be used to control the molecular weight ($M_n$) of the polymer products of the sixth aspect. Preferably, the molecular weight ($M_n$) of the polymer products of the sixth aspect is greater than about 200 g/mol. The molecular weight ($M_e$) of the polymer products of the sixth aspect may be from about 200 g/mol to about 200,000 g/mol. The molecular weight of the polymers produced by the fifth aspect can be measured by Gel Permeation Chromatography (GPC) using, for example, a GPC-60 manufactured by Polymer Labs, using THF as the eluent at a flow rate of 1 ml/min on Mixed B columns, manufactured by Polymer Labs. Narrow molecular weight polystyrene standards can be used to calibrate the instrument.

It is possible to produce polycarbonate polyols and polyester polyols having a $M_n$ of from about 200 g/mol to about 20,000 g/mol, preferably less than about 10,000 g/mol by adding a chain transfer agent to the process of the fifth aspect.

It is also possible to produce polymers having a $M_n$ of greater than about 20,000 g/mol from the process of the fifth aspect. Preferably, the polymer having a $M_n$ of greater than about 20,000 g/mol is a polycarbonate or a polyester, even more preferably a polycarbonate. Preferably, the polymer having a $M_n$ of greater than about 20,000 g/mol is a polycarbonate and is produced carrying out the process of the fifth aspect without adding a chain transfer agent (CTA).

The polymers produced by the fifth aspect may be produced to have a polydispersity index (PDI) of less than about 2, more preferably less than about 1.5, and even more preferably less than about 1.2. Furthermore, it is possible to control the molecular weight distribution so as to produce multi-modal or broad molecular weight distribution polymers by addition of one or more chain transfer agent(s).

The polymers produced by the process of the fifth aspect (e.g. polycarbonates such as PCHC or PPC), are useful building blocks in the preparation of various copolymeric materials. The polymers produced by the process of the fifth aspect may undergo further reaction, for example to produce polymeric products such as polyureas or polyamines. These processes and reactions are well known to the skilled person (for example, refer to WO2013/034750).

The polycarbonate or polyester polyols produced by the process of the fifth aspect may be used in various applications and products which conventionally use polyols, including adhesives (such as hot melt adhesives and structural adhesives), a binder (such as forest product binders, foundry core binders and rubber crumb binders), coatings (such as powder coatings, transport, e.g. automotive or marine coatings, fast cure coatings, self-healing coatings, top coats and primers, varnishes, and coatings for marine applications, e.g. oil rigs), elastomers (such as cast elastomers, fibres/spandex elastomers, footwear elastomers, RIM/RRIM elastomers, synthetic leather elastomers, technical microcellular elastomers and TPU elastomers), flexible foams (such as viscoelastic foams), rigid foams (such as rigid and flexible panels, moulded rigid foams, aerosol gap filling foam, spray foams, refrigeration foams, pour-in-place foams, and foam slabs) and sealants (such as glazing sealants for commercial, industrial and transport (e.g. automotive) applications, and construction sealants). The polyamines and polyureas can be processed using methods standard techniques known in the art, such as foaming.

It will be understood that the polycarbonate and polyester polyols produced by the process of the fifth aspect may be mixed with other polyols prior to further use or reaction.

The polycarbonates, and in particular, polycarbonates having a $M_n$ of greater than about 20,000 g/mol (e.g. produced without adding chain transfer agent to the process of the fifth aspect) may have a number of beneficial properties including high strength, high toughness, high gloss, high transparency, low haze, high gas (e.g. oxygen and carbon dioxide) or water barrier properties, flame resistance, UV resistance, high durability, rigidity and stiffness, compatibility with plasticizers, broad dimensional stability temperature, biodegradability and biocompatibility, and modulus of elasticity and yield strength comparable to LDPE. Thus, these polymers may be used in various applications and products, such as electronic components, construction materials, data storage products, automotive and aircraft products, security components, medical applications, mobile phones, packaging (including bottles), optical applications (such as safety glass, windscreens, etc).

EXAMPLE

Example 1: Synthesis of Asymmetric Ligands $H_2L^{1-4}$

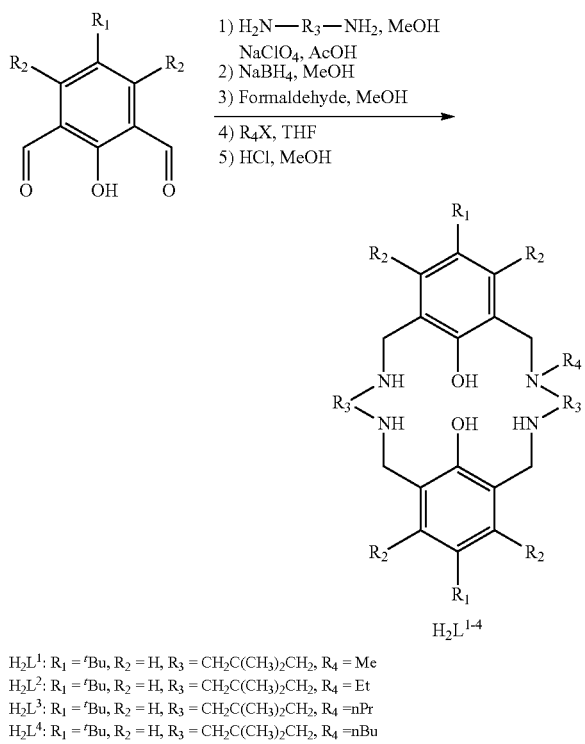

$H_2L^1$: $R_1 = {}^tBu$, $R_2 = H$, $R_3 = CH_2C(CH_3)_2CH_2$, $R_4 = Me$
$H_2L^2$: $R_1 = {}^tBu$, $R_2 = H$, $R_3 = CH_2C(CH_3)_2CH_2$, $R_4 = Et$
$H_2L^3$: $R_1 = {}^tBu$, $R_2 = H$, $R_3 = CH_2C(CH_3)_2CH_2$, $R_4 = nPr$
$H_2L^4$: $R_1 = {}^tBu$, $R_2 = H$, $R_3 = CH_2C(CH_3)_2CH_2$, $R_4 = nBu$

Ligands $H_2L^{1-4}$ were prepared by the following method:

A tetraaminophenol ligand may be formed by the following process (steps 1 and 2):

To a round-bottomed flask was added 4-tert-butyl-2,6-diformylphenol (1.20 g, 5.80 mmol), $NaClO_4$ (2.81 g, 23.2 mmol), acetic acid (0.66 mL, 11.6 mmol) and methanol (90 mL). This solution was heated to 70° C. whilst stirring, as the solution started to boil, 2,2-dimethyl-1,3-propanediamine (0.70 mL, 5.8 mmol) was added slowly in methanol (30 mL). The yellow reaction mixture was allowed to cool to room temperature, and left stirring for 24 hours, after which a bright orange precipitate was filtered and washed with cold (−78° C.) methanol (1.85 g, 95%). The product was suspended in methanol (180 mL). The suspension was cooled to 0° C. and $NaBH_4$ (2.65 g, 69.9 mmol) was added slowly. As $NaBH_4$ was added, the red-orange suspension turned to a clear solution. Water was added slowly, and the solution turned cloudy. Once precipitate started to form, the mixture was left overnight and $H_2L^{11}$ was filtered off as a white solid (1.21 g, 88%).

To a solution of the resulting product (20.8 mmol) in methanol (500 mL) was added a formaldehyde solution (37% in water, 104 mmol) at room temperature (RT). The reaction was stirred at RT for 15 h after which the reaction mixture was filtered and the filter cake was washed with MeOH and water. The resultant white powder was transferred to a round bottom flask. Toluene was added and evaporated under reduced pressure to azeotrope off the residual water giving the desired product as a white powder (17.2 mmol). $R_4X$ (iodomethane, iodoethane, 1-iodopropane or 1-iodobutane, 104 mmol) was added to a stirred solution of this white powder (10.4 mmol) in anhydrous THF (120 mL) at 25° C. until the reaction was deemed to be complete. A white precipitate formed in the reaction mixture and was collected by suction filtration. The filter cake was washed with THF. The resultant white powder was transferred to a round bottom flask and dried under high vacuum for several hours. This was dissolved (7.3 mmol) in MeOH and concentrated $HCl_{(aq)}$ (1:1) and placed in a heating block set to 75° C. whilst refluxing and stirred for 15 h. After this time, the slightly yellow solution was allowed to cool to RT and was neutralized with a saturated aqueous solution of $K_2CO_3$, inducing the product to precipitate out of solution as a white solid. This solid was collected and dried.

$H_2L^1$:

$^1$H NMR (400 MHz, $CDCl_3$) δ 7.05 (d, J=2.4 Hz, 1H), 7.02 (d, J=2.4 Hz, 1H), 6.89 (d, J=2.5 Hz, 1H), 6.85 (d, J=2.5 Hz, 1H), 3.74 (s, 2H), 3.61 (s, 2H), 3.54 (s, 2H), 3.51 (s, 2H), 2.50 (s, 2H), 2.39 (s, 2H), 2.37 (s, 2H), 2.29 (s, 2H), 2.27 (s, 3H), 1.30 (3) (s, 9H), 1.29 (6) (s, 9H), 0.93 (s, 6H), 0.92 (s, 6H).

MS (ESI) m/z: 567.5 ([M+H]$^+$, 100%).

$H_2L^2$:

$^1$H NMR (400 MHz, $CDCl_3$) δ 7.08 (m, 2H), 6.87 (m, 2H), 3.77 (s, 2H), 3.58 (s, 2H), 3.53 (s, 4H), 2.55 (s, 2H), 2.53 (q, J=7.0 Hz, 2H), 2.41 (s, 2H), 2.33 (s, 4H), 1.34 (s, 9H), 1.33 (s, 9H), 1.07 (t, J=7.0 Hz, 3H), 0.94 (s, 6H), 0.92 (s, 6H).

MS (ESI) m/z: 581.5 ([M+H]$^+$, 100%).

$H_2L^3$:

$^1$H NMR (400 MHz, $CDCl_3$) δ 7.11 (m, 2H), 6.84 (m, 2H), 3.76 (s, 2H), 3.52 (s, 2H), 3.50 (m, 4H), 2.54 (s, 2H), 2.48 (m, 2H), 2.38 (s, 2H), 2.32 (s, 2H), 2.30 (s, 2H), 2.20 (s, 2H), 1.59 (m, 2H), 1.34 (s, 18H), 0.93 (s, 6H), 0.91 (s, 6H).

MS (ESI) m/z: 595.5 ([M+H]$^+$, 100%), 581.5 ([M−$CH_3$+H]$^+$, 30%).

$H_2L^4$:

$^1$H NMR (400 MHz, $CDCl_3$) δ 7.11 (m, 2H), 6.83 (m, 2H), 3.75 (s, 2H), 3.51 (m, 6H), 2.53 (s, 2H), 2.49 (m, 2H), 2.38 (s, 2H), 2.32 (s, 2H), 2.30 (s, 2H), 1.55 (m, 2H), 1.34 (s, 18H), 0.94 (q, J=7.3 Hz, 3H), 0.93 (s, 6H), 0.91 (s, 6H).

MS (ESI) m/z: 609.5 ([M+H]$^+$, 100%), 595.5 ([M−$CH_3$+H]$^+$, 10%), 581.5 ([M−$CH_2CH_3$+H]$^+$, 10%).

Example 2: Synthesis of Asymmetric Ligand H₂L⁵

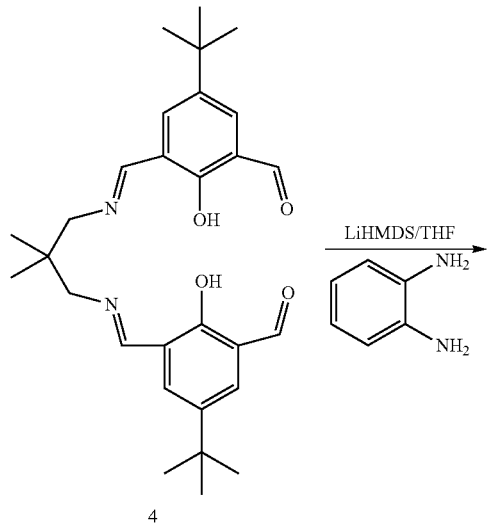

4-tert-butyl-2,6-diformylphenol (4 mmol) and 1,3-diamino-2,2-dimethylpropane (2 mmol) were each dissolved in EtOH (15 mL and 10 mL respectively). The solutions were warmed to boiling then the solution of amine added dropwise with stirring giving an immediate colour change to a deeper yellow. After stirring overnight the precipitate was collected, washed with cold ethanol (2×5 mL), pentane (1×5 mL) then dried under vacuum, giving 4. $^1$H NMR (CDCl$_3$) δ: 14.45 (br s, 2H), 10.56 (s, 2H), 8.45 (s, 2H), 7.94 (s, 2H), 7.55 (s, 2H), 3.58 (s, 4H), 1.34 (s, 18H), 1.15 (s, 6H).

4 (0.4 mmol) was dissolved in THF (10 mL) and treated with LiHMDS (0.8 mmol) in THF (3 mL) causing the bright yellow solution to change to a greenish yellow solution. After 30 mins a solution of 1,2-diaminobenzene (0.4 mmol) was added in THF (10 mL) over 10 mins with rapid stirring. After stirring overnight the colour had again returned to bright yellow. The solution was concentrated to 2 mL and layered with heptane (10 mL) and allowed to stand. The yellow solid that precipitated after 1 day was collected and washed with pentane (2×5 mL) then dried under vacuum. $^1$H NMR (CDCl$_3$) δ: 9.51 (s, 2H), 7.91 (s, 2H), 7.45 (d, 2H), 7.38 (d, 2H), 6.74 (s, 4H), 3.4 (br s, 4H), 1.34 (s, 18H), 0.62 (s, 6H).

5 (0.2 mmol) was dissolved in dry MeOH (25 mL) under nitrogen in a dried 3-neck round-bottomed flask. HCl in EtOH was added (1.2 mmol) and the solution stirred for 10 minutes before NaBH$_4$ (2 mmol) was added in portions. The solution was stirred for 2 hours after which the solvent was removed under vacuum. Water (20 mL) was added to the crude and the pH brought up to 6-7 by adding AcOH dropwise. The product (H$_2$L$^{510}$) was extracted with DCM (2×25 mL), dried over NaSO$_4$ and the solvent removed under vacuum.

$^1$H NMR (CDCl$_3$) δ: 7.2-7.35 (m, 2H), 7.19 (s, 1H), 7.01 (s, 1H), 6.85-6.95 (m, 4H), 4.32 (s, 4H), 4.26 (br s, 2H), 4.08 (s, 2H), 2.59 (s, 4H), 2.42 (s, 2H), 1.32 (s, 18H), 1.16 (s, 6H). $^{13}$C NMR (CDCl$_3$) δ: 154.4, 141.7, 138.0, 129.2, 128.4, 126.9, 125.4, 125.1, 124.9, 122.4, 119.2, 111.3, 59.5, 54.2, 46.5, 35.1, 34.1, 31.7, 24.6.

Example 3: Synthesis of Asymmetric Ligand H₂L⁶

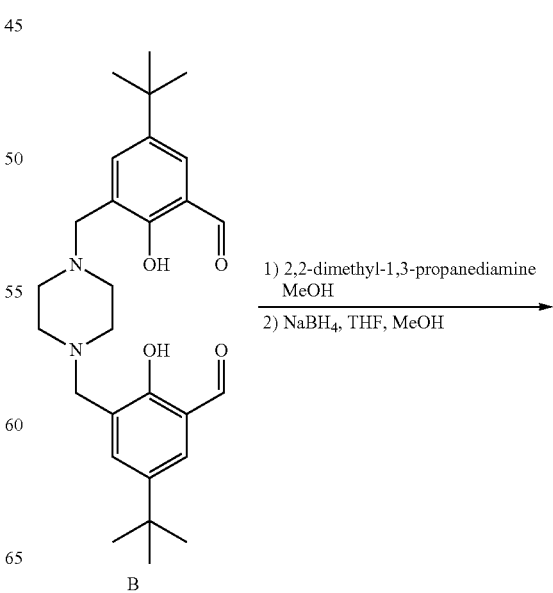

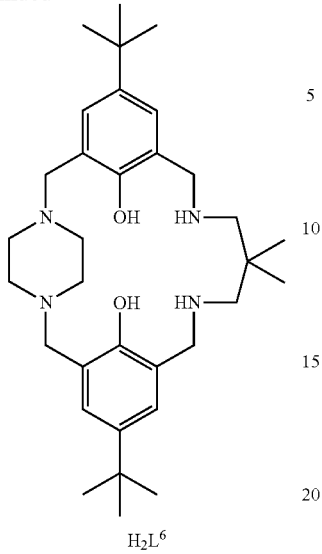

H₂L⁶

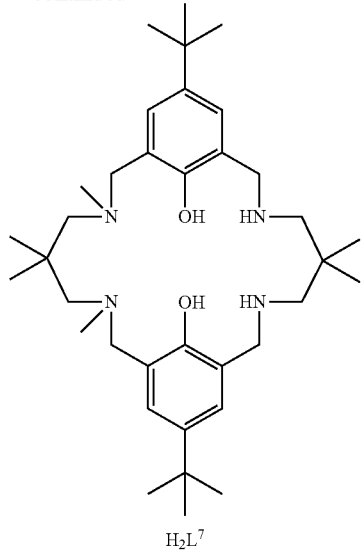

H₂L⁷

The asymmetric ligand H₂L⁶ was prepared using the following method:

B was formed by reacting 4-tert-butylsalicylaldehyde (15 mmol) with piperazine (7.5 mmol) and formaldehyde (15 mmol) in glacial acetic acid (25 mL) at 120° C. The white precipitate was collected and washed with ethanol and diethyl ether.

A solution of 2,2-dimethyl-1,3-propanediamine (6.4 mmol) in MeOH (60 mL) was added dropwise over 6 h to a refluxing solution of B (6.4 mmol) in MeOH (300 mL). After a further 10 h reflux, the solution was cooled to RT and the bright yellow supernatant decanted from a bright yellow solid. The residue was re-dissolved in DCM and co-evaporated with MeOH until a yellow precipitate formed. The resulting solids were collected by filtration, washed with MeOH, pentane and dried under high vacuum for 2 h. This gave a yellow powder (5.0 mmol). A solution of this yellow powder in THF/MeOH (3:1) was treated with solid NaBH₄. The resulting white suspension was allowed to stir for 1 h at RT, then partitioned between NaHCO₃ (2M, aq) and DCM. The organic phase was separated and dried over Na₂SO₄, then evaporated to dryness to yield H₂L⁶.

H₂L⁶:

¹H NMR (400 MHz, CDCl₃) δ 7.14-7.05 (m, 2H), 7.05-6.96 (m, 2H), 5.37-5.27 (s, 4H), 3.89-3.81 (s, 4H), 3.70-3.63 (s, 4H), 2.67-2.62 (s, 4H), 2.55-2.49 (s, 2H), 1.35 (s, 18H), 0.99-0.90 (s, 6H).

Example 4: Synthesis of Asymmetric Ligand H₂L⁷

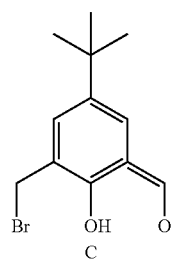

C

1) N,N'-dimethyl-2,2-dimethyl-1,3-propanediamine THF, Et₃N
2) LiOH, MeOH
3) 2,2-dimethyl-1,3-propanediamine, EtOH
4) HCl/Et₂O, EtOH
5) NaBH₄

The asymmetric ligand H₂L⁷ was prepared using the following method:

C was prepared by reacting 4-tert-butylsalicylaldehyde (129 mmol) with formaldehyde (193 mmol) in HBr (48% aq, 970 mmol) with a few catalytic drops of H₂SO₄ at 70° C. for 16 hours. The solution was cooled, diluted and extracted with methylene chloride (30 mL), giving C.

N,N'-dimethyl-2,2-dimethyl-1,3-propanediamine was prepared by reaction of 2,2-dimethyl-1,3-propanediamine (166 mmol) with ethyl formate (80 mL) followed by reduction with LiAlH₄ (10 g) in diethyl ether (250 mL).

A solution of 3-(bromomethyl)-2-hydroxy-5-tert-butyl-benzaldehyde C (48.4 mmol) in THF (40 mL) was added to a stirred solution of N,N'-dimethyl-2,2-dimethyl-1,3-propanediamine (22.0 mmol) in THF (20 mL) giving a yellow suspension. A solution of triethylamine (61.6 mmol) in THF (10 mL) was added dropwise. The reaction mixture was stirred for 2 h after which time it was partitioned between EtOAc and water. The organic extracts were combined, and dried over Na₂SO₄ before evaporation to dryness to yield an orange oil. The crude product was dissolved in MeOH (50 mL) and treated with a solution of LiOH (88 mmol) in MeOH (75 mL). After standing overnight the yellow crystalline precipitate was isolated by filtration, washed with ice cold MeOH and dried under high vacuum overnight. This gave a yellow microcrystalline solid (27.6 mmol). A solution of 2,2-dimethyl-1,3-propanediamine (3.52 mmol) in EtOH (18 mL) was added dropwise over 6 h to a suspension of the latter yellow microcrystalline solid (3.49 mmol) and the resulting yellow solution was allowed to stir for a further 8 h. The solvent was removed completely and the yellow solid residue was suspended in pentane and collected by filtration, washed with pentane and dried under high vacuum for 2 h. This gave a yellow powder (2.8 mmol). A suspension of this yellow powder in dry EtOH was treated with a solution of HCl in diethyl ether (2M). Next, solid NaBH₄ was added in one portion. The resulting white suspension was allowed to stir for 1 h at RT then partitioned between NaHCO₃ (2M, aq) and DCM. The organic phase was separated and dried over Na₂SO₄ then evaporated to dryness to yield H₂L⁷.

H₂L⁷:

¹H NMR (400 MHz, CDCl₃) δ 7.05-6.95 (m, 4H), 5.37-5.27 (s, 4H), 3.81-3.74 (s, 4H), 3.72-3.65 (s, 4H), 2.52-2.45

(s, 4H), 2.45-2.40 (s, 4H), 2.29-2.24 (s, 6H), 1.34-1.24 (s, 18H), 1.01-0.92 (d, J=5.5 Hz, 6H).

Example 5: Synthesis of Asymmetric Ligands Li$_2$L$_{imine}$$^{8-10}$ and H$_2$L$^{9-10}$

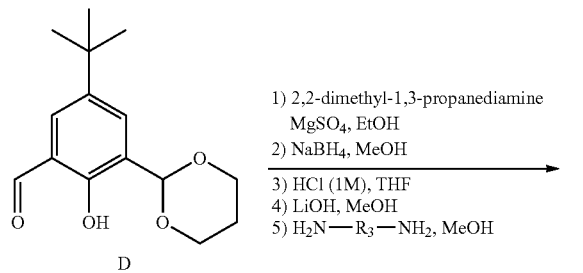

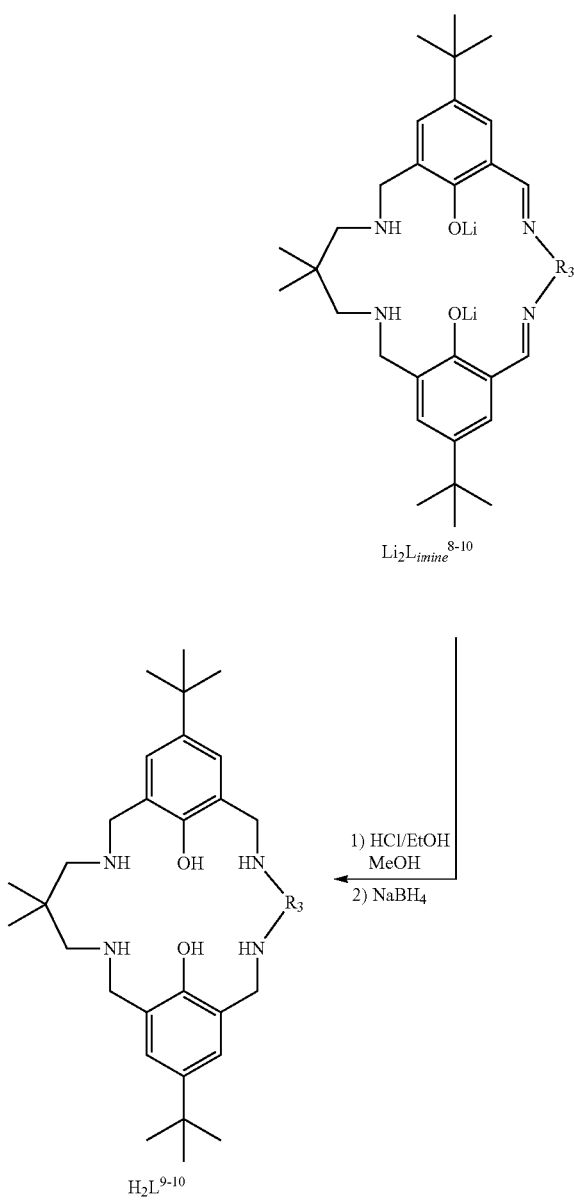

The asymmetric ligands Li$_2$L$_{imine}$$^{8-10}$ and H$_2$L$^{9-10}$ were prepared using the following method:

Preparation of Li$_2$L$_{imine}$$^{8-10}$:

To a solution of D (56.3 mmol) in EtOH (500 mL) was added 2,2-dimethyl-1,3-propanediamine (28.2 mmol) and MgSO$_4$ (281.5 mmol). Reaction mixture was stirred 3 h at RT. After this time, reaction medium was filtered, filter cake was washed with DCM, and the mother liquor was evaporated in vacuo to yield a yellow solid. The latter was solubilised in MeOH, and the reaction medium was cooled to 0° C. NaBH$_4$ (258.0 mmol) was added by portion. Reaction mixture was allowed to stir overnight at RT. After this time, solvents were evaporated in vacuo. DCM and water were added, phases were separated, and the aqueous phase was extracted with DCM. The organic layers were combined and dried over Na$_2$SO$_4$. Solvents were evaporated in vacuo to yield a product that was purified by recrystallization (DCM/MeOH, 20.9 mmol). To a solution of this purified product (17.5 mmol) in THF (200 mL) was added HCl (1M, 400 mL). Reaction mixture was refluxed overnight. After this time, DCM was added, phases were separated, and the aqueous phase was extracted with DCM. The organic layers were combined and dried over Na$_2$SO$_4$. Solvents were evaporated in vacuo to yield a crude product that was purified by recrystallization (DCM/heptane, 15.9 mmol). The latter product (9 mmol) was next solubilised in MeOH (150 mL) and LiOH (36 mmol) was added. Reaction mixture was stirred for 1 h at RT. After this time, a yellow precipitate had formed, was collected by filtration, and washed with ice-cold MeOH. To a suspension of this yellow product (1 equiv.) in MeOH was added dropwise and over 6 h a solution of the appropriate diamine (2,2-dimethyl-1,3-propanediamine, 1,3-propanediamine or ethylenediamine, 1 equiv.) in MeOH at RT. Reaction mixture was then stirred overnight at RT. After this time, a yellow precipitate had formed, was collected by filtration, and washed with ice-cold MeOH. Products were identified as Li$_2$L$_{imine}$$^{8-10}$.

Preparation of H$_2$L$^{9-10}$:

To a suspension of Li$_2$L$_{imine}$$^{9-10}$ (1 equiv.) in MeOH was added HCl (1.25M in EtOH, 6 equiv.) and NaBH$_4$ (20 equiv.). Reaction mixture was stirred overnight at RT. After this time, solvents were evaporated in vacuo. DCM and water were added, phases were separated, and the aqueous phase was extracted with DCM. The organic layers were combined, washed with brine and dried over Na$_2$SO$_4$. Solvents were evaporated in vacuo to yield H$_2$L$^{9-10}$.

H$_2$L$^9$:

$^1$H NMR (400 MHz, CDCl$_3$) δ 6.96 (d, J=2.5 Hz, 2H), 6.95 (d, J=2.5 Hz, 2H), 3.83 (s, 8H), 2.65 (t, J=6.5 Hz, 4H), 2.51 (s, 4H), 1.78-1.73 (m, 2H), 1.25 (s, 18H), 1.01 (s, 6H). MS (ESI) m/z: 525.4 ([M+H]$^+$, 100%)

H$_2$L$^{10}$:

$^1$H NMR (400 MHz, CDCl$_3$) δ 6.97 (d, J=2.5 Hz, 2H), 6.95 (d, J=2.5 Hz, 2H), 3.82 (s, 4H), 3.80 (s, 4H), 2.84 (s, 4H), 2.52 (s, 4H), 1.26 (s, 18H), 0.97 (s, 6H). MS (ESI) m/z: 511.3 ([M+H]$^+$, 100%)

Example 6: Synthesis of Asymmetric Ligands H₂L¹²⁻¹³

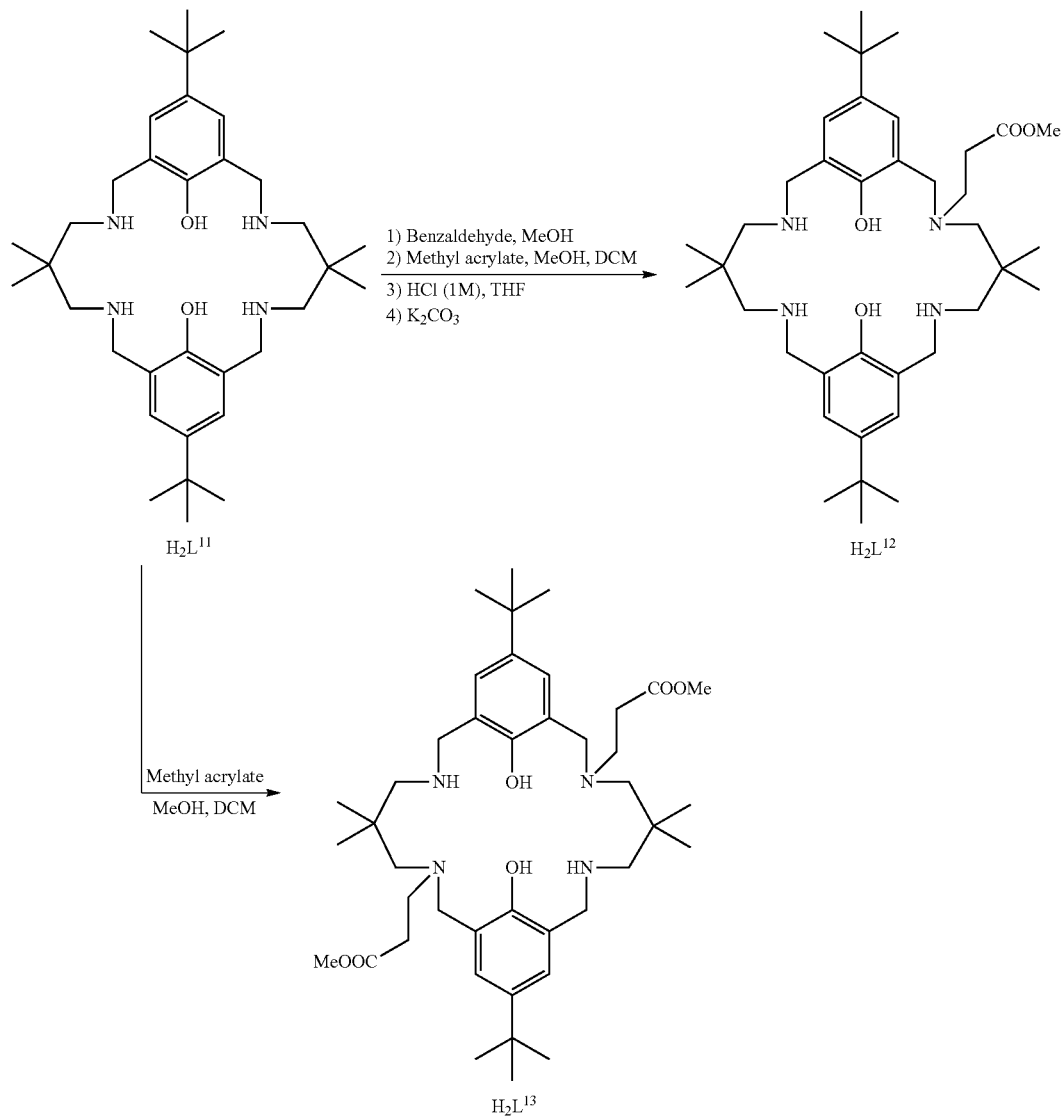

The asymmetric ligands $H_2L^{12-13}$ were prepared using the following methods:

For the preparation of $H_2L^{11}$, see example 1.

Preparation of $H_2L^{12}$:

To a solution of $H_2L^{11}$ (5.4 mmol) in MeOH (100 mL) was added benzaldehyde (6.5 mmol) and the reaction stirred at RT for 3 h. The white precipitate formed was isolated by filtration and washed with cold MeOH (3.78 mmol). A solution of this white product (0.78 mmol) in MeOH (10 mL) and DCM (5 mL) was treated with methyl acrylate (0.94 mmol) and the reaction stirred at RT for 16 h after which the solvent was removed in vacuo to yield a white powder (0.74 mmol). To a solution of this white powder (0.14 mmol) in THF (10 mL) was added aq. 1M HCl until pH 3 was obtained (ca. 4 mL) and the reaction stirred at RT for 3 h. Neutralisation with aq. $K_2OO_3$ followed by extraction with DCM afforded $H_2L^{12}$ (0.04 mmol).

MS (ES/CI) m/z: 639.4 ([M+H]⁺, 100%)

IR ($v_{C=O}$, cm⁻¹, neat): 3300, 2955, 2907, 2869, 1741, 1611, 1465, 1395, 1362, 1298, 1216.

Preparation of $H_2L^{13}$:

To a solution of $H_2L^{11}$ (9.0 mmol) in MeOH (125 mL) was added methyl acrylate (19.0 mmol) and the reaction stirred at RT for 16 h. The white solid formed was isolated by filtration and washed with cold MeOH. Recrystallisation from hot EtOH gave $H_2L^{13}$.

$H_2L^{13}$:

¹H NMR (400 MHz, CDCl₃) δ 7.33 (d, J=2.5 Hz, 2H), 6.75 (d, J=2.5 Hz, 2H), 3.75 (s, 6H), 3.42 (br s, 4H), 3.20 (br s, 4H), 2.94 (br s, 4H), 2.69 (t, J=2.7 Hz, 4H), 2.32 (br s, 4H), 1.42 (s, 18H), 0.88 (s, 12H), 0.24 (br s, 4H).

MS (ES/CI) m/z: 725.3 ([M]⁺, 100%)

IR (cm⁻¹, neat): 3301, 2955, 2907, 2869, 1741, 1480, 1216, 1100.

Example 7: Synthesis of Asymmetric Ligands H$_2$L$^{14-15}$

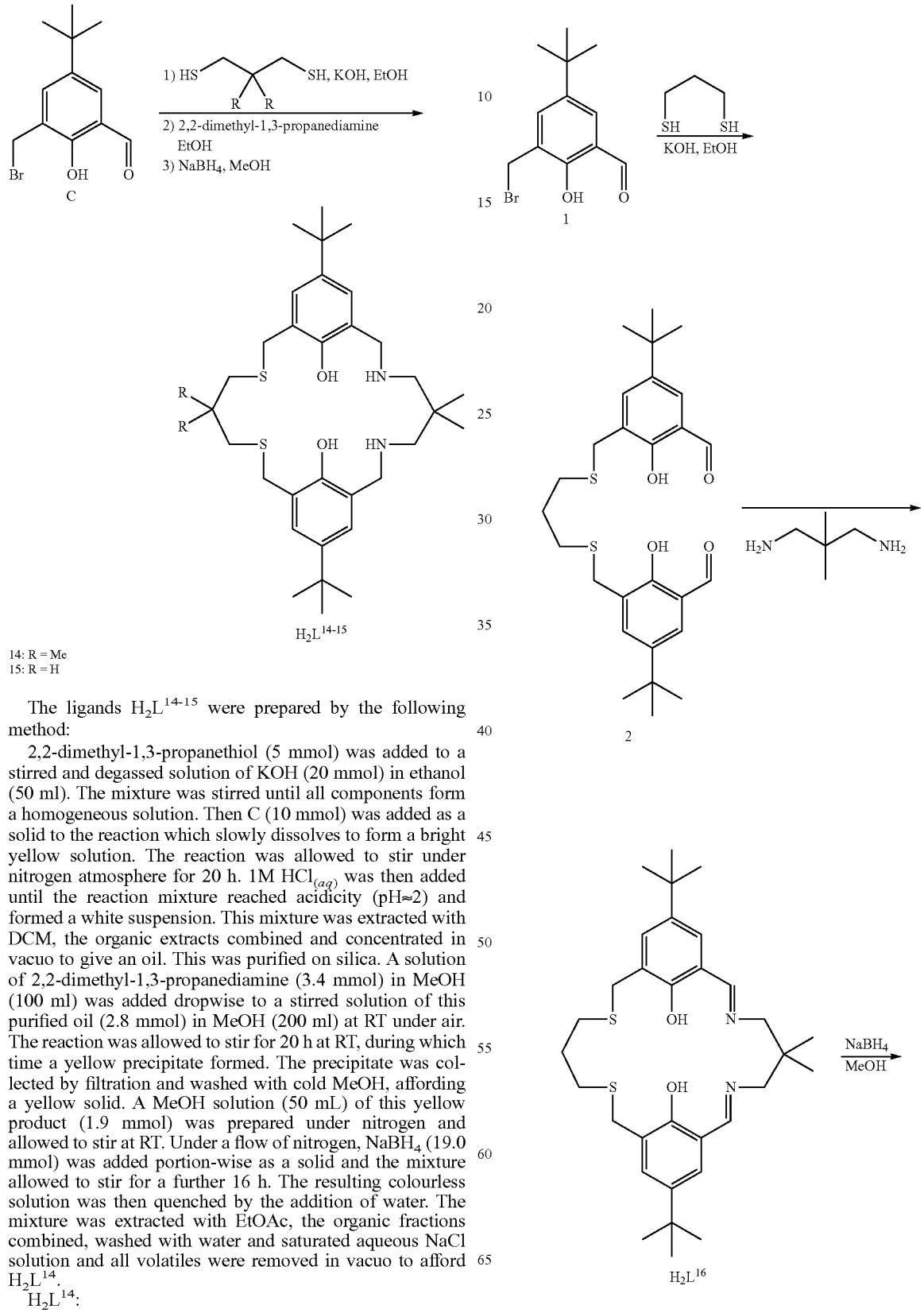

14: R = Me
15: R = H

The ligands H$_2$L$^{14-15}$ were prepared by the following method:

2,2-dimethyl-1,3-propanethiol (5 mmol) was added to a stirred and degassed solution of KOH (20 mmol) in ethanol (50 ml). The mixture was stirred until all components form a homogeneous solution. Then C (10 mmol) was added as a solid to the reaction which slowly dissolves to form a bright yellow solution. The reaction was allowed to stir under nitrogen atmosphere for 20 h. 1M HCl$_{(aq)}$ was then added until the reaction mixture reached acidicity (pH≈2) and formed a white suspension. This mixture was extracted with DCM, the organic extracts combined and concentrated in vacuo to give an oil. This was purified on silica. A solution of 2,2-dimethyl-1,3-propanediamine (3.4 mmol) in MeOH (100 ml) was added dropwise to a stirred solution of this purified oil (2.8 mmol) in MeOH (200 ml) at RT under air. The reaction was allowed to stir for 20 h at RT, during which time a yellow precipitate formed. The precipitate was collected by filtration and washed with cold MeOH, affording a yellow solid. A MeOH solution (50 mL) of this yellow product (1.9 mmol) was prepared under nitrogen and allowed to stir at RT. Under a flow of nitrogen, NaBH$_4$ (19.0 mmol) was added portion-wise as a solid and the mixture allowed to stir for a further 16 h. The resulting colourless solution was then quenched by the addition of water. The mixture was extracted with EtOAc, the organic fractions combined, washed with water and saturated aqueous NaCl solution and all volatiles were removed in vacuo to afford H$_2$L$^{14}$.

H$_2$L$^{14}$:

$^1$H NMR (CDCl$_3$, 400.1 MHz): δ 7.16 (m, 2H), 6.89 (m, 2H), 3.93 (m, 2H), 3.71 (m, 6H), 2.56 (s, 4H), 2.50 (s, 4H), 1.26 (s, 18H), 0.98 (d, 12H)

MS (CI) m/z: 587.4 [M+H]$^+$

58

Example 8: Synthesis of [L$^{1-15}$M$_2$(X$_2$)] Catalysts

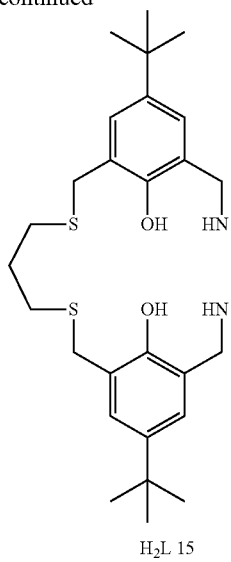

H$_2$L 15

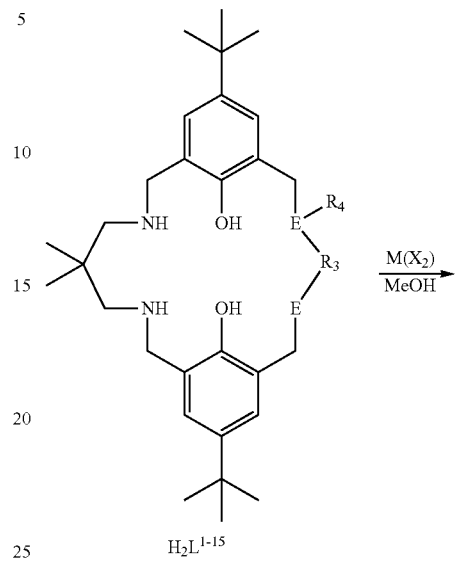

H$_2$L$^{1-15}$ 1,3-propanedithiol (0.56 mL, 5.5 mmol) was dissolved in EtOH (50 mL) in a fumecupboard. A solution of C (3 g, 11.1 mmol) in EtOH (50 mL) was added dropwise over 15 minutes and the mixture stirred overnight. The solvent was removed under vacuum and distilled water (50 mL) was added. The product was extracted with DCM (2×30 mL), dried over NaSO$_4$ and the solvent removed under vacuum. The product (was purified by column chromatography (95:5 Cyclohexane:EtOAc) to give a light yellow oil (54%) $^1$H NMR (CDCl$_3$) δ: 11.22 (s, 2H), 9.90 (s, 2H), 7.60 (d, 2H), 7.45 (d, 2H), 3.79 (s, 4H), 2.61 (t, 4H), 1.93 (q, 2H), 1.35 (s, 18H).

The half macrocycle (0.484 g, 0.99 mmol) was dissolved in MeOH (35 mL). A solution of 2,2-dimethyl-1,3-propane (0.12 mL, 0.99 mmol) in MeOH (25 mL) was added dropwise over 30 minutes and the solution stirred overnight. A yellow precipitate was filtered off and washed with MeOH. $^1$H NMR (CDCl$_3$) δ: 13.74 (br s, 2H), 8.34 (s, 2H), 7.37 (s, 2H), 7.17 (s, 2H), 3.83 (s, 4H), 3.48 (s, 4H), 2.64 (t, 4H), 1.98 (m, 2H), 1.31 (s, 18H), 1.08 (s, 6H).

The yellow precipitate (0.25 g, 0.44 mmol) was dissolved in dry MeOH (50 mL) before NaBH$_4$ (0.2 g, 4.4 mmol) was added in portions. The solution was stirred for 2 hours after which the solvent was removed under vacuum. Water (50 mL) was added to the crude and the pH brought up to 6-7 by adding AcOH dropwise. The product (H$_2$L$^{15}$) was extracted with DCM (2×25 mL), dried over NaSO4 and the solvent removed under vacuum.

$^1$H NMR (CDCl$_3$) δ: 7.22 (s, 2H), 6.88 (s, 2H), 4.01 (s, 4H), 3.66 (s, 4H), 2.50 (s, 4H), 2.38 (t, 4H), 1.6 (q, 2H), 1.29 (s, 18H), 1.06 (s, 6H). $^{13}$C NMR (CDCl$_3$) δ: 153.3, 141.6, 126.6, 125.3, 123.8, 121.0, 57.6, 54.0, 34.7, 34.0, 31.6, 30.3, 29.8, 29.5, 24.5. ESI-MS: 559.3 ([M+H]$^+$, 100%).

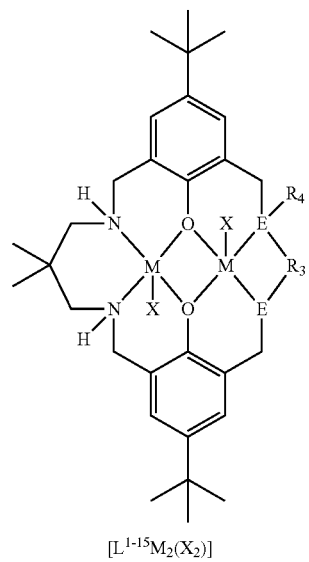

[L$^{1-15}$M$_2$(X$_2$)]

The complexes [L$^{1-15}$M$_2$(X$_2$)] were prepared using the following method:

General Procedure:

To a suspension of H$_2$L$^{1-15}$ (1 equiv.) in MeOH was added the appropriate metal precursor M(X)$_2$ (2 equiv.; Ni(OAc)$_2$·4H$_2$O, Mg(OAc)$_2$·4H$_2$O or Zn(OAc)$_2$·2H$_2$O). Reaction mixture was stirred overnight at RT. After this time, solvents were evaporated and excess water/AcOH was removed by azeotrope with toluene to yield the desired complexes [L$^{1-15}$M$_2$(X)$_2$].

[L$^1$Ni$_2$(OAc)$_2$]:

MS (ES) m/z: 741.3 ([M−OAc]$^+$, 100%).

IR ($\nu_{C=O}$, cm$^{-1}$, neat): 1581, 1410.

[L$^2$Ni$_2$(OAc)$_2$]:

MS (ES/CI) m/z: 753.2 ([M−OAc]$^+$, 100%).

IR ($\nu_{C=O}$, cm$^{-1}$, neat): 1581, 1413.

[L$^2$Zn$_2$(OAc)$_2$]:

MS (ES/CI) m/z: 751.2 ([M−2AcO$^-$+HCO$_2^-$]$^+$, 100%).

IR ($\nu_{C=O}$, cm$^{-1}$, neat): 1603, 1383.

[L$^3$Ni$_2$(OAc)$_2$]:

MS (ES/CI) m/z: 767.2 ([M−OAc]$^+$, 100%).

IR ($\nu_{C=O}$, cm$^{-1}$, neat): 1581, 1413.

[L$^3$Mg$_2$(OAc)$_2$]:

$^1$H NMR (400 MHz, MeOD) δ 7.02 (m, 4H), 3.74 (d, J=18.9 Hz, 4H), 3.6 (d, J=8.9 Hz, 4H), 2.46 (d, J=8.7 Hz, 4H), 2.44 (m, 2H), 2.41 (d, J=8.7 Hz, 2H), 1.90 (s, 6H), 1.54 (m, 2H), 1.30 (s, 9H), 1.28 (s, 9H), 0.96 (s, 6H), 0.95 (s, 6H), 0.84 (t, J=7.3 Hz, 3H).

MS (ES/CI) m/z: 685.3 ([M−2OAc]$^+$, 100%).

IR ($\nu_{C=O}$, cm$^{-1}$, neat): 1607, 1395.

[L$^4$Ni$_2$(OAc)$_2$]:

MS (ES/CI) m/z: 781.2 ([M−OAc]$^+$, 100%).

IR ($\nu_{C=O}$, cm$^{-1}$, neat): 1581, 1413.

[L$^7$Ni$_2$(OAc)$_2$]:

MS (ES/CI) m/z: 739.2 ([M−2OAc+O$_2$CH]$^+$, 100%).

IR ($\nu_{C=O}$, cm$^{-1}$, neat): 1581, 1414.

[L$^9$Mg$_2$(OAc)$_2$]:

$^1$H NMR (400 MHz, CD$_3$OD) δ 7.01 (s, 4H), 4.00 (d, J=3.6 Hz, 2H), 3.97 (d, J=3.7 Hz, 2H), 3.27 (d, J=12.0 Hz, 2H), 3.21 (d, J=12.0 Hz, 2H), 3.05-2.99 (m, 2H), 2.79-2.70 (m, 4H), 2.64 (d, J=11.6 Hz, 2H), 1.94-1.76 (m, br, 4H), 1.25 (s, 18H), 1.23 (s, 3H), 1.01 (s, 3H)

MS (ESI) m/z: 615.3 ([M−2AcO$^-$+HCO$_2^-$]$^+$, 100%).

[L$^9$Ni$_2$(OAc)$_2$]:

MS (ESI) m/z: 683.2 ([M−2AcO$^-$+HCO$_2^-$]$^+$, 100%). IR ($\nu_{C=O}$, cm$^{-1}$, neat): 1566, 1477.

[L$^9$Ni$_2$(OAc)$_2$]:

MS (ESI) m/z: 683.2 ([M−2AcO$^-$+HCO$_2^-$]$^+$, 100%). IR ($\nu_{C=O}$, cm$^{-1}$, neat): 1566, 1477.

[L$^{10}$Ni$_2$(OAc)$_2$]:

MS (ESI) m/z: 669.1 ([M−2OAc+O$_2$CH]$^+$, 100%). IR ($\nu_{C=O}$, cm$^{-1}$, neat): 1566, 1477.

[L$^{13}$Ni$_2$(OAc)$_2$]:

MS (ES/CI) m/z: 855.2 ([M−2AcO$^-$−2CH$_3$+HCO$_2$]$^+$, 100%), 809.2 ([M−2AcO$^-$−2CH$_3$+1HCO$_2$]$^+$, 80%).

IR ($\nu_{C=O}$, cm$^{-1}$, neat): 1573, 1480.

[L$^{14}$Ni$_2$(OAc)$_2$]:

IR ($\nu_{C=O}$, cm$^{-1}$, neat): 1566 and 1413.

[L$^{15}$Ni$_2$(OAc)$_2$]:

MS (CI) m/z: 717 ([M−2AcO$^-$+HCO$_2^-$]$^+$, 100%).

IR ($\nu_{C=O}$, cm$^{-1}$, neat): 1562 and 1410.

Example 9: Synthesis of [L$_{imine}$$^8$Mg$_2$(OAc)$_2$] Complex

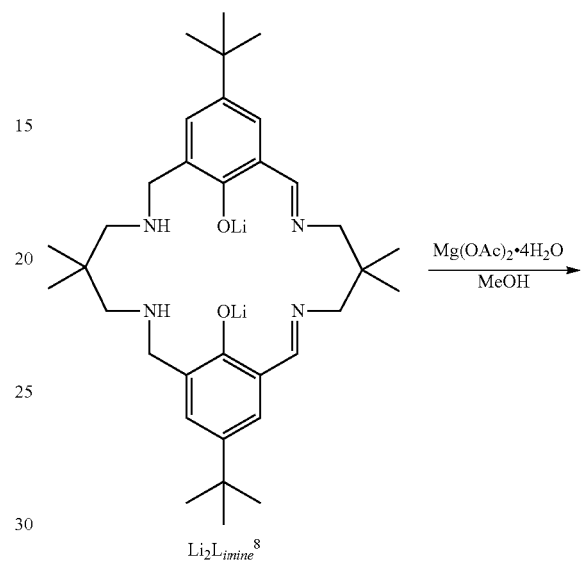

Li$_2$L$_{imine}$$^8$

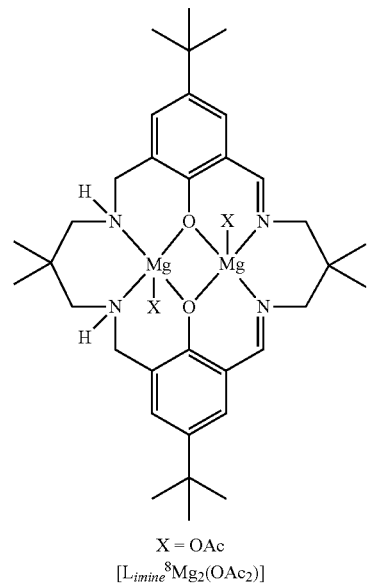

X = OAc
[L$_{imine}$$^8$Mg$_2$(OAc$_2$)]

The complex [$L_{imine}^8Mg_2(OAc)_2$] was prepared using the following method:

Preparation of [$L_{imine}^8Mg_2(OAc)_2$]:

To a suspension of $Li_2L_{imine}^8$ (1 equiv.) in MeOH was added $Mg(OAc)_2 \cdot 4H_2O$ (2 equiv.). Reaction mixture was stirred overnight at RT. After this time, solvents were evaporated. Pentane was added and the reaction mixture was filtered. Filtrate was evaporated to yield complex [$L_{imine}^8Mg_2(OAc)_2$] as a slightly yellow solid.

$L_{imine}^8Mg_2(OAc)_2$:

$^1$H NMR (400 MHz, $CD_3OD$) δ 8.13 (d, J=2.0 Hz, 2H), 7.31 (d, J=2.7 Hz, 2H), 7.26 (d, J=2.7 Hz, 2H), 4.09-4.03 (m, 4H), 3.31-3.26 (m, 2H), 2.86-2.79 (m, 2H), 2.66 (d, J=11.3 Hz, 2H), 2.22-2.14 (m, 2H), 1.90-1.40 (s, br, 6H), 1.31 (s, 18H), 1.21 (s, 3H), 1.16 (s, 3H), 1.14 (s, 3H), 1.02 (s, 3H). MS (ESI) m/z: 639.3 ([M−2AcO$^-$+HCO$_2^-$]$^+$, 100%).

Example 10: Polymerisation of $CO_2$ and CHO at 100° C. and 0.01 mmol of [$LM_2(OAc)_2$]

[$LM_2(OAc)_2$] (0.01 or 0.025 mmol) was dissolved in cyclohexene oxide (25 or 50 mmol) in a Schlenk. The vessel was degassed, charged with $CO_2$ (1 bar) and heated at 100° C. with magnetic stirring for the right time, giving poly(cyclohexene carbonate). The polymer contained >99% carbonate linkages and was produced with >99% selectivity in all cases. The asymmetric ligands L1-L4 having N-substitution demonstrate superior activity, productivity (turnover number) and activity under low loadings. All the asymmetric complexes demonstrate excellent selectivity for polymer, activity under low pressures and narrow polydispersity polymers. The results are shown in Table 1.

Example 11: Polymerisation of $CO_2$ and CHO at 130° C. and High Pressure with [$LM_2(OAc)_2$]

[$L^xM_2(OAc)_2$] (0.0148 mmol) was added to a dried Schlenk tube and dried under vacuum for 60 minutes. CHO (15 mL, 148.26 mmol) was added under $N_2$ via a syringe, the mixture was transferred to a reactor under pressure 0.2 bar CO2. Reactor vessel was heated to 130° C., then pressured to 10 bar and stirred for 1-2 hours, after which the vessel was cooled to 5° C., the pressure slowly released and a sample taken for GPC/NMR analysis. The results are shown in Table 2.

TABLE 2

Comparison of catalytic activity of equivalent Ni and Mg complexes under identical conditions for CHO and $CO_2$ (10 bar) copolymerisation at 1:10,000 loading.

| Catalyst | cat:CHO | Vol CHO (mL) | T (° C.) | P (bar) | Time (h) | Conversion (PCHC + Cyclic vs CHO) | Selectivity | TON | TOF | PDI | Mn |
|---|---|---|---|---|---|---|---|---|---|---|---|
| [$L^{11}Mg_2(OAc)_2$] | 1:10000 | 15 | 130 | 10 | 2 | 44.2% | 100% | 4420 | 2210 | 1.192 | 15100 |
| [$L^{11}Ni_2(OAc)_2$] | 1:10000 | 15 | 130 | 10 | 2 | 51.6% | 98.5% | 5156 | 2578 | 1.264 | 29400 |
| [$L^1Ni_2(OAc)_2$] | 1:10000 | 15 | 130 | 10 | 1 | 44.5% | 99.8% | 4450 | 4450 | 1.234 | 21300 |

Although the symmetrical magnesium catalyst [$L^{11}Mg_2(OAc)_2$] and nickel catalyst [$L^{11}Ni_2(OAc)_2$] perform well and have high selectivity and activity (TOF) the asymmetric catalyst [$L^1Ni_2(OAc)_2$] has a far superior activity and produces the same turn-over-number in half the time. This clearly demonstrates the unexpected benefits that an asymmetric catalyst can give over a symmetric catalyst.

Example 12: Polymerisation of $CO_2$ and PO with [$LM_2(OAc)_2$]

[$L^xM_2(OAc)_2$] (0.0043-0.21 mmol) was dissolved in propylene oxide (211 mmol) in a Schlenk tube and the solution transferred into a pre-dried 100 mL stainless steel Parr pressure vessel using a syringe. The vessel was charged with $CO_2$ (20 bar) and heated to the desired temperature ° C. The solution was stirred mechanically for the desired time, giving poly(propylene carbonate) as a white solid with a high selectivity for polymer and >99% carbonate linkages. The catalysts showed excellent activity, producing a high yield of polymer. The catalysts demonstrated significantly improved selectivity and activity when compared to symmetric catalyst [$L^{11}Ni_2(OAc)_2$] and could be used at a much lower catalyst loading. The results are shown in Table 3.

TABLE 1

Copolymerisation of CHO and $CO_2$ using [$LM_2(OAc)_2$]

| Catalyst | cat:CHO | Vol CHO (mL) | T (° C.) | P (bar) | Time (h) | Conversion (PCHC + Cyclic vs CHO) | Selectivity | TON | TOF | PDI | Mn |
|---|---|---|---|---|---|---|---|---|---|---|---|
| [$L^1Ni_2(OAc)_2$] | 1:5000 | 5 | 100 | 1 | 3 | 44% | 100% | 2203 | 734 | 1.254 | 12600 |
| [$L^1Ni_2(OAc)_2$] | 1:1000 | 2.5 | 100 | 1 | 1.17 | 51.8 | 99.9% | 518 | 443 | 1.018/1.051 | 16300/9200 |
| [$L^2Ni_2(OAc)_2$] | 1:5000 | 5 | 100 | 1 | 3 | 44% | 100% | 2212 | 737 | 1.29 | 13100 |
| [$L^3Ni_2(OAc)_2$] | 1:5000 | 5 | 100 | 1 | 3 | 47% | 100% | 2370 | 790 | 1.234 | 12900 |
| [$L^4Ni_2(OAc)_2$] | 1:5000 | 5 | 100 | 1 | 3 | 48% | 100% | 2381 | 794 | 1.241 | 12900 |
| [$L_{imine}^8Mg_2(OAc)_2$] | 1:1000 | 2.5 | 100 | 1 | 4 | 32.55% | 100% | 326 | 81 |  |  |
| [$L^9Ni_2(OAc)_2$] | 1:1000 | 2.5 | 100 | 1 | 3 | 27.9% | 99.5% | 279 | 93 | 1.042/1.095 | 12700/5300 |
| [$L^9Mg_2(OAc)_2$] | 1:1000 | 2.5 | 100 | 1 | 3 | 43.23% | 100% | 432 | 144 | 1.035/1.196 | 20400/6600 |

TABLE 3

Copolymerisation of PO and $CO_2$ using $[LM_2(OAc)_2]$

| Catalyst | cat:PO | T (° C.) | P (bar) | Time (h) | Selectivity for polymer | Polymer yield | PDI | Mn |
| --- | --- | --- | --- | --- | --- | --- | --- | --- |
| $[L^1Ni_2(OAc)_2]$ | 1:5000 | 80 | 20 | 9 | 85% | 6.8 g | 1.027/1.032 | 34000/16900 |
| $[L^2Ni_2(OAc)_2]$ | 1:5000 | 80 | 20 | 9 | 89% | 8 g | 1.027/1.030 | 42600/21200 |
| $[L^3Ni_2(OAc)_2]$ | 1:5000 | 80 | 20 | 9 | 87% | 7.8 g | 1.025/1.028 | 38900/19300 |
| $[L^1Ni_2(OAc)_2]$ | 1:1000 | 70 | 20 | 16 | 87% | 19 g | 1.034/1.030 | 44500/22300 |
| $[L^1Ni_2(OAc)_2]$ | 1:50000 | 90 | 20 | 16 | 80% | 2.2 g | 1.1 | 19700 |
| $[L^7Ni_2(OAc)_2]$ | 1:1000 | 80 | 20 | 1 | 90% | 8.5 g | 1.02/1.03 | 17000/8600 |
| $[L^{11}Ni_2(OAc)_2]$ | 1:1000 | 80 | 20 | 16 | 75% | 10.4 g | 1.12 | 15200 |

Example 13: Polymerisation of $CO_2$ and PO with $[L^1Ni_2(OAc)_2]$ in the Presence of a Starter—PPG-425

$[L^1Ni_2(OAc)_2]$ (0.21 mmol) and PPG-425 (4.3 mmol) was dissolved in propylene oxide (211 mmol) in a Schlenk tube and the solution transferred into a pre-dried 100 mL stainless steel Parr pressure vessel using a syringe. The vessel was charged with $CO_2$ (20 bar) and heated to the 80° C. The solution was stirred mechanically for the 6 hrs, giving a poly(propylenecarbonate) diol (9.2 g) as a clear viscous oil with a high selectivity for polymer and >99% carbonate linkages.

Example 14: Polymerisation of $CO_2$ and PO with $[L^1Ni_2(OAc)_2]$ in the Presence of a Starter—1,6-hexanediol $[L^1Ni_2(OAc)_2]$ (0.21 mmol) and 1,6-hexanediol (8.4 mmol) was dissolved in propylene oxide (211 mmol) in a Schlenk tube and the solution transferred into a pre-dried 100 mL stainless steel Parr pressure vessel using a syringe. The vessel was charged with $CO_2$ (20 bar) and heated to the 80° C. The solution was stirred mechanically for 12 hrs, giving a poly(propylenecarbonate) diol (6.4 g) as a clear viscous oil with a high selectivity for polymer and >99% carbonate linkages.

Example 15: Polymerisation of $CO_2$ and PO with $[L^1Ni_2(OAc)_2]$ in the Presence of a Solvent—Toluene $[L^1Ni_2(OAc)_2]$ (0.021 mmol) was dissolved in propylene oxide (106 mmol) in a Schlenk tube and a further 7.5 mL of dry toluene was added and the solution transferred into a pre-dried 100 mL stainless steel Parr pressure vessel using a syringe. The vessel was charged with $CO_2$ (20 bar) and heated to the 80° C. The solution was stirred mechanically for the 16 hrs, giving a toluene solution of poly(propylenecarbonate) which was isolated (5 g) as a white powder with a high selectivity for polymer and >99% carbonate linkages.

Example 16: Polymerisation of $CO_2$ and PO with $[L^1Ni_2(OAc)_2]$ in the Presence of a Solvent—n-butyl Acetate $[L^1Ni_2(OAc)_2]$ (0.021 mmol) was dissolved in propylene oxide (106 mmol) in a Schlenk tube and a further 7.5 mL of dry n-butyl acetate was added and the solution transferred into a pre-dried 100 mL stainless steel Parr pressure vessel using a syringe. The vessel was charged with $CO_2$ (20 bar) and heated to the 80° C. The solution was stirred mechanically for 16 hrs, giving an n-butyl acetate solution of poly(propylenecarbonate) which was isolated (4.7 g) as a white powder with a high selectivity for polymer and >99% carbonate linkages.

Example 17: Polymerisation of $CO_2$ and tert-butyl Glycidyl Ether with $[L^1Ni_2(OAc)_2]$ $[L^1Ni_2(OAc)_2]$ (0.105 mmol) was dissolved in tert-butyl glycidyl ether (105 mmol) in a Schlenk tube and the solution transferred into a pre-dried 100 mL stainless steel Parr pressure vessel using a syringe. The vessel was charged with $CO_2$ (20 bar) and heated to the 80° C. The solution was stirred mechanically for 16 hrs, giving poly(tert-butylether 1,2-glycerol carbonate) which was isolated (8.6 g) as a white powder with a high selectivity for polym for polymer and >99% carbonate linkages.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed

The invention claimed is:
1. A catalyst comprising one of the following:
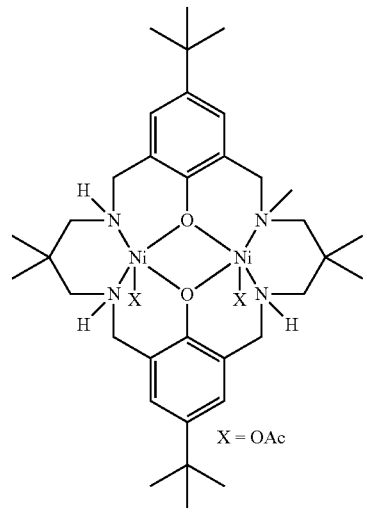
L¹Ni₂(OAc)₂
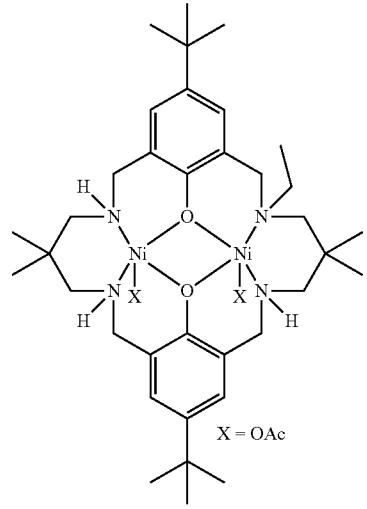
L²Ni₂(OAc)₂
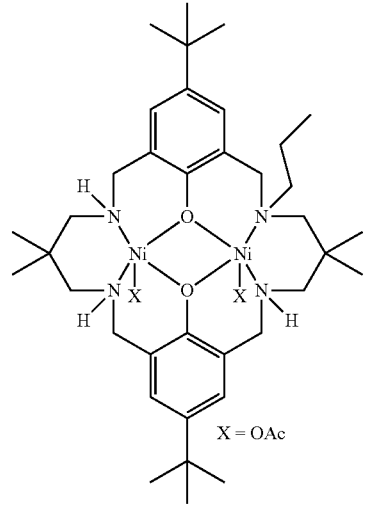
L³Ni₂(OAc)₂
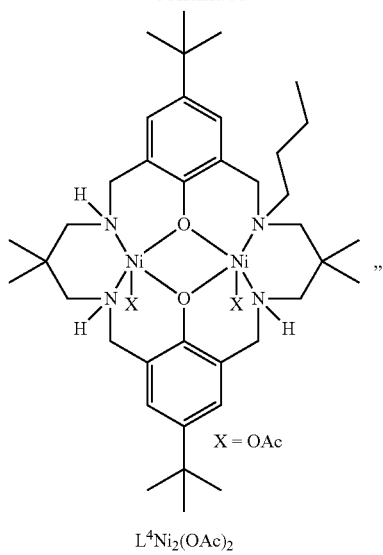
L⁴Ni₂(OAc)₂
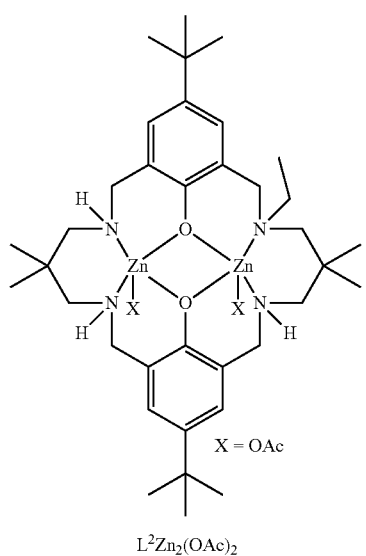
L²Zn₂(OAc)₂
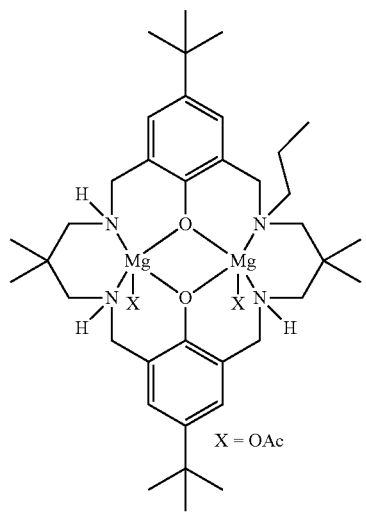
L³Mg₂(OAc)₂

-continued
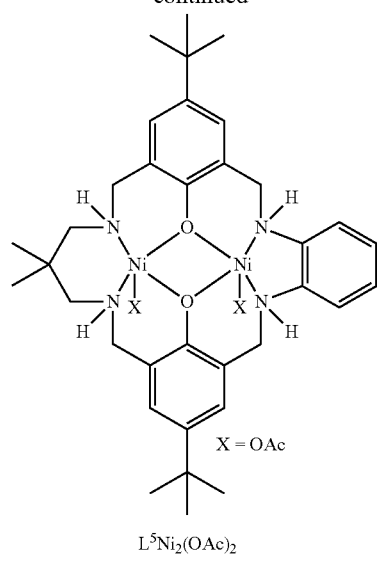
X = OAc
L⁵Ni₂(OAc)₂
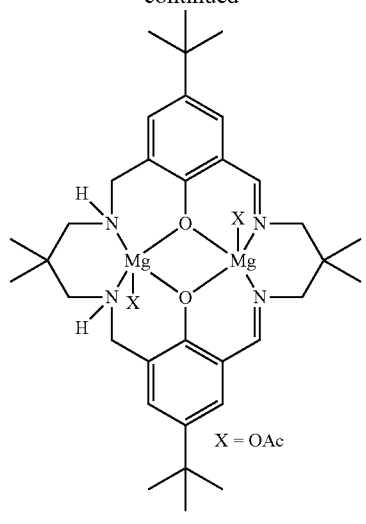
X = OAc
[L_imine⁸Mg₂(OAc₂)]
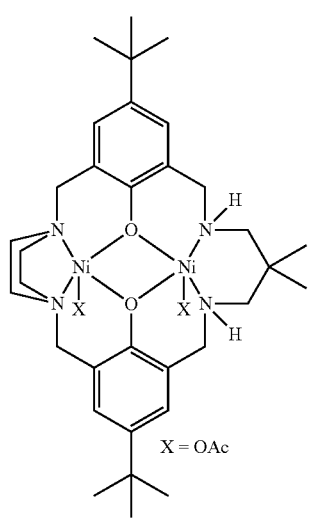
X = OAc
L⁶Ni₂(OAc)₂
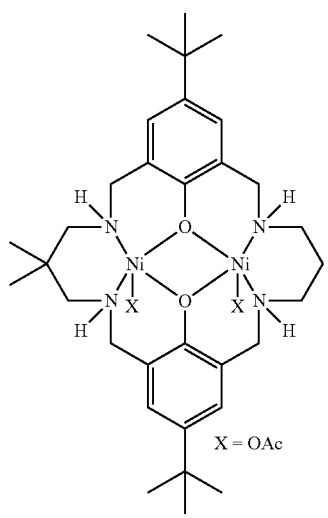
X = OAc
L⁹Ni₂(OAc)₂
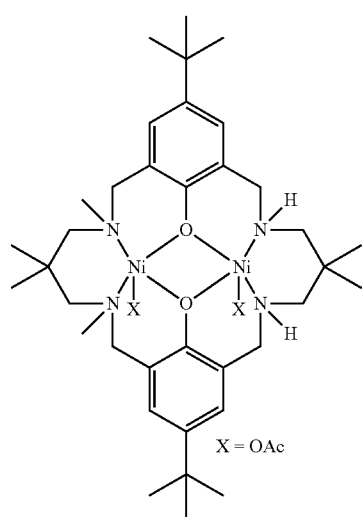
X = OAc
L⁷Ni₂(OAc)₂
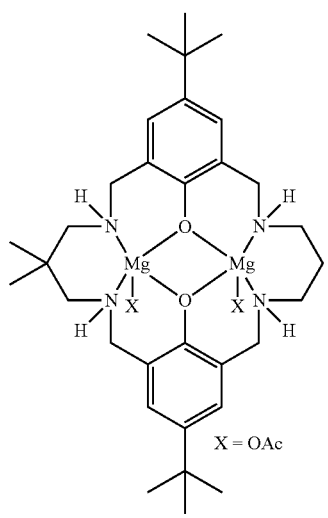
X = OAc
L⁹Mg₂(OAc)₂

-continued
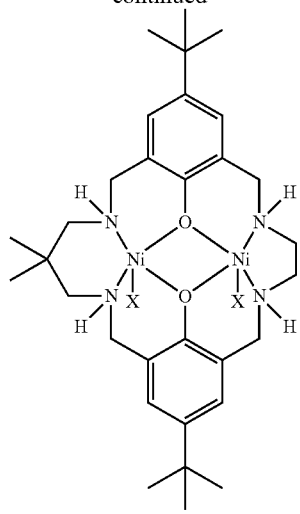
L¹⁰Ni₂(OAc)₂
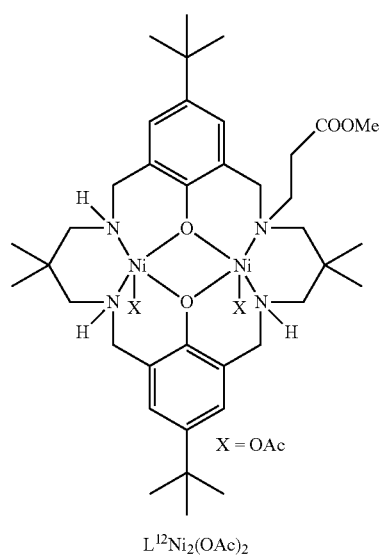
X = OAc
L¹²Ni₂(OAc)₂
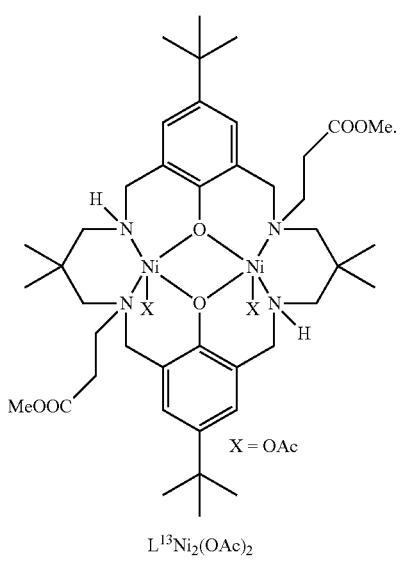
X = OAc
L¹³Ni₂(OAc)₂
2. The catalyst of claim 1 of the formula:
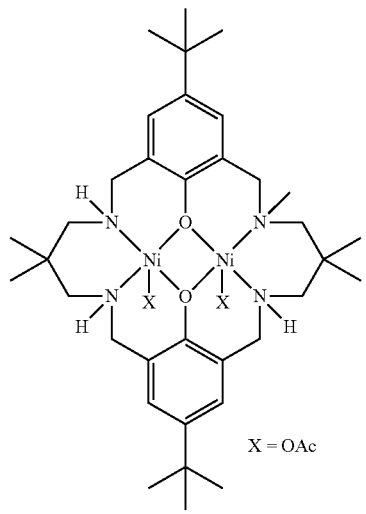
X = OAc
L¹Ni₂(OAc)₂
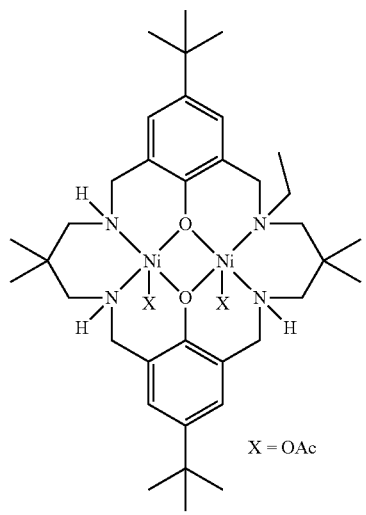
X = OAc
L²Ni₂(OAc)₂
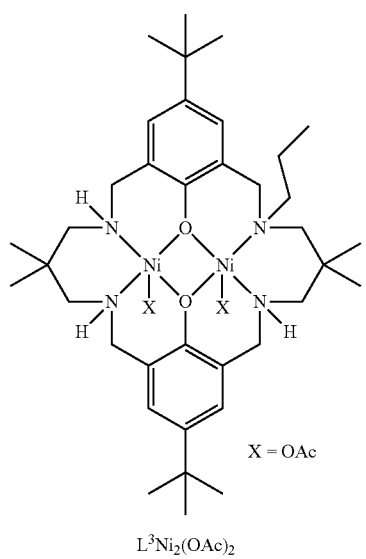
X = OAc
L³Ni₂(OAc)₂

71
-continued

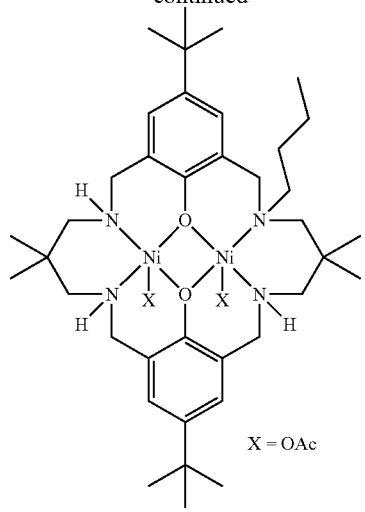

L⁴Ni₂(OAc)₂ ,,

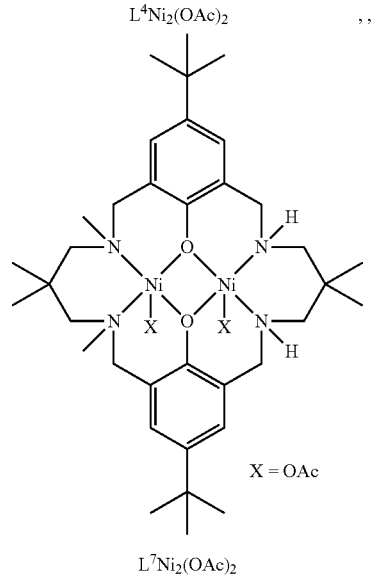

L⁷Ni₂(OAc)₂

72
-continued

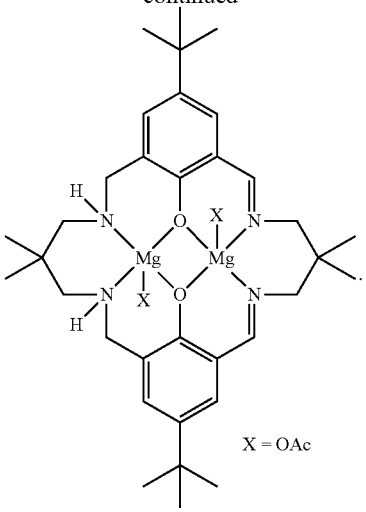

[L$_{imine}^{8}$Mg₂(OAc₂)] .

3. A process for the reaction of (i) carbon dioxide with an epoxide;

(ii) an epoxide and an anhydride; and/or (iii) a lactide and/or a lactone, in the presence of the catalyst of claim 1, optionally wherein the process is carried out in the presence of a chain transfer agent.

4. The process of claim 3, wherein the process is carried out in a continuous flow reactor, or a batch reactor.

5. The process of claim 4, wherein the reaction is carried out in a continuous flow reactor.

* * * * *